(12) United States Patent
Liu et al.

(10) Patent No.: US 11,365,254 B2
(45) Date of Patent: *Jun. 21, 2022

(54) BISPECIFIC CD3/CD19 POLYPEPTIDE COMPLEXES

(71) Applicant: WUXI BIOLOGICS IRELAND LIMITED, Dundalk (IE)

(72) Inventors: Jieying Liu, Shanghai (CN); Jianqing Xu, Shanghai (CN); Zhuozhi Wang, Shanghai (CN); Qin Mei, Shanghai (CN); Jing Li, Shanghai (CN)

(73) Assignee: WUXI BIOLOGICS IRELAND LIMITED, County Louth (IE)

( * ) Notice: Subject to any disclaimer, the term of this patent is extended or adjusted under 35 U.S.C. 154(b) by 150 days.

This patent is subject to a terminal disclaimer.

(21) Appl. No.: 16/648,792

(22) PCT Filed: Sep. 20, 2018

(86) PCT No.: PCT/CN2018/106776
§ 371 (c)(1),
(2) Date: Mar. 19, 2020

(87) PCT Pub. No.: WO2019/057124
PCT Pub. Date: Mar. 28, 2019

(65) Prior Publication Data
US 2020/0283523 A1   Sep. 10, 2020

(30) Foreign Application Priority Data

Sep. 22, 2017 (WO) ................ PCT/CN2017/103032

(51) Int. Cl.
| | |
|---|---|
| C07K 16/28 | (2006.01) |
| C12N 15/63 | (2006.01) |
| A61P 35/00 | (2006.01) |
| G01N 33/68 | (2006.01) |
| A61K 39/00 | (2006.01) |

(52) U.S. Cl.
CPC .......... *C07K 16/2809* (2013.01); *A61P 35/00* (2018.01); *C12N 15/63* (2013.01); *G01N 33/6857* (2013.01); *A61K 2039/505* (2013.01); *C07K 2317/31* (2013.01); *C07K 2317/522* (2013.01); *C07K 2317/524* (2013.01); *C07K 2317/526* (2013.01); *C07K 2317/53* (2013.01); *C07K 2317/55* (2013.01); *C07K 2317/565* (2013.01); *G01N 2800/52* (2013.01)

(58) Field of Classification Search
CPC combination set(s) only.
See application file for complete search history.

(56) References Cited

U.S. PATENT DOCUMENTS

| | | | |
|---|---|---|---|
| 5,906,936 A | 5/1999 | Eshhar et al. | |
| 6,335,163 B1 | 1/2002 | Sharon | |
| 7,329,731 B2 | 2/2008 | Jakobsen et al. | |
| 7,381,794 B2 | 6/2008 | Moore et al. | |
| 7,666,604 B2 | 2/2010 | Jakobsen et al. | |
| 7,763,445 B2 | 7/2010 | Moore et al. | |
| 7,763,718 B2 | 7/2010 | Jakobsen et al. | |
| 9,683,052 B2 | 6/2017 | Blein et al. | |
| 9,683,053 B2 | 6/2017 | Blein et al. | |
| 2008/0153131 A1 | 6/2008 | Jakobsen et al. | |
| 2010/0047171 A1 | 2/2010 | Beckmann | |
| 2010/0113300 A1 | 5/2010 | Jakobsen et al. | |
| 2015/0183877 A1 | 7/2015 | Demarest et al. | |
| 2015/0313977 A1 | 11/2015 | Cohen et al. | |
| 2016/0081314 A1 | 3/2016 | Thurston et al. | |
| 2018/0094077 A1 | 4/2018 | Blein et al. | |
| 2019/0048080 A1 | 2/2019 | Cai et al. | |
| 2020/0283524 A1 | 9/2020 | Xu et al. | |

FOREIGN PATENT DOCUMENTS

| | | |
|---|---|---|
| CN | 1561343 A | 1/2005 |
| CN | 1714102 A | 12/2005 |
| CN | 1745099 A | 3/2006 |
| CN | 101802015 A | 8/2010 |
| CN | 102574906 A | 7/2012 |
| CN | 105017422 A | 11/2015 |
| CN | 106883298 A | 6/2017 |

(Continued)

OTHER PUBLICATIONS

Gijsbert et al. (1995) (Abstract Only: Clinical Experience with CD3 X CD19 Bispecific antibodies in Patients with B Cell Malignancies, Journal of Hematotherapy., vol. 4, 1995; published online 2009). (Year: 1995).*
Noelle V. Frey, et al., "Cytokine release syndrome with novel therapeutics for acute lymphoblastic leukemia," *Hematology*, pp. 567-572 (2016).
Hagop Kantarjian, et al., "Blinatumomab versus Chemotherapy for Advanced Acute Lymphoblastic Leukemia," *The New England Journal of Medicine*, vol. 376, pp. 836-847 (2017).
Extended European Search Report for European App. No. 18857563. 3, dated May 11, 2021 (ten pages).
Emma S. Hickman, "Antigen Selection for Enhanced Affinity T-Cell Receptor-Based Cancer Therapies", *Journal of Biomolecular Screening for Laboratory Automation and Screening*, pp. 769-785 (2016).
Ulrich Weidle et al., "TCR-MHC/Peptide Interaction: Prospects for New Anti-tumoral Agents", *Cancer Genomics & Proteomics*, vol. 11, pp. 267-278 (2014).

(Continued)

*Primary Examiner* — Laura B Goddard
*Assistant Examiner* — Sarah A Alsomairy
(74) *Attorney, Agent, or Firm* — Finnegan, Henderson, Farabow, Garrett & Dunner

(57) ABSTRACT

A bispecific anti-CD3×CD19 polypeptide complex that contains a first antigen-binding moiety of the polypeptide complex and a second antigen-binding moiety, methods of producing the bispecific anti-CD3×CD19 polypeptide complex, methods of treating disease or disorder using the bispecific anti-CD3×CD19 polypeptide complex, polynucleotides encoding the bispecific anti-CD3×CD19 polypeptide complex, vectors and host cells containing said polynucleotides, and compositions and pharmaceutical compositions comprising the bispecific anti-CD3×CD19 polypeptide complex are provided.

20 Claims, 18 Drawing Sheets

Specification includes a Sequence Listing.

(56) References Cited

FOREIGN PATENT DOCUMENTS

| | | |
|---|---|---|
| CN | 106922147 A | 7/2017 |
| CN | 107072184 A | 8/2017 |
| CN | 107614519 A | 1/2018 |
| CN | 103608357 B | 3/2018 |
| CN | 104829726 A | 8/2018 |
| EP | 1732946 B1 | 7/2011 |
| RU | 2 548 746 C2 | 4/2015 |
| WO | WO 03/020763 A2 | 3/2003 |
| WO | WO 2004/044004 A2 | 5/2004 |
| WO | WO 2007/085814 A1 | 8/2004 |
| WO | WO 2005/113595 A2 | 12/2005 |
| WO | WO 2006/054096 A1 | 5/2006 |
| WO | WO 2008/119353 A1 | 10/2008 |
| WO | WO 2011/001152 A1 | 1/2011 |
| WO | WO 2011/051307 A1 | 5/2011 |
| WO | WO 2013/041865 A1 | 3/2013 |
| WO | WO 2014/014796 A1 | 1/2014 |
| WO | WO 2016/033570 A1 | 3/2016 |
| WO | WO 2016/048938 A1 | 3/2016 |
| WO | WO 2016/097408 A1 | 6/2016 |
| WO | WO 2017/027392 A1 | 2/2017 |
| WO | WO 2017/053469 A2 | 3/2017 |
| WO | WO 2017/055314 A1 | 4/2017 |
| WO | WO 2017/059900 A1 | 4/2017 |
| WO | WO 2017/060300 A1 | 4/2017 |
| WO | WO 2017/070608 A1 | 4/2017 |
| WO | WO 2017/112944 A1 | 6/2017 |
| WO | WO 2017/192536 A1 | 11/2017 |
| WO | WO 2019/057099 A1 | 3/2019 |
| WO | WO 2019/057122 A1 | 3/2019 |

OTHER PUBLICATIONS

"IMGT/3Dstructure-DB card for 2p5e", IMGT.org, Apr. 26, 2021, http://www.imgt.com/3Dstructure-DB/cgi/details.cgi?pbcode=2p5e.

J. Kuball et al., "Facilitating matched pairing and expression of TCR chains introduced into human T cells", Blood, vol. 109, No. 6, pp. 2331-2338 (2007).

T. T. Junttila et al., "Antitumor Efficacy of a Bispecific Antibody That Targets HER2 and Activities T Cells", Cancer Research, vol. 74, No. 19, pp. 5561-5571 (2014).

Chinese Office Action issued in Application No. 201811100222.5 from The State Intellectual Property Office of People's Republic of China dated Mar. 19, 2020 (9 pages) and its translation from Global Dossier (7 pages).

Bialer, G. et al. "Selected Murine Residues Endow Human TCR with Enhanced Tumor Recognition," J Immunol, 184, 6232-6241, 2010.

Boulter, J.M. et al. "Stable, soluble T-cell receptor molecules for crystallization and therapeutics," Protein Engineering, vol. 16, No. 9, pp. 707-711, 2003.

Eshhar, Z. et al. "Specific activation and targeting of cytotoxic lymphocytes through chimeric single chains consisting of antibody-binding domains and the γ or ζ subunits of the immunoglobulin and T-cell receptors," Proc. Natl. Acad. Sci., USA, 1993, No. 2(90), pp. 720-724.

Goverman, J. et al. "Chimeric Immunoglobulin-T Cell Receptor Proteins Form Functional Receptors: Implications for T Cell Receptor Complex Formation and Activation," Cell, 1990, vol. 60, pp. 929-939.

Huehls, A.M. et al. "Bispecific T cell engagers for cancer immunotherapy," Immunol Cell Biol., Mar. 2015, 93(3), pp. 290-296, doi:10.1038/icb.2014.93.

International Search Report and Written Opinion, issued in PCT/CN2018/106776, dated Dec. 27, 2018, 15 pages.

Kipriyanov, S.M. et al. "Bispecific CD3 XCDL 9 diabody fort cell-mediated lysis of malignant human B cells," Int. J. Cancer, 1998, No. 5(77), pp. 763-772.

Sommermeyer, D. et al. "Minimal Amino Acid Exchange in Human TCR Constant Regions Fosters Improved Function of TCR Gene-Modified T Cells," J Immunol, 184, 6223-6231, 2010.

Wagner, E.K. et al. "Human cytomegalovirus-specific T-cell receptor engineered for high affinity and soluble expression using mammalian cell display," J. Biol. Chem. (2019) 294(15) 5790-5804.

Wu et al. "Blinatumomab: A bispecific T cell engager (BiTE) antibody against CD 19/CD3 for refractory acute lymphoid leukemia," Journal of Hematology & Oncology, 2015, vol. 8, pp. 1-7.

Wu et al. "Protein design of IgG/TCR chimeras for the coexpression of Fab-like moieties within bispecific antibodies," mAbs, 2015, 7(2):364-376.

International Search Report and Written Opinion, issued in PCT/CN2018/106766, dated Dec. 11, 2018, 13 pages.

Spiess et al., "Alternative molecular formats and therapeutic applications for bispecific antibodies," Molecular Immunology, 2015, 67, 95-106.

Seimiya et al., "T cell receptor-extracellular constant regions as hetero-cross-linkers for immunoglobulin variable regions," J. Biochem., 1993, 113, 687-691.

Xiufeng Wu et al., "Protein design of IgG/TCR chimeras for the co-expression of Fab-like moieties within bispecific antibodies", mAbs, 7\2, Mar./Apr. 2015, pp. 364-376.

P.M. Colman, "Effects of amino acid sequence changes on antibody-antigen interactions", 55th Forum in Immunology, pp. 33-36.

Yaghoub Safdari et al., "Antibody humanization methods—a review and update", Biotechnology and Genetic Engineering Reviews, 2013, vol. 29, No. 2, pp. 175-186.

Marcela Torres et al., "The immunoglobulin constant region contributes to affinity and specificity", Trends in Immunology, 2008, vol. 29, No. 2, pp. 91-97.

Xiaoying Chen et al., "Fusion Protein Linkers: Property, Design and Functionality", Adv Drug Deliv Rev., Oct. 1, 20135; 65(10), pp. 1357-1369.

Yumi Maeda et al., "Engineering of Functional Chimeric Protein G-Vargula Luciferase", Analytical Biochemistry, 1997, 249, pp. 147-152.

Mauro Acchione et al., "Impact of linker and conjugation chemistry on antigen binding, Fc receptor binding and thermal stability of model antibody-drug conjugates", mAbs, 2012, 4:3, pp. 362-372.

Eugenia Zah et al., "T cells expressing CD19/CD20 bi-specific chimeric antigen receptors prevent antigen escape by malignant B cells", Cancer Immunol Res., Jun. 2016; 4(6), pp. 498-508.

Sergey M. Kipriyanov et al., "Bispecific CD3 X CD19 Diabody for T Cell-Mediated Lysis of Malignant Human B Cells", Int. J. Cancer, 77, (1998), pp. 763-772.

* cited by examiner

Constant region sequence of TCR alpha chain:

TRAC_Human       PNIQNPDPAV YQLRDSKSSD KSVCLFTDFD SQTNVSQSKD SDVYITDKTV
4L4T_Alpha_Crystal  PDIQNPDPAV YQLRDSKSSD KSVCLFTDFD SQTNVSQSKD SDVYITDKCV TRAC_Human       LDMRSMDFKS NSAVAWSNKS DFACANAFNN SIIPEDTFFP SPESSCDVKL
4L4T_Alpha_Crystal  LDMRSMDFKS NSAVAWSNKS DFACANAFNN SIIPEDTFFP SPESS-----

TRAC_Human       VEKSFETDTN LNFQNLSVIG FRILLLKVAG FNLLMTLRLW SS SEQ ID NO:31
4L4T_Alpha_Crystal  ---------- ---------- ---------- ---------- -- SEQ ID NO:32

Figure 3A

Constant region sequence of TCR beta chain:

TRBC1_Human      EDLNKVFPPE VAVFEPSEAE ISHTQKATLV CLATGFFPDH VELSWWVNGK
4L4T_Beta_Crystal   EDLKNVFPPE VAVFEPSEAE ISHTQKATLV CLATGFYPDH VELSWWVNGK TRBC1_Human      EVHSGVSTDP QPLKEQPALN DSRYCLSSRL RVSATFWQNP RNHFRCQVQF
4L4T_Beta_Crystal   EVHSGVCTDP QPLKEQPALN DSRYALSSRL RVSATFWQNP RNHFRCQVQF TRBC1_Human      YGLSENDEWT QDRAKPVTQI VSAEAWGRAD CGFTSVSYQQ GVLSATILYE
4L4T_Beta_Crystal   YGLSENDEWT QDRAKPVTQI VSAEAWGRAD ---------- ----------

TRBC1_Human      ILLGKATLYA VLVSALVLMA MVKRKDF-- SEQ ID NO:33
4L4T_Beta_Crystal   ---------- ---------- --------- SEQ ID NO:34

Figure 3B

Numbering Defined for Alpha Constant Region:

```
                        1         11        21        31        50
       TRAC_Human       PNIQNPDPAV YQLRDSKSSD KSVCLFTDFD SQTNVSQSKD SDVYITDKTV
  4L4T_Alpha_Crystal    PDIQNPDPAV YQLRDSKSSD KSVCLFTDFD SQTNVSQSKD SDVYITDKCV
  E17_Design_2_QQQQ_IgG4 PDIQNPDPAV YQLRDSKSSD KSVCLFTDFD SQTQVSQSKD SDVYITDKCV 51        61        71        81        95 SEQ ID NO:
       TRAC_Human       LDMRSMDFKS NSAVAWSNKS DFACANAFNN SIIPEDTFFP SPESS  35
  4L4T_Alpha_Crystal    LDMRSMDFKS NSAVAWSNKS DFACANAFNN SIIPEDTFFP SPESS  36
  E17_Design_2_QQQQ_IgG4 LDMRSMDFKS NSAVAWSQKS DFACANAFQN SIIPEDTFFP SPESS  37
```

Figure 4A

Numbering Defined for Beta Constant Region:.

```
                        0 1       11        21        31        50
       TRBC1_Human      E DLNKVFPPEV AVFEPSEAEI SHTQKATLVC LATGFFPDHV ELSWWVNGKE
  4L4T_Beta_Crystal     LE DLKNVFPPEV AVFEPSEAEI SHTQKATLVC LATGFYPDHV ELSWWVNGKE
  E17_Design_2_QQQQ_IgG4 LE DLKNVFPPEV AVFEPSEAEI SHTQKATLVC LATGFYPDHV ELSWWVNGKE 51        61        71        81        100
       TRBC1_Human      VHSGVSTDPQ PLKEQPALND SRYCLSSRLR VSATFWQNPR NHFRCQVQFY
  4L4T_Beta_Crystal     VHSGVCTDPQ PLKEQPALND SRYALSSRLR VSATFWQNPR NHFRCQVQFY
  E17_Design_2_QQQQ_IgG4 VHSGVCTDPQ PLKEQPALQD SRYALSSRLR VSATFWQNPR NHFRCQVQFY 101       111       124  128 SEQ ID NO:
       TRBC1_Human      GLSENDEWTQ DRAKPVTQIV SAEA WGRA   38
  4L4T_Beta_Crystal     GLSENDEWTQ DRAKPVTQIV SAEA WGRA   39
  E17_Design_2_QQQQ_IgG4 GLSENDEWTQ DRAKPVTQIV SAEA WGRA  40
```

Figure 4B

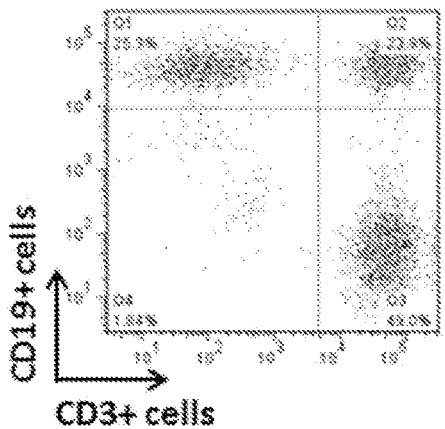 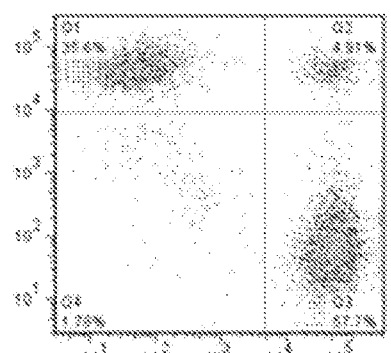
Figure 15AFigure 15B
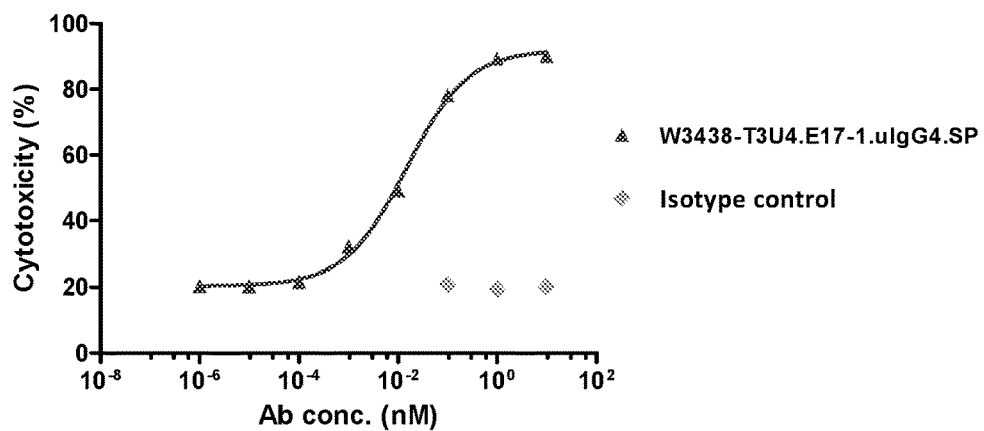
Figure 16A
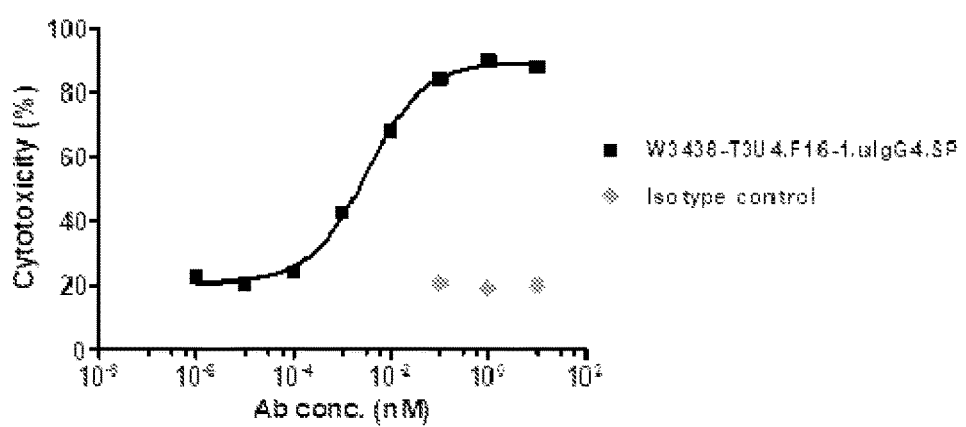
Figure 16B

SEQUENCE LISTING

```
<160> NUMBER OF SEQ ID NOS: 40

<210> SEQ ID NO 1
<211> LENGTH: 116
<212> TYPE: PRT
<213> ORGANISM: artificial sequence
<220> FEATURE:
<223> OTHER INFORMATION: synthetic

<400> SEQUENCE: 1

Glu Val Ala Val Phe Glu Pro Ser Glu Ala Glu Ile Ser His Thr Gln
1               5                   10                  15

Lys Ala Thr Leu Val Cys Leu Ala Thr Gly Phe Tyr Pro Asp His Val
            20                  25                  30

Glu Leu Ser Trp Trp Val Asn Gly Lys Glu Val His Ser Gly Val Cys
        35                  40                  45

Thr Asp Pro Gln Pro Leu Lys Glu Gln Pro Ala Leu Gln Asp Ser Arg
    50                  55                  60

Tyr Ala Leu Ser Ser Arg Leu Arg Val Ser Ala Thr Phe Trp Gln Asn
65                  70                  75                  80

Pro Arg Asn His Phe Arg Cys Gln Val Gln Phe Tyr Gly Leu Ser Glu
                85                  90                  95

Asn Asp Glu Trp Thr Gln Asp Arg Ala Lys Pro Val Thr Gln Ile Val
            100                 105                 110

Ser Ala Glu Ala
        115

<210> SEQ ID NO 2
<211> LENGTH: 87
<212> TYPE: PRT
<213> ORGANISM: artificial sequence
<220> FEATURE:
<223> OTHER INFORMATION: synthetic

<400> SEQUENCE: 2

Ala Val Tyr Gln Leu Arg Asp Ser Lys Ser Ser Asp Lys Ser Val Cys
1               5                   10                  15

Leu Phe Thr Asp Phe Asp Ser Gln Thr Gln Val Ser Gln Ser Lys Asp
            20                  25                  30

Ser Asp Val Tyr Ile Thr Asp Lys Cys Val Leu Asp Met Arg Ser Met
        35                  40                  45

Asp Phe Lys Ser Asn Ser Ala Val Ala Trp Ser Gln Lys Ser Asp Phe
    50                  55                  60

Ala Cys Ala Asn Ala Phe Gln Asn Ser Ile Ile Pro Glu Asp Thr Phe
65                  70                  75                  80
```

Phe Pro Ser Pro Glu Ser Ser
                85

<210> SEQ ID NO 3
<211> LENGTH: 10
<212> TYPE: PRT
<213> ORGANISM: Mus musculus

<400> SEQUENCE: 3

Gly Phe Ala Phe Thr Asp Tyr Tyr Ile His
1               5                   10

<210> SEQ ID NO 4
<211> LENGTH: 17
<212> TYPE: PRT
<213> ORGANISM: Mus musculus

<400> SEQUENCE: 4

Trp Ile Ser Pro Gly Asn Val Asn Thr Lys Tyr Asn Glu Asn Phe Lys
1               5                   10                  15

Gly

<210> SEQ ID NO 5
<211> LENGTH: 10
<212> TYPE: PRT
<213> ORGANISM: Mus musculus

<400> SEQUENCE: 5

Asp Gly Tyr Ser Leu Tyr Tyr Phe Asp Tyr
1               5                   10

<210> SEQ ID NO 6
<211> LENGTH: 17
<212> TYPE: PRT
<213> ORGANISM: Mus musculus

<400> SEQUENCE: 6

Lys Ser Ser Gln Ser Leu Leu Asn Ser Arg Thr Arg Lys Asn Tyr Leu
1               5                   10                  15

Ala

<210> SEQ ID NO 7
<211> LENGTH: 7
<212> TYPE: PRT
<213> ORGANISM: Mus musculus

<400> SEQUENCE: 7

Trp Ala Ser Thr Arg Gln Ser
1               5

<210> SEQ ID NO 8
<211> LENGTH: 8
<212> TYPE: PRT
<213> ORGANISM: Mus musculus

<400> SEQUENCE: 8

Thr Gln Ser His Thr Leu Arg Thr
1               5

<210> SEQ ID NO 9
<211> LENGTH: 10
<212> TYPE: PRT
<213> ORGANISM: Mus musculus

```
<400> SEQUENCE: 9

Gly Tyr Ala Phe Thr Ser Tyr Asn Met Tyr
1               5                   10

<210> SEQ ID NO 10
<211> LENGTH: 17
<212> TYPE: PRT
<213> ORGANISM: artificial sequence
<220> FEATURE:
<223> OTHER INFORMATION: synthetic

<400> SEQUENCE: 10

Tyr Ile Asp Pro Tyr Asn Ala Asp Thr Thr Tyr Asn Gln Lys Phe Lys
1               5                   10                  15

Gly

<210> SEQ ID NO 11
<211> LENGTH: 7
<212> TYPE: PRT
<213> ORGANISM: Mus musculus

<400> SEQUENCE: 11

Thr Ala Tyr Ala Met Asp Tyr
1               5

<210> SEQ ID NO 12
<211> LENGTH: 10
<212> TYPE: PRT
<213> ORGANISM: Mus musculus

<400> SEQUENCE: 12

Ser Ala Ser Ser Thr Val Asn Tyr Met His
1               5                   10

<210> SEQ ID NO 13
<211> LENGTH: 7
<212> TYPE: PRT
<213> ORGANISM: Mus musculus

<400> SEQUENCE: 13

Ser Thr Ser Asn Leu Ala Ser
1               5

<210> SEQ ID NO 14
<211> LENGTH: 9
<212> TYPE: PRT
<213> ORGANISM: Mus musculus

<400> SEQUENCE: 14

His Gln Trp Ser Ser Tyr Pro Tyr Thr
1               5

<210> SEQ ID NO 15
<211> LENGTH: 119
<212> TYPE: PRT
<213> ORGANISM: artificial sequence
<220> FEATURE:
<223> OTHER INFORMATION: synthetic

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ala Phe Thr Asp Tyr
```

```
            20                  25                  30
Tyr Ile His Trp Val Arg Gln Ala Pro Gly Gln Gly Leu Glu Trp Met
        35                  40                  45

Gly Trp Ile Ser Pro Gly Asn Val Asn Thr Lys Tyr Asn Glu Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Ser Leu Tyr Tyr Phe Asp Tyr Trp Gly Gln Gly
            100                 105                 110

Thr Leu Val Thr Val Ser Ser
        115

<210> SEQ ID NO 16
<211> LENGTH: 357
<212> TYPE: DNA
<213> ORGANISM: artificial sequence
<220> FEATURE:
<223> OTHER INFORMATION: synthetic

<400> SEQUENCE: 16
caggtgcagc ttgtgcagtc tggggcagaa gtgaagaagc ctgggtctag tgtcaaggtg     60
tcatgcaagg ctagcgggtt cgcctttact gactactaca tccactgggt gcggcaggct    120
cccggacaag ggttggagtg gatgggatgg atctccccag gcaatgtcaa cacaaagtac    180
aacgagaact tcaaaggccg cgtcaccatt accgccgaca agagcacctc cacagcctac    240
atggagctgt ccagcctcag aagcgaggac actgccgtct actactgtgc agggatggga    300
tactccctgt attactttga ttactggggc cagggcacac tggtgacagt gagctcc       357

<210> SEQ ID NO 17
<211> LENGTH: 112
<212> TYPE: PRT
<213> ORGANISM: artificial sequence
<220> FEATURE:
<223> OTHER INFORMATION: synthetic

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser His Thr Leu Arg Thr Phe Gly Gly Gly Thr Lys Val Glu Ile Lys
            100                 105                 110

<210> SEQ ID NO 18
<211> LENGTH: 336
<212> TYPE: DNA
<213> ORGANISM: artificial sequence
<220> FEATURE:
```

<223> OTHER INFORMATION: synthetic

<400> SEQUENCE: 18

```
gatatcgtga tgacccagag cccagactcc cttgctgtct ccctcggcga aagagcaacc    60
atcaactgca agagctccca aagcctgctg aactccagga ccaggaagaa ttacctggcc   120
tggtatcagc agaagcccgg ccagcctcct aagctgctca tctactgggc ctccacccgg   180
cagtctgggg tgcccgatcg gtttagtgga tctgggagcg ggacagactt cacattgaca   240
attagctcac tgcaggccga ggacgtggcc gtctactact gtactcagag ccacactctc   300
cgcacattcg gcggagggac taaagtggag attaag                             336
```

<210> SEQ ID NO 19
<211> LENGTH: 116
<212> TYPE: PRT
<213> ORGANISM: artificial sequence
<220> FEATURE:
<223> OTHER INFORMATION: synthetic

<400> SEQUENCE: 19

```
Gln Met Gln Leu Val Gln Ser Gly Pro Glu Val Lys Lys Pro Gly Thr
1               5                   10                  15
Ser Val Lys Val Ser Cys Lys Ala Ser Gly Tyr Ala Phe Thr Ser Tyr
            20                  25                  30
Asn Met Tyr Trp Val Arg Gln Ala Arg Gly Gln Arg Leu Glu Trp Ile
        35                  40                  45
Gly Tyr Ile Asp Pro Tyr Asn Ala Asp Thr Thr Tyr Asn Gln Lys Phe
    50                  55                  60
Lys Gly Arg Val Thr Ile Thr Arg Asp Met Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Leu Thr Thr Ala Tyr Ala Met Asp Tyr Trp Gly Gln Gly Thr Leu Val
            100                 105                 110
Thr Val Ser Ser
        115
```

<210> SEQ ID NO 20
<211> LENGTH: 348
<212> TYPE: DNA
<213> ORGANISM: artificial sequence
<220> FEATURE:
<223> OTHER INFORMATION: synthetic

<400> SEQUENCE: 20

```
caaatgcagc tcgtccagtc tggacctgaa gtgaagaagc ccgggacatc cgtcaaggtc    60
tcatgtaagg ctagcgggta cgcattcact tcctacaaca tgtactgggt gcgccaggcc   120
agaggacaga ggttggagtg gatcggctac atcgacccat acaacgccga tactacctac   180
aatcagaagt ttaagggcg gtgaccatt acccgggata tgtccacctc accgcctac     240
atggagctga gcagcctgag gagcgaggac acagccgtgt actactgcct gacaacagcc   300
tatgccatgg actattgggg ccagggcaca cttgtgactg tgagcagt               348
```

<210> SEQ ID NO 21
<211> LENGTH: 106
<212> TYPE: PRT
<213> ORGANISM: artificial sequence
<220> FEATURE:
<223> OTHER INFORMATION: synthetic

<400> SEQUENCE: 21

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Thr Val Asn Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Trp Ser Ser Tyr Pro Tyr Thr
                85                  90                  95

Phe Gly Gln Gly Thr Lys Leu Glu Ile Lys
            100                 105

<210> SEQ ID NO 22
<211> LENGTH: 318
<212> TYPE: DNA
<213> ORGANISM: artificial sequence
<220> FEATURE:
<223> OTHER INFORMATION: synthetic

<400> SEQUENCE: 22

```
gacatccagc tcacccaatc cccttctttc tctccgcaa gtgtcggaga tagggtgact      60
atcacctgct cagcttcttc aaccgtgaac tacatgcatt ggtaccagca gaagcccggg    120
aaagccccaa agctgctgat ctacagcacc tccaatctgg ccagtggagt gccaagccgg    180
tttagcggga gcggctccgg cactgaattc actttgacaa ttagcagcct tcagcctgag    240
gactttgcca catattactg tcaccagtgg tccagctacc cctacacatt cgggcagggc    300
acaaagctgg agattaag                                                  318
```

<210> SEQ ID NO 23
<211> LENGTH: 10
<212> TYPE: PRT
<213> ORGANISM: artificial sequence
<220> FEATURE:
<223> OTHER INFORMATION: synthetic

<400> SEQUENCE: 23

Leu Glu Asp Leu Lys Asn Val Phe Pro Pro
1               5                   10

<210> SEQ ID NO 24
<211> LENGTH: 9
<212> TYPE: PRT
<213> ORGANISM: artificial sequence
<220> FEATURE:
<223> OTHER INFORMATION: synthetic

<400> SEQUENCE: 24

Lys Pro Asp Ile Gln Asn Pro Asp Pro
1               5

<210> SEQ ID NO 25
<211> LENGTH: 17
<212> TYPE: PRT
<213> ORGANISM: artificial sequence
<220> FEATURE:
<223> OTHER INFORMATION: synthetic -continued

<400> SEQUENCE: 25

Tyr Gly Pro Pro Cys Pro Cys Pro Ala Pro Glu Phe Leu Gly Gly
1               5                   10                  15

Pro

<210> SEQ ID NO 26
<211> LENGTH: 207
<212> TYPE: PRT
<213> ORGANISM: artificial sequence
<220> FEATURE:
<223> OTHER INFORMATION: synthetic

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Lys Pro Gly Gln
        35                  40                  45

Pro Pro Lys Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser His Thr Leu Arg Thr Phe Gly Gly Gly Thr Lys Val Glu Ile Lys
            100                 105                 110

Pro Asp Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
    130                 135                 140

Thr Gln Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Gln Lys Ser Asp Phe Ala Cys Ala Asn Ala Phe Gln Asn
            180                 185                 190

Ser Ile Ile Pro Glu Asp Thr Phe Phe Pro Ser Pro Glu Ser Ser
        195                 200                 205

<210> SEQ ID NO 27
<211> LENGTH: 472
<212> TYPE: PRT
<213> ORGANISM: artificial sequence
<220> FEATURE:
<223> OTHER INFORMATION: synthetic

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ala Phe Thr Asp Tyr
                20                  25                  30

Tyr Ile His Trp Val Arg Gln Ala Pro Gly Gln Gly Leu Glu Trp Met
        35                  40                  45

Gly Trp Ile Ser Pro Gly Asn Val Asn Thr Lys Tyr Asn Glu Asn Phe
    50                  55                  60

-continued

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Asp Gly Tyr Ser Leu Tyr Tyr Phe Asp Tyr Trp Gly Gln Gly
         100                 105                 110

Thr Leu Val Thr Val Leu Glu Asp Leu Lys Asn Val Phe Pro Pro Glu
     115                 120                 125

Val Ala Val Phe Glu Pro Ser Glu Ala Glu Ile Ser His Thr Gln Lys
 130                 135                 140

Ala Thr Leu Val Cys Leu Ala Thr Gly Phe Tyr Pro Asp His Val Glu
145                 150                 155                 160

Leu Ser Trp Trp Val Asn Gly Lys Glu Val His Ser Gly Val Cys Thr
             165                 170                 175

Asp Pro Gln Pro Leu Lys Glu Gln Pro Ala Leu Gln Asp Ser Arg Tyr
         180                 185                 190

Ala Leu Ser Ser Arg Leu Arg Val Ser Ala Thr Phe Trp Gln Asn Pro
     195                 200                 205

Arg Asn His Phe Arg Cys Gln Val Gln Phe Tyr Gly Leu Ser Glu Asn
 210                 215                 220

Asp Glu Trp Thr Gln Asp Arg Ala Lys Pro Val Thr Gln Ile Val Ser
225                 230                 235                 240

Ala Glu Ala Trp Gly Arg Tyr Gly Pro Pro Cys Pro Pro Cys Pro Ala
             245                 250                 255

Pro Glu Phe Leu Gly Gly Pro Ser Val Phe Leu Phe Pro Pro Lys Pro
         260                 265                 270

Lys Asp Thr Leu Met Ile Ser Arg Thr Pro Glu Val Thr Cys Val Val
     275                 280                 285

Val Asp Val Ser Gln Glu Asp Pro Glu Val Gln Phe Asn Trp Tyr Val
 290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
             325                 330                 335

Asp Trp Leu Asn Gly Lys Glu Tyr Lys Cys Lys Val Ser Asn Lys Gly
         340                 345                 350

Leu Pro Ser Ser Ile Glu Lys Thr Ile Ser Lys Ala Lys Gly Gln Pro
     355                 360                 365

Arg Glu Pro Gln Val Tyr Thr Leu Pro Pro Cys Gln Glu Glu Met Thr
 370                 375                 380

Lys Asn Gln Val Ser Leu Trp Cys Leu Val Lys Gly Phe Tyr Pro Ser
385                 390                 395                 400

Asp Ile Ala Val Glu Trp Glu Ser Asn Gly Gln Pro Glu Asn Asn Tyr
             405                 410                 415

Lys Thr Thr Pro Pro Val Leu Asp Ser Asp Gly Ser Phe Phe Leu Tyr
         420                 425                 430

Ser Arg Leu Thr Val Asp Lys Ser Arg Trp Gln Glu Gly Asn Val Phe
     435                 440                 445

Ser Cys Ser Val Met His Glu Ala Leu His Asn His Tyr Thr Gln Lys
 450                 455                 460

Ser Leu Ser Leu Ser Leu Gly Lys
465                 470
```

<210> SEQ ID NO 28
<211> LENGTH: 213
<212> TYPE: PRT
<213> ORGANISM: artificial sequence
<220> FEATURE:
<223> OTHER INFORMATION: synthetic

<400> SEQUENCE: 28

```
Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Thr Val Asn Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Trp Ser Ser Tyr Pro Tyr Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 29
<211> LENGTH: 443
<212> TYPE: PRT
<213> ORGANISM: artificial sequence
<220> FEATURE:
<223> OTHER INFORMATION: synthetic

<400> SEQUENCE: 29

```
Gln Met Gln Leu Val Gln Ser Gly Pro Glu Val Lys Lys Pro Gly Thr
1               5                   10                  15

Ser Val Lys Val Ser Cys Lys Ala Ser Gly Tyr Ala Phe Thr Ser Tyr
            20                  25                  30

Asn Met Tyr Trp Val Arg Gln Ala Arg Gly Gln Arg Leu Glu Trp Ile
        35                  40                  45

Gly Tyr Ile Asp Pro Tyr Asn Gly Asp Thr Thr Tyr Asn Gln Lys Phe
    50                  55                  60

Lys Gly Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Leu Thr Thr Ala Tyr Ala Met Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Cys Thr Leu Pro Pro Ser Gln Glu
            340                 345                 350

Glu Met Thr Lys Asn Gln Val Ser Leu Ser Cys Ala Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Val Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 30
<211> LENGTH: 667
<212> TYPE: PRT
<213> ORGANISM: artificial sequence
<220> FEATURE:
<223> OTHER INFORMATION: synthetic

<400> SEQUENCE: 30

Gln Met Gln Leu Val Gln Ser Gly Pro Glu Val Lys Lys Pro Gly Thr
1               5                   10                  15

```
Ser Val Lys Val Ser Cys Lys Ala Ser Gly Tyr Ala Phe Thr Ser Tyr
             20                  25                  30

Asn Met Tyr Trp Val Arg Gln Ala Arg Gly Gln Arg Leu Glu Trp Ile
         35                  40                  45

Gly Tyr Ile Asp Pro Tyr Asn Gly Asp Thr Thr Tyr Asn Gln Lys Phe
     50                  55                  60

Lys Gly Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Leu Thr Thr Ala Tyr Ala Met Asp Tyr Trp Gly Gln Gly Thr Leu Val
             100                 105                 110

Thr Val Ser Ser Ala Ser Thr Lys Gly Pro Ser Val Phe Pro Leu Ala
         115                 120                 125

Pro Cys Ser Arg Ser Thr Ser Glu Ser Thr Ala Ala Leu Gly Cys Leu
     130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                 165                 170                 175

Gly Leu Tyr Ser Leu Ser Ser Val Val Thr Val Pro Ser Ser Ser Leu
             180                 185                 190

Gly Thr Lys Thr Tyr Thr Cys Asn Val Asp His Lys Pro Ser Asn Thr
         195                 200                 205

Lys Val Asp Lys Arg Val Gly Gly Gly Ser Gly Gly Gly Gly Ser
210                 215                 220

Gln Met Gln Leu Val Gln Ser Gly Pro Glu Val Lys Lys Pro Gly Thr
225                 230                 235                 240

Ser Val Lys Val Ser Cys Lys Ala Ser Gly Tyr Ala Phe Thr Ser Tyr
             245                 250                 255

Asn Met Tyr Trp Val Arg Gln Ala Arg Gly Gln Arg Leu Glu Trp Ile
         260                 265                 270

Gly Tyr Ile Asp Pro Tyr Asn Gly Asp Thr Thr Tyr Asn Gln Lys Phe
     275                 280                 285

Lys Gly Arg Val Thr Ile Thr Arg Asp Met Ser Thr Ser Thr Ala Tyr
290                 295                 300

Met Glu Leu Ser Ser Leu Arg Ser Glu Asp Thr Ala Val Tyr Tyr Cys
305                 310                 315                 320

Leu Thr Thr Ala Tyr Ala Met Asp Tyr Trp Gly Gln Gly Thr Leu Val
             325                 330                 335

Thr Val Ser Ser Ala Ser Thr Lys Gly Pro Ser Val Phe Pro Leu Ala
         340                 345                 350

Pro Cys Ser Arg Ser Thr Ser Glu Ser Thr Ala Ala Leu Gly Cys Leu
     355                 360                 365

Val Lys Asp Tyr Phe Pro Glu Pro Val Thr Val Ser Trp Asn Ser Gly
     370                 375                 380

Ala Leu Thr Ser Gly Val His Thr Phe Pro Ala Val Leu Gln Ser Ser
385                 390                 395                 400

Gly Leu Tyr Ser Leu Ser Ser Val Val Thr Val Pro Ser Ser Ser Leu
             405                 410                 415

Gly Thr Lys Thr Tyr Thr Cys Asn Val Asp His Lys Pro Ser Asn Thr
         420                 425                 430

Lys Val Asp Lys Arg Val Glu Ser Lys Tyr Gly Pro Pro Cys Pro Pro
```

```
                    435                 440                 445
Cys Pro Ala Pro Glu Phe Leu Gly Gly Pro Ser Val Phe Leu Phe Pro
    450                 455                 460

Pro Lys Pro Lys Asp Thr Leu Met Ile Ser Arg Thr Pro Glu Val Thr
465                 470                 475                 480

Cys Val Val Val Asp Val Ser Gln Glu Asp Pro Glu Val Gln Phe Asn
                485                 490                 495

Trp Tyr Val Asp Gly Val Glu Val His Asn Ala Lys Thr Lys Pro Arg
            500                 505                 510

Glu Glu Gln Phe Asn Ser Thr Tyr Arg Val Val Ser Val Leu Thr Val
        515                 520                 525

Leu His Gln Asp Trp Leu Asn Gly Lys Glu Tyr Lys Cys Lys Val Ser
    530                 535                 540

Asn Lys Gly Leu Pro Ser Ser Ile Glu Lys Thr Ile Ser Lys Ala Lys
545                 550                 555                 560

Gly Gln Pro Arg Glu Pro Gln Val Cys Thr Leu Pro Pro Ser Gln Glu
                565                 570                 575

Glu Met Thr Lys Asn Gln Val Ser Leu Ser Cys Ala Val Lys Gly Phe
            580                 585                 590

Tyr Pro Ser Asp Ile Ala Val Glu Trp Glu Ser Asn Gly Gln Pro Glu
        595                 600                 605

Asn Asn Tyr Lys Thr Thr Pro Pro Val Leu Asp Ser Asp Gly Ser Phe
    610                 615                 620

Phe Leu Val Ser Arg Leu Thr Val Asp Lys Ser Arg Trp Gln Glu Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Leu Gly Lys
            660                 665

<210> SEQ ID NO 31
<211> LENGTH: 142
<212> TYPE: PRT
<213> ORGANISM: Homo sapiens

<400> SEQUENCE: 31

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140
```

<210> SEQ ID NO 32
<211> LENGTH: 95
<212> TYPE: PRT
<213> ORGANISM: artificial sequence
<220> FEATURE:
<223> OTHER INFORMATION: synthetic

<400> SEQUENCE: 32

```
Pro Asp Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Cys Val Leu Asp Met Arg Ser Met Asp Phe Lys Ser Asn Ser Ala Val
50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser
                85                  90                  95
```

<210> SEQ ID NO 33
<211> LENGTH: 177
<212> TYPE: PRT
<213> ORGANISM: Homo sapiens

<400> SEQUENCE: 33

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

<210> SEQ ID NO 34
<211> LENGTH: 130
<212> TYPE: PRT
<213> ORGANISM: artificial sequence
<220> FEATURE:
<223> OTHER INFORMATION: synthetic

```
<400> SEQUENCE: 34

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Ala Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp
    130

<210> SEQ ID NO 35
<211> LENGTH: 95
<212> TYPE: PRT
<213> ORGANISM: artificial sequence
<220> FEATURE:
<223> OTHER INFORMATION: synthetic

<400> SEQUENCE: 35

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser
                85                  90                  95

<210> SEQ ID NO 36
<211> LENGTH: 95
<212> TYPE: PRT
<213> ORGANISM: artificial sequence
<220> FEATURE:
<223> OTHER INFORMATION: synthetic

<400> SEQUENCE: 36

Pro Asp Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Cys Val Leu Asp Met Arg Ser Met Asp Phe Lys Ser Asn Ser Ala Val
    50                  55                  60
```

```
Ala Trp Ser Asn Lys Ser Asp Phe Ala Cys Ala Asn Ala Phe Asn Asn
 65                  70                  75                  80

Ser Ile Ile Pro Glu Asp Thr Phe Phe Pro Ser Pro Glu Ser Ser
                 85                  90                  95

<210> SEQ ID NO 37
<211> LENGTH: 95
<212> TYPE: PRT
<213> ORGANISM: artificial sequence
<220> FEATURE:
<223> OTHER INFORMATION: synthetic

<400> SEQUENCE: 37

Pro Asp Ile Gln Asn Pro Asp Pro Ala Val Tyr Gln Leu Arg Asp Ser
  1               5                  10                  15

Lys Ser Ser Asp Lys Ser Val Cys Leu Phe Thr Asp Phe Asp Ser Gln
                 20                  25                  30

Thr Gln Val Ser Gln Ser Lys Asp Ser Asp Val Tyr Ile Thr Asp Lys
             35                  40                  45

Cys Val Leu Asp Met Arg Ser Met Asp Phe Lys Ser Asn Ser Ala Val
 50                  55                  60

Ala Trp Ser Gln Lys Ser Asp Phe Ala Cys Ala Asn Ala Phe Gln Asn
 65                  70                  75                  80

Ser Ile Ile Pro Glu Asp Thr Phe Phe Pro Ser Pro Glu Ser Ser
                 85                  90                  95

<210> SEQ ID NO 38
<211> LENGTH: 129
<212> TYPE: PRT
<213> ORGANISM: Homo sapiens

<400> SEQUENCE: 38

Glu Asp Leu Asn Lys Val Phe Pro Pro Glu Val Ala Val Phe Glu Pro
  1               5                  10                  15

Ser Glu Ala Glu Ile Ser His Thr Gln Lys Ala Thr Leu Val Cys Leu
                 20                  25                  30

Ala Thr Gly Phe Phe Pro Asp His Val Glu Leu Ser Trp Trp Val Asn
             35                  40                  45

Gly Lys Glu Val His Ser Gly Val Ser Thr Asp Pro Gln Pro Leu Lys
 50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala

<210> SEQ ID NO 39
<211> LENGTH: 130
<212> TYPE: PRT
<213> ORGANISM: artificial sequence
<220> FEATURE:
<223> OTHER INFORMATION: synthetic

<400> SEQUENCE: 39

Leu Glu Asp Leu Lys Asn Val Phe Pro Pro Glu Val Ala Val Phe Glu
```

```
1               5                   10                  15
Pro Ser Glu Ala Glu Ile Ser His Thr Gln Lys Ala Thr Leu Val Cys
            20                  25                  30

Leu Ala Thr Gly Phe Tyr Pro Asp His Val Glu Leu Ser Trp Trp Val
            35                  40                  45

Asn Gly Lys Glu Val His Ser Gly Val Cys Thr Asp Pro Gln Pro Leu
    50                  55                  60

Lys Glu Gln Pro Ala Leu Asn Asp Ser Arg Tyr Ala Leu Ser Ser Arg
65                  70                  75                  80

Leu Arg Val Ser Ala Thr Phe Trp Gln Asn Pro Arg Asn His Phe Arg
            85                  90                  95

Cys Gln Val Gln Phe Tyr Gly Leu Ser Glu Asn Asp Glu Trp Thr Gln
            100                 105                 110

Asp Arg Ala Lys Pro Val Thr Gln Ile Val Ser Ala Glu Ala Trp Gly
            115                 120                 125

Arg Ala
    130

<210> SEQ ID NO 40
<211> LENGTH: 130
<212> TYPE: PRT
<213> ORGANISM: artificial sequence
<220> FEATURE:
<223> OTHER INFORMATION: synthetic

<400> SEQUENCE: 40

Leu Glu Asp Leu Lys Asn Val Phe Pro Pro Glu Val Ala Val Phe Glu
1               5                   10                  15

Pro Ser Glu Ala Glu Ile Ser His Thr Gln Lys Ala Thr Leu Val Cys
            20                  25                  30

Leu Ala Thr Gly Phe Tyr Pro Asp His Val Glu Leu Ser Trp Trp Val
            35                  40                  45

Asn Gly Lys Glu Val His Ser Gly Val Cys Thr Asp Pro Gln Pro Leu
    50                  55                  60

Lys Glu Gln Pro Ala Leu Gln Asp Ser Arg Tyr Ala Leu Ser Ser Arg
65                  70                  75                  80

Leu Arg Val Ser Ala Thr Phe Trp Gln Asn Pro Arg Asn His Phe Arg
            85                  90                  95

Cys Gln Val Gln Phe Tyr Gly Leu Ser Glu Asn Asp Glu Trp Thr Gln
            100                 105                 110

Asp Arg Ala Lys Pro Val Thr Gln Ile Val Ser Ala Glu Ala Trp Gly
            115                 120                 125

Arg Ala
    130
```

BISPECIFIC CD3/CD19 POLYPEPTIDE COMPLEXES

CROSS-REFERENCE

This application is a national stage entry under 35 U.S.C. § 371 of International Application No. PCT/CN2018/106776, filed Sep. 20, 2018, which claims priority to International Patent Application No. PCT/CN2017/103032, filed Sep. 22, 2017, all of which are incorporated herein by reference.

FIELD OF THE INVENTION

The present disclosure generally relates to bispecific anti-CD3×CD19 polypeptide complexes comprising antibody variable regions fused to the TCR constant regions.

BACKGROUND

Bispecific antibodies are growing to be the new category of therapeutic antibodies. They can bind two different targets or two different epitopes on a target, creating additive or synergistic effect superior to the effect of individual antibodies. A lot of antibody engineering efforts have been put into designing new bispecific formats, such as DVD-Ig, CrossMab, BiTE etc. (Spiess et al., *Molecular Immunology*, 67(2), pp. 95-106 (2015)). However, these formats may potentially have various limitations in stability, solubility, short half-life, and immunogenicity.

Among these bispecific antibody formats, an IgG-like bispecific antibody is a common format: one arm binding to target A and another arm binding to target B. Structurally it is made from half of antibody A and half of antibody B, with the similar size and shape as a natural IgG. In order to facilitate downstream development, it is desired that such bispecific molecules can be easily produced like normal IgG from a single host cell with high expression level and correctly assembled form. Unfortunately, the pairing of cognate light-heavy chains as well as the assembly of two different half antibodies cannot be automatically controlled. All kinds of mispairings in a random manner could result in significant product heterogeneity.

By introducing mutations in the Fc region, such as "knobs-into-holes" (Ridgway et al., *Protein Engineering*, 9(7), pp. 617-21(1996); Merchant et al., *Nature Biotechnology*, 16(7), pp. 677-681(1998)), electrostatics (Gunasekaran et al., *Journal of Biological Chemistry*, 285(25), pp. 19637-19646 (2010)) or negative state designs (Kreudenstein et al., *mAbs*, 5(5), pp. 646-654 (2013); Leaver-Fay et al., *Structure*, 24(4), pp. 641-651 (2016)), the preferred heterodimeric assembly of two different heavy chains has been accomplished. However, the selective pairing of light-heavy chains of each individual antibody remains challenging. The interface between light-heavy chains includes the variable domain (VH-VL) and the constant domain (CH1-CL). Several strategies have been applied into designing orthogonal interfaces to facilitate cognate pairing. Roche swapped the domains of CH1 and CL and created the CrossMab platform (Schaefer et al., *Proceedings of the National Academy of Sciences of the United States of America*, 108(27), pp. 11187-11192 (2011)), MedImmune introduced alternatively disulphide bond (Mazor et al., *mAbs*, 7(2), pp. 377-389 (2015)), Amgen made further electrostatics in the CH1-CL region (Liu et al., *Journal of Biological Chemistry*, 290(12), pp. 7535-7562 (2015)), and Lilly (Lewis et al., *Nature Biotechnology*, 32(2), pp. 191-198 (2014)) and Genentech (Dillon et al., *mAbs*, 9(2), pp. 213-230 (2017)) introduced mutations in both variable and constant domains.

The human CD19 is a type I transmembrane protein belonging to the immunoglobulin superfamily (Carter et al., Curr Dir Autoimmun, 7:4-32 (2004)). It is expressed on most B cells, but not detected on plasma cells, stem cells, or on normal myeloid lineage (Tedder, Nat Rev Rheumatol, 5(10):572-577 (2009)). CD19 is critically involved in establishing intrinsic B cell signaling thresholds through modulating both B cell receptor (BCR)-dependent and independent signaling (Wang et al., Experimental Hematology & Oncology, 1:36 (2012)). CD19 has broader expression than CD20. The pattern of CD19 expression is maintained in B-cell malignancies, covering all subtypes of B-cell lymphoma, from indolent to aggressive forms, as well as B-cell chronic lymphocytic leukemia and non-T acute lymphoblastic leukemia, and allows the targeting of tumor indications of early B cells, such as acute lymphoblastic leukemia (ALL), which cannot be targeted by Rituximab. Several CD19 monoclonal antibodies have been explored for lymphoma therapy (U.S. Patent Application Publication No. 20140072587 A1, U.S. Pat. No. 8,242,252 B2, and U.S. Pat. No. 8,097,703 B2).

The CD3 T-cell co-receptor is a protein complex composed of four distinct chains, a CD3gamma chain, a CD3delta chain, and two CD3epsilon chains. The four chains associate with a molecule known as T-cell receptor (TCR) and the zeta-chain to generate activation signal in T lymphocytes. The TCR, zetachain, and CD3 molecules compose the TCR complex, in which TCR as a subunit recognizes and binds to antigen, and CD3 as a subunit transfers and conveys the antigen stimulation to signaling pathway, and ultimately regulates T-cell activity. The CD3 protein is present in virtually all T cells. The CD3-TCR complex modulates T cell functions in both innate and adoptive immune response, as well as cellular and humoral immune functions. These include eliminating pathogenic organisms and controlling tumor growth by broad range of cytotoxic effects. Mouse monoclonal antibodies specific for human CD3, such as OKT3 (Kung et al., Science, 206: 347-9 (1979)), were the first generation CD3 antibodies developed for treatment. Although OKT3 has strong immunosuppressive potency, its clinical use was hampered by serious side effects linked to its immunogenic and mitogenic potentials (Chatenoud, Nature Reviews, 3:123-132 (2003)). OKT3 induced an anti-globulin response, promoting its own rapid clearance and neutralization (Chatenoud et al., Eur. J. Immunol., 137:830-8 (1982)). In addition, OKT3 induced T-cell proliferation and cytokine production in vitro, and led to a large scale release of cytokine in vivo (Hirsch et al., J. Immunol, 142: 737-43 (1989)). Such serious side effects limited the more widespread use of OKT3 in transplantation as well as the extension of its use to other clinical fields such as autoimmunity.

A bispecific antibody targeting CD3 and CD19 can bind to T cells and B cells simultaneously. Once the bispecific antibody binds to a CD3-positive T cell and a CD19-positive B cell, a cytolytic synapse is formed. Cytotoxicity is then induced by the release of perforin and granzymes from granules in the cytotoxic T cell, the latter inducing apoptosis and lysis of the malignant B cell.

There is great need to design bispecific molecules, with desirable expression level and in vivo half life, to both CD3 and CD19. Such bispecific anti-CD3×CD19 polypeptide complexes are useful for treating CD19-related conditions including cancer.

BRIEF SUMMARY OF THE INVENTION

In one aspect, the present disclosure provides a bispecific polypeptide complex, comprising a first antigen-binding moiety associated with a second antigen-binding moiety, wherein:

the first antigen-binding moiety comprising:

a first polypeptide comprising, from N-terminus to C-terminus, a first heavy chain variable domain (VH1) of a first antibody operably linked to a first T cell receptor (TCR) constant region (C1), and a second polypeptide comprising, from N-terminus to C-terminus, a first light chain variable domain (VL1) of the first antibody operably linked to a second TCR constant region (C2), wherein:

C1 comprises an engineered CBeta comprising SEQ ID NO: 1 and C2 comprises an engineered CAlpha comprising SEQ ID NO: 2, amino acid C48 in SEQ ID NO: 1 and amino acid C41 in SEQ ID NO: 2 are capable of forming a non-native interchain disulphide bond, C1 and C2 are capable of forming a dimer, and the non-native interchain disulphide bond is capable of stabilizing the dimer, and the second antigen-binding moiety comprising:

a second heavy chain variable domain (VH2) of a second antibody operably linked to an antibody heavy chain CH1 domain, and a second light chain variable domain (VL2) of the second antibody operably linked to an antibody light chain constant (CL) domain, wherein:

one of the first and the second antigen-binding moiety is an anti-CD3 binding moiety, and the other one is an anti-CD19 binding moiety, the anti-CD3 binding moiety is derived from an anti-CD3 antibody comprising:

a) a heavy chain CDR1 comprising SEQ ID NO: 3, b) a heavy chain CDR2 comprising SEQ ID NO: 4, c) a heavy chain CDR3 comprising SEQ ID NO: 5, d) a kappa light chain CDR1 comprising SEQ ID NO: 6, e) a kappa light chain CDR2 comprising SEQ ID NO: 7, and f) a kappa light chain CDR3 comprising SEQ ID NO: 8, the anti-CD19 binding moiety is derived from an anti-CD19 antibody comprising:

a) a heavy chain CDR1 comprising SEQ ID NO: 9, b) a heavy chain CDR2 comprising SEQ ID NO: 10, c) a heavy chain CDR3 comprising SEQ ID NO: 11, d) a kappa light chain CDR1 comprising SEQ ID NO: 12, e) a kappa light chain CDR2 comprising SEQ ID NO: 13, and f) a kappa light chain CDR3 comprising SEQ ID NO: 14, and the first antigen-binding moiety and the second antigen-binding moiety are less prone to mispair than otherwise would have been if both the first and the second antigen-binding moieties are counterparts of natural Fab.

In certain embodiments, the anti-CD3 binding moiety of the bispecific polypeptide complex is derived from an anti-CD3 antibody comprising a heavy chain variable domain sequence comprising SEQ ID NO: 15 and a light chain variable domain sequence comprising SEQ ID NO: 17.

In certain embodiments, the anti-CD19 binding moiety of the bispecific polypeptide complex is derived from an anti-CD19 antibody comprising a heavy chain variable domain sequence comprising SEQ ID NO: 19 and a light chain variable domain sequence comprising SEQ ID NO: 21.

In certain embodiments, the bispecific polypeptide complex comprises a combination of four polypeptide sequences: SEQ ID NO: 26, SEQ ID NO: 27, SEQ ID NO: 28, and SEQ ID NO: 29.

In certain embodiments, the bispecific polypeptide complex comprises a combination of four polypeptide sequences: SEQ ID NO: 26, SEQ ID NO: 27, SEQ ID NO: 28, and SEQ ID NO: 30.

In one aspect, the present disclosure provides herein a conjugate comprising the bispecific polypeptide complex provided herein conjugated to a moiety.

In one aspect, the present disclosure provides herein an isolated polynucleotide encoding the bispecific polypeptide complex provided herein.

In one aspect, the present disclosure provides herein an isolated vector comprising the polynucleotide provided herein.

In one aspect, the present disclosure provides herein a host cell comprising the isolated polynucleotide provided herein or the isolated vector provided herein.

In one aspect, the present disclosure provides herein a method of expressing the bispecific polypeptide complex provided herein, comprising culturing the host cell provided herein under the condition at which the bispecific polypeptide complex is expressed.

In one aspect, the present disclosure provides a composition comprising the bispecific polypeptide complex provided herein.

In one aspect, the present disclosure provides herein a pharmaceutical composition comprising the bispecific polypeptide complex provided herein and a pharmaceutically acceptable carrier.

In one aspect, the present disclosure provides herein a method of treating a CD19-related disease or condition in a subject in need thereof, comprising administrating to the subject a therapeutically effective amount of the bispecific polypeptide complex provided herein. In certain embodiments, the disease or condition can be alleviated, eliminated, treated, or prevented when the first antigen and the second antigen are both modulated.

In certain embodiments, the first VH is operably linked to CBeta at a first conjunction domain, which comprises a C terminal fragment of antibody V/C conjunction and has the amino acid sequence of SEQ ID NO: 23 (LEDLKNVFPP), and the first VL is operably linked to CAlpha at a second conjunction domain, which comprises a N terminal fragment of TCR V/C conjunction and has the amino acid sequence of SEQ ID NO: 24 (KPDIQNPDP).

In certain embodiments, the first antigen-binding moiety is linked to a first dimerization domain, and the second antigen-binding moiety is linked to a second dimerization domain, wherein the first and the second dimerization domains are associated. In certain embodiments, the association is via a connecter, a disulphide bond, a hydrogen bond, electrostatic interaction, a salt bridge, or hydrophobic-hydrophilic interaction, or the combination thereof.

In certain embodiments, the first and/or the second dimerization domain comprises at least a portion of an antibody hinge region, optionally derived from IgG1, IgG2 or IgG4.

In certain embodiments, C1 comprises an engineered CBeta, and the first dimerization domain is operably linked to the engineered CBeta at a third conjunction domain, which comprises SEQ ID NO: 25 (YGPPCPPCPAPEFLGGP).

In certain embodiments, the second dimerization domain is operably linked to the heavy chain variable domain of the second antigen-binding moiety.

In certain embodiments, the first and the second dimerization domains are different and associate in a way that discourages homodimerization and/or favors heterodimerization.

In certain embodiments, the first and the second dimerization domains are capable of associating into heterodimers via knobs-into-holes, hydrophobic interaction, electrostatic interaction, hydrophilic interaction, or increased flexibility.

In another aspect, the present disclosure provides a kit comprising the polypeptide complex provided herein for detection, diagnosis, prognosis, or treatment of a disease or condition.

The foregoing and other features and advantages of the invention will become more apparent from the following detailed description of several embodiments which proceeds with reference to the accompanying figures.

BRIEF DESCRIPTION OF FIGURES

FIG. 2A presents an antibody Fv structure model that was built based on the sequence of an anti-CD3 antibody T3 developed in-house. FIG. 2B presents the TCR structure from PDB 4L4T. FIG. 2C presents an antibody Fv structural model superimposed on the TCR variable region in different orientations. Rough chimeric proteins were created by removing the TCR variable domain in the superimposed poses, as shown in FIG. 2D. The overlapped residues in the conjunction area helped design conjunction region. The antibody VL chain and the TCR alpha chain were colored in white. The VH and beta chains were colored in black.

FIG. 3A shows the sequence of native TCR alpha chain and its counterpart sequence with mutated cysteine residues. TRAC_Human is a natural sequence of alpha chain constant region. 4L4T_Alpha_Crystal is the sequence of a crystal structure (PDB code 4L4T) with S55C mutations that can form inter-chain disulphide bond. The gray region is the constant region used as backbone of chimeric protein in this invention.

FIG. 3B shows the sequence of native TCR beta chain and its counterpart sequence with mutated cysteine residues.

FIGS. 4A-4B show the sequences and numbering of the TCR CAlpha and CBeta constant regions with removed N-glycosylation. FIG. 4A shows the sequences and numbering of the TCR Alpha constant region. FIG. 4B shows the sequences and numbering of the TCR Beta constant region.

FIGS. 15A-15B show dual binding of W3438-T3U4.E17-1.uIgG4.SP to CD19 and CD3 (FIG. 15A); and a negative control (FIG. 15B).

FIGS. 16A-16B show cytotoxic activity of W3438-T3U4.E17-1.uIgG4.SP on Raji cells (FIG. 16A) and cytotoxic activity of W3438-T3U4.F16-1.uIgG4.SP on Raji cells (FIG. 16B).

DETAILED DESCRIPTION OF THE INVENTION

Figure 1:
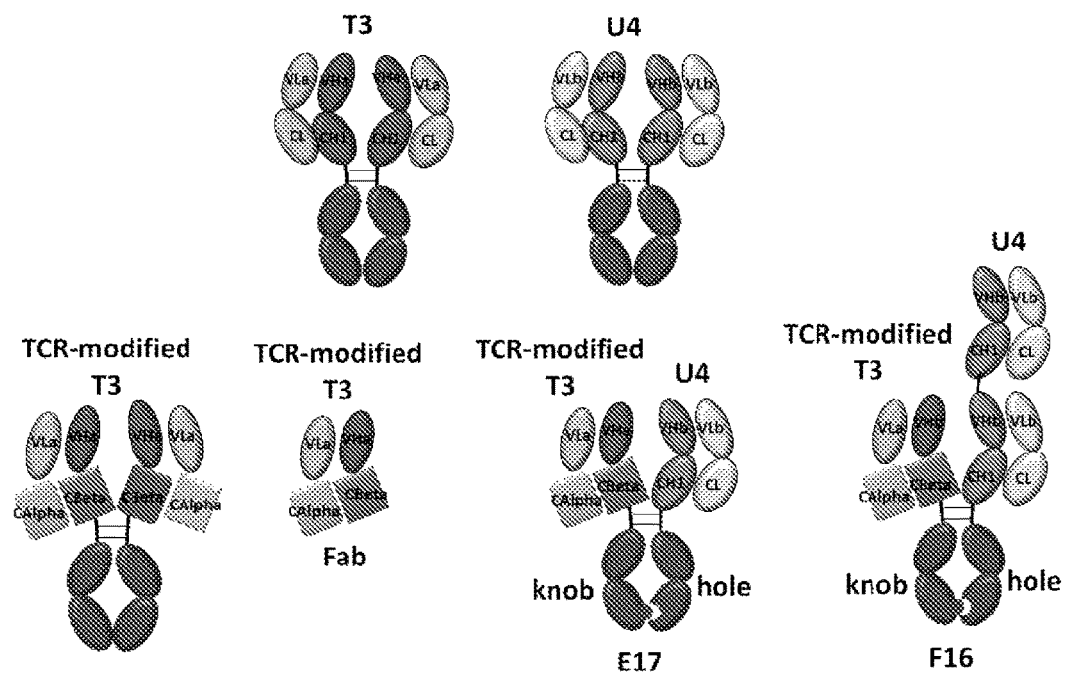
FIG. 1 presents schematic representations of studied antibody formats. Both anti-CD3 antibody T3 and anti-CD19 antibody U4 were developed. The constant region (CL and CH1) of T3 was replaced by the constant domains of TCR to design unique light-heavy chain interface that is orthogonal to regular antibody. The TCR-modified T3 and native U4 in conjunction with "knobs-into-holes" mutations in Fc domain were used to design bispecific antibody formats E17 and F16.

The following description of the disclosure is merely intended to illustrate various embodiments of the disclosure.

Definitions

The articles "a," "an," and "the" are used herein to refer to one or to more than one (i.e., to at least one) of the grammatical object of the article. By way of example, "a polypeptide complex" means one polypeptide complex or more than one polypeptide complex.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Throughout this disclosure, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Reference throughout this disclosure to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

The terms "polypeptide," "peptide," and "protein" are used interchangeably herein to refer to a polymer of amino acid residues, or an assembly of multiple polymers of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refer to compounds that have the same basic chemical structure as a naturally occurring amino acid, i.e., an alpha-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. An alpha-carbon refers to the first carbon atom that attaches to a functional group, such as a carbonyl. A beta-carbon refers to the second carbon atom linked to the alpha-carbon, and the system continues naming the carbons in alphabetical order with Greek letters. Amino acid mimetics refers to chemical compounds that have a structure that is different from the general chemical structure of an amino acid, but that functions in a manner similar to a naturally occurring amino acid. The term "protein" typically refers to large polypeptides. The term "peptide" typically refers to short polypeptides. Polypeptide sequences are usually described as the left-hand end of a polypeptide sequence is the amino-terminus (N-terminus); the right-hand end of a polypeptide sequence is the carboxyl-terminus (C-terminus). "Polypeptide complex" as used herein refers to a complex comprising one or more polypeptides that are associated to perform certain functions. In certain embodiments, the polypeptides are immune-related.

The term "antibody" as used herein encompasses any immunoglobulin, monoclonal antibody, polyclonal antibody, multispecific antibody, or bispecific (bivalent) antibody that binds to a specific antigen. A native intact antibody comprises two heavy chains and two light chains. Each heavy chain consists of a variable region ("HCVR") and a first, second, and third constant region (CH1, CH2 and CH3), while each light chain consists of a variable region ("LCVR") and a constant region (CL). Mammalian heavy chains are classified as $\alpha$, $\delta$, $\epsilon$, $\gamma$, and $\mu$, and mammalian light chains are classified as $\lambda$, or $\kappa$. The antibody has a "Y" shape, with the stem of the Y consisting of the second and third constant regions of two heavy chains bound together via disulphide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for antibodies may be defined or identified by the conventions of Kabat, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 342(6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. Each HCVR and LCVR comprises four FRs, and the CDRs and FRs are arranged from amino terminus to carboxy terminus in the order: FR1, CDR1, FR2, CDR2, FR3, CDR3, FR4. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and µ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (al heavy chain), or IgA2 (α2 heavy chain).

The term "variable domain" with respect to an antibody as used herein refers to an antibody variable region or a fragment thereof comprising one or more CDRs. Although a variable domain may comprise an intact variable region (such as HCVR or LCVR), it is also possible to comprise less than an intact variable region yet still retain the capability of binding to an antigen or forming an antigen-binding site.

The term "antigen-binding moiety" as used herein refers to an antibody fragment formed from a portion of an antibody comprising one or more CDRs, or any other antibody fragment that binds to an antigen but does not comprise an intact native antibody structure. Examples of antigen-binding moiety include, without limitation, a variable domain, a variable region, a diabody, a Fab, a Fab', a F(ab)$_2$, an Fv fragment, a disulphide stabilized Fv fragment (dsFv), a (dsFv)$_2$, a bispecific dsFv (dsFv-dsFv'), a disulphide stabilized diabody (ds diabody), a multispecific antibody, a camelized single domain antibody, a nanobody, a domain antibody, and a bivalent domain antibody. An antigen-binding moiety is capable of binding to the same antigen to which the parent antibody binds. In certain embodiments, an antigen-binding moiety may comprise one or more CDRs from a particular human antibody grafted to a framework region from one or more different human antibodies. For more and detailed formats of antigen-binding moiety are described in Spiess et al, 2015 (Supra), and Brinkman et al., *mAbs,* 9(2), pp. 182-212 (2017), which are incorporated herein by their entirety.

"Fab" with regard to an antibody refers to that portion of the antibody consisting of a single light chain (both variable and constant regions) associating to the variable region and first constant region of a single heavy chain by a disulphide bond. In certain embodiments, the constant regions of both the light chain and heavy chain are replaced with TCR constant regions.

"Fab" refers to a Fab fragment that includes a portion of the hinge region.

"F(ab')$_2$" refers to a dimer of Fab'.

A "fragment difficult (Fd)" with regard to an antibody refers to the amino-terminal half of the heavy chain fragment that can be combined with the light chain to form Fab.

"Fc" with regard to an antibody refers to that portion of the antibody consisting of the second (CH2) and third (CH3) constant regions of a first heavy chain bound to the second and third constant regions of a second heavy chain via disulphide bonding. The Fc portion of the antibody is responsible for various effector functions such as ADCC, and CDC, but does not function in antigen binding.

"Hinge region" in terms of an antibody includes the portion of a heavy chain molecule that joins the CH1 domain to the CH2 domain. This hinge region comprises approximately 25 amino acid residues and is flexible, thus allowing the two N-terminus antigen binding regions to move independently.

"CH2 domain" as used herein refers to includes the portion of a heavy chain molecule that extends, e.g., from about amino acid 244 to amino acid 360 of an IgG antibody using conventional numbering schemes (amino acids 244 to 360, Kabat numbering system; and amino acids 231-340, EU numbering system; see Kabat, E., et al., U.S. Department of Health and Human Services, (1983)).

The "CH3 domain" extends from the CH2 domain to the C-terminus of the IgG molecule and comprises approximately 108 amino acids. Certain immunoglobulin classes, e.g., IgM, further include a CH4 region.

"Fv" with regard to an antibody refers to the smallest fragment of the antibody to bear the complete antigen binding site. An Fv fragment consists of the variable domain of a single light chain bound to the variable domain of a single heavy chain. A number of Fv designs have been provided, including dsFvs, in which the association between the two domains is enhanced by an introduced disulphide bond; and scFvs can be formed using a peptide linker to bind the two domains together as a single polypeptide. Fvs constructs containing a variable domain of a heavy or light immunoglobulin chain associated to the variable and constant domain of the corresponding immunoglobulin heavy or light chain have also been produced. Fvs have also been multimerised to form diabodies and triabodies (Maynard et al., Annu Rev Biomed Eng 2 339-376 (2000)).

"ScFab" refers to a fusion polypeptide with a Fd linked to a light chain via a polypeptide linker, resulting in the formation of a single chain Fab fragment (scFab).

"TriFabs" refers to a trivalent, bispecific fusion protein composed of three units with Fab-functionalities. TriFabs harbor two regular Fabs fused to an asymmetric Fab-like moiety.

"Fab-Fab" refers to a fusion protein formed by fusing the Fd chain of a first Fab arm to the N-terminus of the Fd chain of a second Fab arm.

"Fab-Fv" refers to a fusion protein formed by fusing a HCVR to the C-terminus of a Fd chain and a LCVR to the C-terminus of a light chain. A "Fab-dsFv" molecule can be formed by introducing an interdomain disulphide bond between the HCVR domain and the LCVR domain.

"MAb-Fv" or "IgG-Fv" refers to a fusion protein formed by fusion of HCVR domain to the C-terminus of one Fc chain and the LCVR domain either expressed separately or fused to the C-terminus of the other resulted in a bispecific, trivalent IgG-Fv (mAb-Fv) fusion protein, with the Fv stabilized by an interdomain disulphide bond.

"ScFab-Fc-scFv$_2$" and "ScFab-Fc-scFv" refer to a fusion protein formed by fusion of a single-chain Fab with Fc and disulphide-stabilized Fv domains.

"Appended IgG" refers to a fusion protein with a Fab arm fused to an IgG to form the format of bispecific (Fab)$_2$-Fc. It can form a "IgG-Fab" or a "Fab-IgG", with a Fab fused to the C-terminus or N-terminus of an IgG molecule with or without a connector. In certain embodiments, the appended IgG can be further modified to a format of IgG-Fab$_4$ (see, Brinkman et al., 2017, Supra).

"DVD-Ig" refers to a dual-variable-domain antibody that is formed by fusion of an additional HCVR domain and LCVR domain of a second specificity to an IgG heavy chain and light chain. "CODV-Ig" refers to a related format where the two HCVR and two LCVR domains are linked in a way that allows crossover pairing of the variable HCVR-LCVR domains, which are arranged either (from N- to C-terminus) in the order HCVRA-HCVRB and LCVRB-LCVRA, or in the order HCVRB-HCVRA and LCVRA-LCVRB.

A "CrossMab" refers to a technology of pairing of unmodified light chain with the corresponding unmodified heavy chain and pairing of the modified light chain with the corresponding modified heavy chain, thus resulting an antibody with reduced mispairing in the light chain.

A "BiTE" is a bispecific T-cell engager molecule, comprising a first scFv with a first antigen specificity in the LCVR-HCVR orientation linked to a second scFv with a second specificity in the HCVR-LCVR orientation.

A "WuXiBody" is a bispecific antibody comprising soluble chimeric protein with variable domains of an antibody and the constant domains of TCR, wherein the subunits (such as alpha and beta domains) of TCR constant domains are linked by engineered disulfide bond.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al., J. Mol. Biol., 215:403-410 (1990); Stephen F. et al., Nucleic Acids Res., 25:3389-3402 (1997)), ClustalW2 (available on the website of European Bioinformatics Institute, see also, Higgins D. G. et al., Methods in Enzymology, 266:383-402 (1996); Larkin M. A. et al., Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

An "antigen" or "Ag" as used herein refers to a compound, composition, peptide, polypeptide, protein or substance that can stimulate the production of antibodies or a T cell response in cell culture or in an animal, including compositions (such as one that includes a cancer-specific protein) that are added to a cell culture (such as a hybridoma), or injected or absorbed into an animal. An antigen reacts with the products of specific humoral or cellular immunity (such as an antibody), including those induced by heterologous antigens.

An "epitope" or "antigenic determinant" refers to the region of an antigen to which a binding agent (such as an antibody) binds. Epitopes can be formed both from contiguous amino acids (also called linear or sequential epitope) or noncontiguous amino acids juxtaposed by tertiary folding of a protein (also called configurational or conformational epitope). Epitopes formed from contiguous amino acids are typically arranged linearly along the primary amino acid residues on the protein and the small segments of the contiguous amino acids can be digested from an antigen binding with major histocompatibility complex (MEW) molecules or retained on exposure to denaturing solvents whereas epitopes formed by tertiary folding are typically lost on treatment with denaturing solvents. An epitope typically includes at least 3, and more usually, at least 5, about 7, or about 8-10 amino acids in a unique spatial conformation.

The term "specific binding" or "specifically binds" as used herein refers to a non-random binding reaction between two molecules, such as for example between an antibody and an antigen. In certain embodiments, the polypeptide complex and the bispecific polypeptide complex provided herein specifically bind an antigen with a binding affinity ($K_D$) of $\leq 10^{-6}$ M (e.g., $\leq 5 \times 10^{-7}$M, $\leq 2 \times 10^{-7}$M, $\leq 10^{-7}$ M, $\leq 5 \times 10^{-8}$M, $\leq 2 \times 10^{-8}$ M, $\leq 10^{-8}$M, $\leq 5 \times 10^{-9}$M, $\leq 2 \times 10^{-9}$ M, $\leq 10^{-9}$ M, or $\leq 10^{-10}$ M). $K_D$ as used herein refers to the ratio of the dissociation rate to the association rate ($k_{off}/k_{on}$), may be determined using surface plasmon resonance methods for example using instrument such as Biacore.

The term "operably link" or "operably linked" refers to a juxtaposition, with or without a spacer or linker, of two or more biological sequences of interest in such a way that they are in a relationship permitting them to function in an intended manner. When used with respect to polypeptides, it is intended to mean that the polypeptide sequences are linked in such a way that permits the linked product to have the intended biological function. For example, an antibody variable region may be operably linked to a constant region so as to provide for a stable product with antigen-binding activity. The term may also be used with respect to polynucleotides. For one instance, when a polynucleotide encoding a polypeptide is operably linked to a regulatory sequence (e.g., promoter, enhancer, silencer sequence, etc.), it is intended to mean that the polynucleotide sequences are linked in such a way that permits regulated expression of the polypeptide from the polynucleotide.

The term "fusion" or "fused" when used with respect to amino acid sequences (e.g. peptide, polypeptide or protein) refers to combination of two or more amino acid sequences, for example by chemical bonding or recombinant means, into a single amino acid sequence which does not exist naturally. A fusion amino acid sequence may be produced by genetic recombination of two encoding polynucleotide sequences, and can be expressed by a method of introducing a construct containing the recombinant polynucleotides into a host cell.

The term "spacer" as used herein refers to an artificial amino acid sequence having 1, 2, 3, 4 or 5 amino acid residues, or a length of between 5 and 15, 20, 30, 50 or more amino acid residues, joined by peptide bonds and are used to link one or more polypeptides. A spacer may or may not have a secondary structure. Spacer sequences are known in the art, see, for example, Holliger et al., Proc. Natl. Acad. Sci. USA 90:6444-6448 (1993); Poljak et al., Structure 2:1121-1123 (1994). Any suitable spacers known in the art can be used.

The term "antigenic specificity" refers to a particular antigen or an epitope thereof that is selectively recognized by an antigen-binding molecule.

The term "substitution" with regard to amino acid residue as used herein refers to naturally occurring or induced replacement of one or more amino acids with another in a peptide, polypeptide or protein. Substitution in a polypeptide may result in diminishment, enhancement, or elimination of the polypeptide's function.

Substitution can also be "conservative substitution" with reference to amino acid sequence refers to replacing an amino acid residue with a different amino acid residue having a side chain with similar physiochemical properties or substitution of those amino acids that are not critical to the activity of the polypeptide. For example, conservative substitutions can be made among amino acid residues with nonpolar side chains (e.g., Met, Ala, Val, Leu, and Ile, Pro, Phe, Trp), among residues with uncharged polar side chains (e.g., Cys, Ser, Thr, Asn, Gly and Gln), among residues with acidic side chains (e.g. Asp, Glu), among amino acids with basic side chains (e.g., His, Lys, and Arg), among amino acids with beta-branched side chains (e.g., Thr, Val and Ile), among amino acids with sulfur-containing side chains (e.g., Cys and Met), or among residues with aromatic side chains (e.g., Trp, Tyr, His and Phe). In certain embodiments, substitutions, deletions or additions can also be considered as "conservative substitution". The number of amino acids that are inserted or deleted can be in the range of about 1 to 5. Conservative substitution usually does not cause significant change in the protein conformational structure, and therefore could retain the biological activity of a protein.

The term "mutation" or "mutated" with regard to amino acid residue as used herein refers to substitution, insertion, or addition of an amino acid residue.

"T cell" as used herein refers to a type of lymphocyte that plays a critical role in the cell-mediated immunity, including helper T cells (e.g. CD4+ T cells, T helper 1 type T cells, T helper 2 type T cells, T helper 3 type T cells, T helper 17 type T cells), cytotoxic T cells (e.g. CD8+ T cells), memory T cells (e.g. central memory T cells (TCM cells), effector memory T cells (TEM cells and TEMRA cells) and resident memory T cells (TRM) that are either CD8+ or CD4+), natural killer T (NKT) cells and inhibitory T cells.

A native "T cell receptor" or a native "TCR" is a heterodimeric T cell surface protein which is associated with invariant CD3 chains to form a complex capable of mediating signal transduction. TCR belongs to the immunoglobulin superfamily, and is similar to a half antibody with a single heavy chain and a single light chain. Native TCR has an extracellular portion, a transmembrane portion and an intracellular portion. The extracellular domain of a TCR has a membrane-proximal constant region and a membrane-distal variable region.

The term "subject" or "individual" or "animal" or "patient" as used herein refers to human or non-human animal, including a mammal or a primate, in need of diagnosis, prognosis, amelioration, prevention and/or treatment of a disease or disorder. Mammalian subjects include humans, domestic animals, farm animals, and zoo, sports, or pet animals such as dogs, cats, guinea pigs, rabbits, rats, mice, horses, swine, cows, bears, and so on.

Bispecific Polypeptide Complex

In one aspect, the present disclosure provides herein a bispecific polypeptide complex. The term "bispecific" as used herein means that there are two antigen-binding moieties, each of which is capable of specifically binding to a different antigen or a different epitope on the same antigen. The bispecific polypeptide complex provided herein comprises a first antigen-binding moiety associated with a second antigen-binding moiety, and one of them specifically binds to CD3, and the other specifically binds to CD19. In other words, the first antigen-binding moiety may specifically bind to CD3 and the second antigen-binding moiety may specifically bind to CD19. Alternatively, the first antigen-binding moiety may specifically bind to CD19 and the second antigen-binding moiety may specifically bind to CD3.

In certain embodiments, the present disclosure provides a bispecific polypeptide complex, comprising a first antigen-binding moiety associated with a second antigen-binding moiety, wherein:
the first antigen-binding moiety comprising:
a first polypeptide comprising, from N-terminus to C-terminus, a first heavy chain variable domain (VH1) of a first antibody operably linked to a first T cell receptor (TCR) constant region (C1), and
a second polypeptide comprising, from N-terminus to C-terminus, a first light chain variable domain (VL1) of the first antibody operably linked to a second TCR constant region (C2), wherein:
C1 comprises an engineered CBeta comprising SEQ ID NO: 1 and C2 comprises an engineered CAlpha comprising SEQ ID NO: 2,
amino acid C48 in SEQ ID NO: 1 and amino acid C41 in SEQ ID NO: 2 are capable of forming a non-native interchain disulphide bond,
C1 and C2 are capable of forming a dimer, and the non-native interchain disulphide bond is capable of stabilizing the dimer,
and
the second antigen-binding moiety comprising:
a second heavy chain variable domain (VH2) of a second antibody operably linked to an antibody heavy chain CH1 domain, and
a second light chain variable domain (VL2) of the second antibody operably linked to an antibody light chain constant (CL) domain,
wherein:
one of the first and the second antigen-binding moiety is an anti-CD3 binding moiety, and the other one is an anti-CD19 binding moiety,
the anti-CD3 binding moiety is derived from an anti-CD3 antibody comprising:
a) a heavy chain CDR1 comprising SEQ ID NO: 3, b) a heavy chain CDR2 comprising SEQ ID NO: 4, c) a heavy chain CDR3 comprising SEQ ID NO: 5, d) a kappa light chain CDR1 comprising SEQ ID NO: 6, e) a kappa light chain CDR2 comprising SEQ ID NO: 7, and f) a kappa light chain CDR3 comprising SEQ ID NO: 8, the anti-CD19 binding moiety is derived from an anti-CD19 antibody comprising:
a) a heavy chain CDR1 comprising SEQ ID NO: 9, b) a heavy chain CDR2 comprising SEQ ID NO: 10, c) a heavy chain CDR3 comprising SEQ ID NO: 11, d) a kappa light chain CDR1 comprising SEQ ID NO: 12, e) a kappa light chain CDR2 comprising SEQ ID NO: 13, and f) a kappa light chain CDR3 comprising SEQ ID NO: 14,
and
the first antigen-binding moiety and the second antigen-binding moiety are less prone to mispair than otherwise would have been if both the first and the second antigen-binding moieties are counterparts of natural Fab.

In certain embodiments, the bispecific polypeptide complex provided herein comprises a first antigen-binding moiety containing a sequence derived from a TCR constant region but the second antigen-binding moiety does not contain a sequence derived from a TCR constant region.

The bispecific polypeptide complex provided herein is significantly less prone to have mispaired heavy chain and light chain variable domains. Without wishing to be bound by any theory, it is believed that the stabilized TCR constant regions in the first antigen-binding moiety can specifically associate with each other and therefore contribute to the highly specific pairing of the intended VH1 and VL1, while discouraging unwanted mispairings of VH1 or VL1 with other variable regions that do not provide for the intended antigen-binding sites.

In certain embodiments, the second antigen-binding moiety further comprises an antibody constant CH1 domain operably linked to VH2, and an antibody light chain constant domain operably linked to VL2. Thus, the second antigen-binding moiety comprises a Fab.

Where the first, second, third, and fourth variable domains (e.g. VH1, VH2, VL1 and VL2) are expressed in one cell, it is highly desired that VH1 specifically pairs with VL1, and VH2 specifically pairs with VL2, such that the resulting bispecific protein product would have the correct antigen-binding specificities. However, in existing technologies such as hybrid-hybridoma (or quadroma), random pairing of VH1, VH2, VL1 and VL2 occurs and consequently results in generation of up to ten different species, of which only one is the functional bispecific antigen-binding molecule. This not only reduces production yields but also complicates the purification of the target product.

The bispecific polypeptide complexes provided herein are exceptional in that the variable domains are less prone to mispair than otherwise would have been if both the first and the second antigen-binding moieties are counterparts of natural Fab. In an illustrative example, the first antigen-binding domain comprises VH1-C1 paired with VL1-C2, and the second antigen-binding domain comprises VH2-CH1 paired with VL2-CL. It has been surprisingly found that C1 and C2 preferentially associates with each other, and are less prone to associate with CL or CH1, thereby formation of unwanted pairs such as C1-CH, C1-CL, C2-CH, and C2-CL are discouraged and significantly reduced. As a result of specific association of C1-C2, VH1 specifically pairs with VL1, thereby rendering the first antigen binding site, and CH1 specifically pairs with CL, thereby allowing specific pairing of VH2-VL2 which provides for the second antigen binding site. Accordingly, the first antigen binding moiety and the second antigen binding moiety are less prone to mismatch, and mispairings between for example VH1-VL2, VH2-VL1, VH1-VH2, VL1-VL2 are significantly reduced than otherwise could have been if both the first and the second antigen-binding moieties are counterparts of natural Fabs, e.g. in the form of VH1-CH1, VL1-CL, VH2-CH1, and VL2-CL.

In certain embodiments, the bispecific polypeptide complex provided herein, when expressed from a cell, has significantly less mispairing products (e.g., at least 1, 2, 3, 4, 5 or more mispairing products less) and/or significantly higher production yield (e.g., at least 10%, 20%, 30%, 40%, 50%, 60% or more higher yield), than a reference molecule expressed under comparable conditions, wherein the reference molecule is otherwise identical to the bispecific polypeptide complex except having a native CH1 in the place of C1 and a native CL in the place of C2.

Antigen-Binding Moiety Comprising Engineered CAlpha and CBeta

The first antigen-binding moiety provided herein comprises a first antibody heavy chain variable domain operably linked to a first T cell receptor (TCR) constant region, and a first antibody light chain variable domain operably linked to a second TCR constant region, wherein the first TCR constant region and the second TCR constant region are associated via at least one non-native interchain disulphide bond. The first antigen-binding moiety comprises at least two polypeptide chains, each of which comprises a variable domain derived from an antibody and a constant region derived from a TCR. Thus, the first antigen-binding moiety comprises a heavy chain variable domain and a light chain variable domain, which are operably linked to a pair of TCR constant regions, respectively. In certain embodiments, the pair of TCR constant regions in the first antigen-binding moiety are alpha/beta TCR constant regions. The TCR constant regions in the polypeptide complexes provided herein are capable of associating with each other to form a dimer through at least one non-native disulphide bond.

It is surprisingly found that the first antigen-binding moiety provided herein with at least one non-native disulphide bond can be recombinantly expressed and assembled into the desired conformation, which stabilizes the TCR constant region dimer while providing for good antigen-binding activity of the antibody variable regions. Moreover, the first antigen-binding moiety is found to well tolerate routine antibody engineering, for example, modification of glycosylation sites, and removal of some natural sequences. Furthermore, the polypeptide complexes provided herein can be incorporated into a bispecific format which can be readily expressed and assembled with minimal or substantially no mispairing of the antigen-binding sequences due to the presence of the TCR constant regions in the first antigen-binding moiety. Additional advantages of the first antigen-binding moiety and constructs provided herein will become more evident in the following disclosure below.

In summary, the first antigen-binding moiety provided herein comprises a first polypeptide comprising, from N-terminus to C-terminus, a first heavy chain variable domain (VH) of a first antibody operably linked to a first T cell receptor (TCR) constant region (C1), and a second polypeptide comprising, from N-terminus to C-terminus, a first light chain variable domain (VL) of the first antibody operably linked to a second TCR constant region (C2), wherein: C1 comprises an engineered CBeta comprising SEQ ID NO: 1 and C2 comprises an engineered CAlpha comprising SEQ ID NO: 2, amino acid C48 in SEQ ID NO: 1 and amino acid C41 in SEQ ID NO: 2 are capable of forming a non-native interchain disulphide bond, C1 and C2 are capable of forming a dimer, and the non-native interchain disulphide bond between C1 and C2 is capable of stabilizing the dimer.

TCR Constant Region

The first antigen-binding moiety provided herein comprises an alpha or beta constant region derived from a TCR.

FIGS. 3A and 3B set forth the amino acid sequences of native TCR constant regions of TCR alpha, and beta chains. For clarity and consistency, each of the amino acid residues in these sequences are numbered in FIGS. 4A and 4B, and such numbering is used throughout the present disclosure to refer to a particular amino acid residue on a particular TCR constant region.

Human TCR alpha chain constant region is known as TRAC, with the NCBI accession number of P01848, or an amino acid sequence of SEQ ID NO: 31.

Human TCR beta chain constant region has two different variants, known as TRBC1 and TRBC2 (IMGT nomenclature) (see also Toyonaga B, et al., PNAs, Vol. 82, pp. 8624-8628, Immunology (1985)). The TRBC1 sequence (SEQ ID NO: 33) was chosen as the backbone to design the polypeptide complexes disclosed herein.

Specifically, the native TCR beta chain contains a native cysteine residue at position 74 (see FIG. 4B), which is unpaired and therefore does not form a disulphide bond in a native alpha/beta TCR. In the polypeptide complexes provided herein, this native cysteine residue at position 74 of TCR beta chain is mutated to an alanine residue. This may be useful to avoid incorrect intrachain or interchain pairing. In certain embodiments, the substitution in certain embodiments can improve the TCR refolding efficiencies in vitro.

In the present disclosure, the first and the second TCR constant regions of the first antigen-binding moiety provided herein are capable of forming a dimer comprising, between the TCR constant regions, at least one non-native interchain disulphide bond that is capable of stabilizing the dimer.

The term "dimer" as used herein refers to an associated structure formed by two molecules, such as polypeptides or proteins, via covalent or non-covalent interactions. A homodimer or homodimerization is formed by two identical molecules, and a heterodimer or heterodimerization is formed by two different molecules. The dimer formed by the first and the second TCR constant regions is a heterodimer.

A "mutated" amino acid residue refers to one which is substituted, inserted or added and is different from its native counterpart residue in a corresponding native TCR constant region. For example, if an amino acid residue at a particular position in the wild-type TCR constant region is referred to as the "native" residue, then its mutated counterpart is any residue that is different from the native residue but resides at the same position on the TCR constant region. A mutated residue can be a different residue which substitutes the native residue at the same position, or which is inserted before the native residue and therefore takes up its original position.

In the polypeptide complexes provided herein, the first and/or the second TCR constant regions have been engineered to comprise one or more mutated amino acid residues that are responsible for forming the non-native interchain disulphide bond. To introduce such a mutated residue to the TCR constant region, an encoding sequence of a TCR region can be manipulated to for example, substitute a codon encoding a native residue for the codon encoding the mutated residue, or to insert a codon encoding the mutated residue before the codon of the native residue.

In the polypeptide complexes provided herein, the first and/or the second TCR constant regions have been engineered to comprise one or more mutated cysteine residues such that, after replacement to cysteine residues, a non-native interchain disulphide bond could be formed between the two TCR constant regions.

The non-native interchain disulphide bond is capable of stabilizing the first antigen-binding moiety. Such effects in stablization can be embodied in various ways. For example, the presence of the mutated amino acid residue or the non-native interchain disulphide bond can enable the polypeptide complex to stably express, and/or to express in a high level, and/or to associate into a stable complex having the desired biological activity (e.g. antigen binding activity), and/or to express and assemble into a high level of desired stable complex having the desired biological activity. The capability of the interchain disulphide bond to stabilize the first and the second TCR constant regions can be assessed using proper methods known in the art, such as the molecular weight displayed on SDS-PAGE, or thermostability measured by differential scanning calorimetry (DSC) or differential scanning fluorimetry (DSF). In an illustrative example, formation of a stable first antigen-binding moiety provided herein can be confirmed by SDS-PAGE, if a product shows a molecular weight comparable to the combined molecular weight of the first and the second polypeptides. In certain embodiments, the first antigen-binding moiety provided herein is stable in that its thermal stability is no less than 50%, 60%, 70%, 80%, or 90% of that of a natural Fab. In certain embodiments, the first antigen-binding moiety provided herein is stable in that its thermal stability is comparable to that of a natural Fab.

Without wishing to be bound by any theory, it is believed that the non-native interchain disulphide bond formed between the first and the second TCR constant regions in the first antigen-binding moiety are capable of stabilizing the heterodimer of TCR constant regions, thereby enhancing the level of correct folding, the structural stability and/or the expression level of the heterodimer and of the first antigen-binding moiety. Unlike native TCR anchored on the membrane of T cell surface, heterodimers of native TCR extracellular domains are found to be much less stable, despite of its similarity to antibody Fab in 3D structure. As a matter of fact, the instability of native TCR in soluble condition used to be a significant obstacle that prevents elucidation of its crystal structure (see Wang, *Protein Cell*, 5(9), pp. 649-652 (2014)). By introducing a pair of Cysteine (Cys) mutations in TCR constant regions and thereby enabling formation of interchain non-native disulphide bond, the first antigen-binding moiety can be stably expressed while in the meantime the antigen-binding capabilities of the antibody variable region are retained.

The TCR constant region comprising a mutated residue is also referred to herein as an "engineered" TCR constant region. In certain embodiments, the first TCR constant region (C1) of the polypeptide complex comprises an engineered TCR Alpha chain (CAlpha), and the second TCR constant region (C2) comprises an engineered TCR Beta chain (CBeta). In the polypeptide complexes provided herein, C1 comprises an engineered CBeta, and C2 comprises an engineered CAlpha.

In the polypeptide complexes provided herein, the engineered TCR constant region comprises one or more mutated cysteine residue within a contact interface of the first and/or the second engineered TCR constant regions.

The term "contact interface" as used herein refers to the particular region(s) on the polypeptides where the polypeptides interact/associate with each other. A contact interface comprises one or more amino acid residues that are capable of interacting with the corresponding amino acid residue(s) that comes into contact or association when interaction occurs. The amino acid residues in a contact interface may or may not be in a consecutive sequence. For example, when the interface is three-dimensional, the amino acid residues within the interface may be separated at different positions on the linear sequence.

In certain embodiments, one or more disulphide bonds can be formed between the engineered CAlpha and the engineered CBeta. In certain embodiments, the mutated cysteine residue in CBeta is S56C (corresponding to amino acid C48 in SEQ ID NO: 1), and the mutated cysteine residues in CAlpha is T49C (corresponding to amino acid C41 in SEQ ID NO: 2), and wherein the pair of cysteine residues are capable of forming a non-native interchain disulphide bond.

As used herein throughout the application, "XnY" with respect to a TCR constant region is intended to mean that the $n^{th}$ amino acid residue X on the TCR constant region (based on the numbering in FIGS. 4A and 4B as provided herein) is replaced by amino acid residue Y, where X and Y are respectively the one-letter abbreviation of a particular amino acid residue. It should be noted that the number n is solely based on the numbering provided in FIGS. 4A and 4B, and it could appear different from its actual position. To illustrate, the sequence of CBeta(S56C)(N69Q) shown in SEQ ID NO: 1 is used as an example. While the substitution of S to C occurs at the $48^{th}$ residue in SEQ ID NO:1, the very residue is designated as the $56^{th}$ residue based on the numbering system in FIG. 4B, and therefore that substitution of S to C is designated as S56C, but not S48C. Similarly, the substitution of N to Q is also designated as N69Q based on the numbering system in FIGS. 4A and 4B. This designation rule of amino acid residue substitution applies to all TCR constant region in the present disclosure, unless otherwise specified.

In the polypeptide complexes provided herein, the engineered CBeta comprises or is SEQ ID NO: 1, and the engineered CAlpha comprises or is SEQ ID NO: 2.

The amino acid sequences of SEQ ID NOs: 1 and 2 are provided below.

SEQ ID NO: 1
EVAVFEPSEAEISHTQKATLVCLATGFYPDHVELSWWVNGKEVHSGV<u>C</u>TDP

QPLKEQPALQDSRYALSSRLRVSATFWQNPRNHFRCQVQFYGLSENDEWTQ

DRAKPVTQIVSAEA

SEQ ID NO: 2
AVYQLRDSKSSDKSVCLFTDFDSQTQVSQSKDSDVYITDK<u>C</u>VLDMRSMDFK

SNSAVAWSQKSDFACANAFQNSIIPEDTFFPSPESS

In the peptide complexes provided herein, one or more native glycosylation site present in the native TCR constant regions has been modified (e.g. removed) in the first antigen-binding moiety provided in the present disclosure. The term "glycosylation site" as used herein with respect to a polypeptide sequence refers to an amino acid residue with a side chain to which a carbohydrate moiety (e.g. an oligosaccharide structure) can be attached. Glycosylation of polypeptides like antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of native glycosylation sites can be conveniently accomplished by altering the amino acid sequence such that one or more of the above-described tripeptide sequences (for N-linked glycosylation sites) or one or more serine or threonine residues (for O-linked glycosylation sites) are substituted.

In the first antigen-binding moiety provided herein, at least one native glycosylation site is absent in the engineered TCR constant regions, for example, in the first and/or the second TCR constant regions. Without wishing to be bound by any theory, but it is believed that the first antigen-binding moiety provided herein can tolerate removal of all or part of the glycosylation sites without affecting the protein expression and stability, in contrast to existing teachings that presence of N-linked glycosylation sites on TCR constant region, such as CAlpha (i.e. N34, N68, and N79) and CBeta (i.e. N69) are necessary for protein expression and stability (see Wu et al., Mabs, 7:2, 364-376, 2015).

In the first antigen-binding moiety provided herein, the N-glycosylation sites in the engineered CAlpha at N34, N68, and N79 are absent. The engineered CAlpha sequence absent of a glycosylation site comprises or is SEQ ID NO: 2. In the first antigen-bindign moiety provided herein, the N-glycosylation site in the engineered CBeta at N69 is absent. The engineered CBeta sequence (TRBC1) absent of glycosylation site comprises or is SEQ ID NO: 1.

In the first antigen-binding moiety provided herein, the constant regions derived from a TCR are operably linked to the variable regions derived from an antibody.

In certain embodiments, the first antibody variable domain (VH) is fused to the first TCR constant region (C1) at a first conjunction domain, and the first antibody variable domain (VL) is fused to the second TCR constant region (C2) at a second conjunction domain.

"Conjunction domain" as used herein refers to a boundary or border region where two amino acid sequences are fused or combined. In certain embodiments, the first conjunction domain comprises at least a portion of the C terminal fragment of an antibody V/C conjunction, and the second conjunction domain comprises at least a portion of the N-terminal fragment of a TCR V/C conjunction.

The term "antibody V/C conjunction" as used herein refers to the boundary of antibody variable domain and constant domain, for example, the boundary between heavy chain variable domain and the CH1 domain, or between light chain variable domain and the light chain constant domain. Similarly, the term "TCR V/C conjunction" refers to the boundary of TCR variable domain and constant domain, for example, the boundary between TCR Alpha variable domain and constant domain, or between TCRBeta variable domain and constant domain.

In certain embodiments, the first polypeptide comprises a sequence comprising domains operably linked as in formula (I): VH-HCJ-C1, and the second polypeptide comprises a sequence comprising domains operably linked as in formula (II): VL-LCJ-C2, wherein:
  VH is a heavy chain variable domain of an antibody;
  HCJ is a first conjunction domain as defined supra;
  C1 is a first TCR constant domain as defined supra;
  VL is a light chain variable domain of an antibody;
  LCJ is a second conjunction domain as defined supra;
  C2 is a second TCR constant domain as defined supra.

In such embodiments, C1 is an engineered CBeta which comprises or is SEQ ID NO: 1, and C2 is an engineered CAlpha which comprises or is SEQ ID NO: 2, the HCJ comprises or is SEQ ID NO: 23, and LCJ comprises or is SEQ ID NO: 24.

Antibody Variable Region

The bispecific polypeptide complex provided herein comprises a first antigen-binding moiety associated with a second antigen-binding moiety, and one of them specifically binds to CD3, while the other specifically binds to CD19. In the polypeptide complex provided herein, the first antigen-binding moiety comprises a first heavy chain variable domain (VH1) and a first light chain variable domain (VL1) of a first antibody, and the second antigen-binding moiety comprises a second heavy chain variable domain (VH2) and a second light chain variable domain (VL2) of a second antibody, wherein the first antibody and the second antibody are different and are selected from the group consisting of an anti-CD3 antibody and an anti-CD19 antibody. In certain embodiments, the first antibody is an anti-CD3 antibody, and the second antibody is an anti-CD19 antibody. In certain other embodiments, the first antibody is an anti-CD19 antibody, and the second antibody is an anti-CD3 antibody.

In a conventional native antibody, a variable region comprises three CDR regions interposed by flanking framework (FR) regions, for example, as set forth in the following formula: FR1-CDR1-FR2-CDR2-FR3-CDR3-FR4, from N-terminus to C-terminus a) Anti-CD3 Binding Moiety In the polypeptide complex provided herein, the first antigen-binding moiety or the second antigen-binding moiety is an anti-CD3 binding moiety. In certain embodiments, the anti-CD3 binding moiety is derived from the anti-CD3 antibody WBP3311_2.306.4-z1 shown in Table A below. The CDR sequences of the WBP3311_2.306.4-z1 antibody are provided below.

TABLE A

| Antibody ID: | | CDR1 | CDR2 | CDR3 |
|---|---|---|---|---|
| WBP3311_2.306.4-z1 | VH | SEQ ID NO: 3 GFAFTDYYIH | SEQ ID NO: 4 WISPGNVNT KYNENFKG | SEQ ID NO: 5 DGYSLYYFDY |

TABLE A-continued

| Antibody ID: | | CDR1 | CDR2 | CDR3 |
|---|---|---|---|---|
| WBP3311_2.306.4-z1 | VK | SEQ ID NO: 6 KSSQSLLNS RTRKNYLA | SEQ ID NO: 7 WASTRQS | SEQ ID NO: 8 TQSHTLRT |

Heavy and kappa light chain variable region sequences of the WBP3311_2.306.4-z1 antibody are provided below.

WBP3311_2.306.4-z1-VH
Amino acid sequence (SEQ ID NO: 15):
QVQLVQSGAEVKKPGSSVKVSCKAS<u>GFAFTDYYIHW</u>VRQAPGQGLEW<u>MGWI</u>

<u>SPGNVNTKYNENFKGR</u>VTITADKSTSTAYMELSSLRSEDTAVYYCAR<u>DGYS</u>

<u>LYYFDY</u>WGQGTLVTVSS

Nucleic acid sequence (SEQ ID NO: 16):
CAGGTGCAGCTTGTGCAGTCTGGGGCAGAAGTGAAGAAGCCTGGGTCTAGT

GTCAAGGTGTCATGCAAGGCTAGCGGGTTCGCCTTTACTGACTACTACATC

CACTGGGTGCGGCAGGCTCCCGGACAAGGGTTGGAGTGGATGGGATGGATC

TCCCCAGGCAATGTCAACACAAAGTACAACGAGAACTTCAAAGGCCGCGTC

ACCATTACCGCCGACAAGAGCACCTCCACAGCCTACATGGAGCTGTCCAGC

CTCAGAAGCGAGGACACTGCCGTCTACTACTGTGCCAGGGATGGGTACTCC

CTGTATTACTTTGATTACTGGGGCCAGGGCACACTGGTGACAGTGAGCTCC

WBP3311_2.306.4-z1-VK
Amino acid sequence (SEQ ID NO: 17):
DIVMTQSPDSLAVSLGERATINC<u>KSSQSLLNSRTRKNYLA</u>WYQQKPGQPPK LLIY<u>WASTRQS</u>GVPDRF<u>SGSGSGT</u>DFTLTIS<u>SLQAED</u>VAVYYC<u>TQSHTLRT</u>

FGGGTKVEIK

Nucleic acid sequence (SEQ ID NO: 18):
GATATCGTGATGACCCAGAGCCCAGACTCCCTTGCTGTCTCCCTCGGCGAA

AGAGCAACCATCAACTGCAAGAGCTCCCAAAGCCTGCTGAACTCCAGGACC

AGGAAGAATTACCTGGCCTGGTATCAGCAGAAGCCCGGCCAGCCTCCTAAG

CTGCTCATCTACTGGGCCTCCACCCGGCAGTCTGGGGTGCCCGATCGGTTT

AGTGGATCTGGGAGCGGGACAGACTTCACATTGACAATTAGCTCACTGCAG

GCCGAGGACGTGGCCGTCTACTACTGTACTCAGAGCCACACTCTCCGCACA

TTCGGCGGAGGGACTAAAGTGGAGATTAAG

CDRs are known to be responsible for antigen binding.

In certain embodiments, the anti-CD3 binding moiety provided herein comprises the heavy chain CDR3 sequence of WBP3311_2.306.4-z1. In certain embodiments, the anti-CD3 binding moiety provided herein comprises a heavy chain CDR3 comprising SEQ ID NO: 5. Heavy chain CDR3 regions are located at the center of the antigen-binding site, and therefore are believed to make the most contact with the antigen and provide the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S., Nature. 302:575-81 (1983)). The diversity in the heavy chain CDR3 is sufficient to produce most antibody specificities (Xu J L, Davis M M., Immunity. 13:37-45 (2000)) as well as desirable antigen-binding affinity (Schier R, et al., J Mol Biol. 263:551-67 (1996)).

The anti-CD3 binding moiety provided herein further comprises suitable framework region (FR) sequences, as long as the anti-CD3 binding moiety can specifically bind to CD3.

The humanized anti-CD3 antibody WBP3311_2.306.4-z1 has the specific binding affinity to CD3-expressing cell (e.g. CD4 T cell) and can activate human T cells and trigger cytokine release of TNFalpha and IFNgamma.

In certain embodiments, the anti-CD3 binding moiety provided herein comprises a heavy chain variable domain sequence comprising SEQ ID NO: 15 and a light chain variable domain sequence comprising SEQ ID NO: 17.

Binding affinity of the anti-CD3 binding moiety provided herein can be represented by $K_D$ value, which represents the ratio of dissociation rate to association rate ($k_{off}/k_{on}$) when the binding between the antigen and antigen-binding molecule reaches equilibrium. The antigen-binding affinity (e.g. $K_D$) can be appropriately determined using suitable methods known in the art, including, for example, flow cytometry assay. In some embodiments, binding of the antibody to the antigen at different concentrations can be determined by flow cytometry, the determined mean fluorescence intensity (MFI) can be firstly plotted against antibody concentration, $K_D$ value can then be calculated by fitting the dependence of specific binding fluorescence intensity (Y) and the concentration of antibodies (X) into the one site saturation equation: $Y=B_{max}*X/(K_D+X)$ using Prism version 5 (GraphPad Software, San Diego, Calif.), wherein B. refers to the maximum specific binding of the tested antibody to the antigen.

In certain embodiments, the anti-CD3 binding moiety provided herein is capable of specifically binding to human CD3 expressed on a cell surface, or a recombinant human CD3. CD3 is a receptor expressed on cell. A recombinant CD3 is soluble CD3 which is recombinantly expressed and is not associated with a cell membrane. A recombinant CD3 can be prepared by various recombinant technologies. In one example, the CD3 DNA sequence encoding the extracellular domain of human CD3 (NP 000724.1) (Met1-Asp126) can be fused with a polyhistidine tag at the C-terminus in an expression vector, and then transfected and expressed in 293E cells and purified by Ni-Affinity chromatography.

In some embodiments, the anti-CD3 binding moiety provided herein is capable of specifically binding to human CD3 expressed on surface of cells with a binding affinity ($K_D$) of no more than $5\times10^{-9}$M, no more than $4\times10^{-9}$M, no more than $3\times10^{-9}$M, no more than $2\times10^{-9}$M, no more than $10^{-9}$M, no more than $5\times10^{-10}$ NI no more than $4\times10^{-10}$ M, no more than $3\times10^{-10}$ M, no more than $2\times10^{-10}$ M, no more than $10^{-10}$ M, no more than $5\times10^{-11}$ M, or no more than $4\times10^{-11}$ M, no more than $3\times10^{-11}$ M, or no more than $2\times10^{-11}$ M, or no more than $10^{-11}$ M as measured by flow cytometry assay.

In certain embodiments, the anti-CD3 binding moiety provided herein cross-reacts with cynomolgus monkey CD3, for example, cynomolgus monkey CD3 expressed on a cell surface, or a soluble recombinant cynomolgus monkey CD3.

Binding of the anti-CD3 binding moiety to recombinant CD3 or CD3 expressed on surface of cells can be measured by methods known in the art, for example, sandwich assay such as ELISA, Western Blot, flow cytometry assay, and other binding assay. In certain embodiments, the anti-CD3 binding moiety provided herein specifically bind to recombinant human CD3 at an $EC_{50}$ (i.e. 50% binding concentration) of no more than 0.01 nM, no more than 0.02 nM, no more than 0.03 nM, no more than 0.04 nM, no more than 0.05 nM, no more than 0.06 nM, no more than 0.07 nM or no more than 0.08 nM by ELISA. In certain embodiments, the anti-CD3 binding moiety provided herein specifically bind to human CD3 expressed on surface of cells at an $EC_{50}$ of no more than 0.5 nM, no more than 0.6 nM, no more than 0.7 nM, no more than 0.8 nM, no more than 0.9 nM, no more than 1 nM, no more than 2 nM, no more than 3 nM, no more than 4 nM, no more than 5 nM, no more than 6 nM, no more than 7 nM, no more than 8 nM, no more than 9 nM or no more than 10 nM by flow cytometry assay.

In certain embodiments, the anti-CD3 binding moiety binds to cynomolgus monkey CD3 with a binding affinity similar to that of human CD3. For example, binding of the exemplary antibody WBP3311_2.306.4 to cynomolgus monkey CD3 is at a similar affinity or $EC_{50}$ value to that of human CD3.

In certain embodiments, the anti-CD3 binding moiety provided herein specifically binds to recombinant cynomolgus monkey CD3 with an $EC_{50}$ of no more than 0.001 nM, no more than 0.005 nM, no more than 0.01 nM, no more than 0.02 nM, no more than 0.03 nM, no more than 0.04 nM, or no more than 0.05 nM by ELISA.

In certain embodiments, the anti-CD3 binding moiety provided herein has a specific binding affinity to human CD3 which is sufficient to provide for diagnostic and/or therapeutic use. A number of therapeutic strategies modulate T cell immunity by targeting TCR signaling, particularly by anti-human CD3 monoclonal antibodies that are clinically used.

b) Anti-CD19 Antibody

In the polypeptide complex provided herein, the first antigen-binding moiety or the second antigen-binding moiety is an anti-CD19 binding moiety. In certain embodiments, the anti-CD19 binding moiety is derived from anti-CD19 antibody W7011-4.155.8-z1-P15 shown in Table B below. The CDR sequences of the anti-CD19 antibody are provided below.

TABLE B

|  |  | CDR1 | CDR2 | CDR3 |
|---|---|---|---|---|
| W7011-4.155.8-z1-P15 | VH | SEQ ID NO: 9 GYAFTSYNMY | SEQ ID NO: 10 YIDPYNADT TYNQKFKG | SEQ ID NO: 11 TAYAMDY |
| W7011-4.155.8-z1-P15 | VK | SEQ ID NO: 12 SASSTVNYMH | SEQ ID NO: 13 STSNLAS | SEQ ID NO: 14 HQWSSYPYT |

Heavy and kappa light chain variable region sequences of the WBP7011_4.155.8-z1-P15 antibody are provided below.

W7011-4.155.8-z1-P15-VH
Amino acid sequence (SEQ ID NO: 19):
QMQLVQSGPEVKKPGTSVKVSCKAS<u>GYAFTSYNMY</u>WVRQARGQRLEWIG<u>YI</u>

<u>DPYNADTTYNQKFKG</u>RVTITRDMSTSTAYMELSSLRSEDTAVYYCLT<u>TAYA</u>

<u>MDY</u>WGQGTLVTVSS

Nucleic acid sequence (SEQ ID NO: 20):
CAAATGCAGCTCGTCCAGTCTGGACCTGAAGTGAAGAAGCCCGGGACATCC

GTCAAGGTCTCATGTAAGGCTAGCGGGTACGCATTCACTTCCTACAACATG

TACTGGGTGCGCCAGGCCAGAGGACAGAGGTTGGAGTGGATCGGCTACATC

GACCCATACAACGCCGATACTACCTACAATCAGAAGTTTAAAGGGCGGGTG

ACCATTACCCGGGATATGTCCACCTCCACCGCCTACATGGAGCTGAGCAGC

CTGAGGAGCGAGGACACAGCCGTGTACTACTGCCTGACAACAGCCTATGCC

ATGGACTATTGGGGCCAGGGCACACTTGTGACTGTGAGCAGT

W7011-4.155.8-z1-P15-VK
Amino acid sequence (SEQ ID NO: 21):
DIQLTQSPSFLSASVGDRVTITC<u>SASSTVNYMH</u>WYQQKPGKAPKLLIY<u>STS</u>

<u>NLAS</u>GVPSRFSGSGSGTEFTLTISSLQPEDFATYYC<u>HQWSSYPYT</u>FGQGTK

LEIK

Nucleic acid sequence (SEQ ID NO: 22):
GACATCCAGCTCACCCAATCCCCTTCTTTCCTCTCCGCAAGTGTCGGAGAT

AGGGTGACTATCACCTGCTCAGCTTCTTCAACCGTGAACTACATGCATTGG

TACCAGCAGAAGCCCGGGAAAGCCCCAAAGCTGCTGATCTACAGCACCTCC

AATCTGGCCAGTGGAGTGCCAAGCCGGTTTAGCGGGAGCGGCTCCGGCACT

GAATTCACTTTGACAATTAGCAGCCTTCAGCCTGAGGACTTTGCCACATAT

TACTGTCACCAGTGGTCCAGCTACCCCTACACATTCGGGCAGGGCACAAAG

CTGGAGATTAAG

CDRs are known to be responsible for antigen binding.

In certain embodiments, the anti-CD19 binding moiety disclosed herein comprises a heavy chain CDR3 sequence of the anti-CD19 antibody W7011-4.155.8-z1-P15. In certain embodiments, the anti-CD19 binding moiety provided herein comprises a heavy chain CDR3 sequence comprising SEQ ID NO: 11. Heavy chain CDR3 regions are located at the center of the antigen-binding site, and therefore are believed to make the most contact with the antigen and provide the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S., Nature. 302:575-81 (1983)). The diversity in the heavy chain CDR3 is sufficient to produce most antibody specificities (Xu J L, Davis M M. Immunity. 13:37-45 (2000)) as well as desirable antigen-binding affinity (Schier R, et al., J Mol Biol. 263: 551-67 (1996)).

The anti-CD19 binding moiety provided herein further comprises suitable framework region (FR) sequences, as long as the anti-CD19 binding moiety can specifically bind to CD19.

In certain embodiments, the anti-CD19 binding moiety provided herein comprises a heavy chain variable domain sequence comprising SEQ ID NO: 19 and a light chain variable domain sequence comprising SEQ ID NO: 21.

In some embodiments, the anti-CD19 binding moiety provided herein is capable of specifically binding to human CD19 expressed on surface of cells with a binding affinity ($K_D$) of no more than $5\times10^{-9}$M, no more than $1\times10^{-9}$M, no more than $9\times10^{-10}$ M, no more than $8\times10^{-10}$ M, no more than $7\times10^{-10}$ M, no more than $6\times10^{-10}$ NI no more than $5\times10^{-10}$ M, no more than $4\times10^{-10}$ M, no more than $3\times10^{-10}$ M no more than $2\times10^{-10}$ M, or no more than $1\times10^{-10}$ M as measured by flow cytometry assay.

In certain embodiments, the anti-CD19 binding moiety provided herein cross-reacts with cynomolgus monkey CD19, for example, cynomolgus monkey CD19 expressed on a cell surface, or a soluble recombinant cynomolgus monkey CD19.

Binding of the anti-CD19 binding moiety to CD19 expressed on a cell can be measured by methods known in the art, for example, sandwich assay such as ELISA, Western Blot, flow cytometry assay, and other binding assay. In certain embodiments, the anti-CD19 binding moiety provided herein specifically binds to human CD19 expressed on a cell with an $EC_{50}$ of no more than 0.01 nM, no more than 0.02 nM, no more than 0.03 nM, no more than 0.04 nM, no more than 0.05 nM, no more than 0.1 nM, no more than 0.2 nM, no more than 0.3 nM, no more than 0.4 nM, no more than 0.5 nM, no more than 0.5 nM, no more than 0.6 nM, no more than 0.7 nM, no more than 0.8 nM, no more than 0.9 nM, or no more than 1 nM by flow cytometry assay.

In certain embodiments, the anti-CD19 binding moiety binds to cynomolgus monkey CD19 with a binding affinity similar to that of human CD19. In certain embodiments, the anti-CD19 binding moiety provided herein specifically binds to cynomolgus monkey CD19 expressed on a cell at an $EC_{50}$ of no more than 0.2 nM, no more than 0.5 nM, no more than 0.8 nM, no more than 1 nM, no more than 2 nM, or no more than 3 nM by flow cytometry assay.

In certain embodiments, the anti-CD19 binding moiety provided herein is internalized by a CD19-expressing cell at an $EC_{50}$ of no more than 1 pM, no more than 2 pM, no more than 3 pM, no more than 4 pM, no more than 5 pM, no more than 6 pM, no more than 7 pM, no more than 8 pM, no more than 9 pM, no more than 10 pM, no more than 11 pM, no more than 12 pM, no more than 13 pM, no more than 14 pM, no more than 15 pM, no more than 16 pM, no more than 17 pM, no more than 18 pM, no more than 19 pM, no more than 20 pM, no more than 21 pM, no more than 22 pM, no more than 23 pM, no more than 24 pM, no more than 25 pM, no more than 30 pM, no more than 35 pM, no more than 40 pM, no more than 45 pM, or no more than 50 pM by Fab-Zap assay.

Bispecific Polypeptide Complex

In certain embodiments, the first and/or the second antigen binding moiety is multivalent, such as bivalent, trivalent, tetravalent. The term "valent" as used herein refers to the presence of a specified number of antigen binding sites in a given molecule. As such, the terms "bivalent", "tetravalent", and "hexavalent" denote the presence of two binding sites, four binding sites, and six binding sites, respectively, in an antigen-binding molecule. A bivalent molecule can be monospecific if the two binding sites are both for specific binding of the same antigen or the same epitope. Similarly, a trivalent molecule can be bispecific, for example, when two binding sites are monospecific for a first antigen (or epitope) and the third binding site is specific for a second antigen (or epitope). In certain embodiments, the first and/or the second antigen-binding moiety in the bispecific polypeptide complex provided herein can be bivalent, trivalent, or tetravalent, with at least two binding sites specific for the same antigen or epitope. This, in certain embodiments, provides for stronger binding to the antigen or the epitope than a monovalent counterpart. In certain embodiments, in a bivalent antigen-binding moiety, the first valent of binding site and the second valent of binding site are structurally identical (i.e. having the same sequences), or structurally different (i.e. having different sequences albeit with the same specificity).

In certain embodiments, the first and/or the second antigen binding moiety is multivalent and comprises two or more antigen binding sites operably linked together, with or without a spacer.

In certain embodiments, the second antigen binding moiety comprises two or more Fab of the second antibody. The two Fabs can be operably linked to each other, for example the first Fab can be covalently attached to the second Fab via heavy chain, with or without a spacer in between.

In certain embodiments, the first antigen-binding moiety is linked to a first dimerization domain, and the second antigen-binding moiety is linked to a second dimerization domain. The term "dimerization domain" as used herein refers to the peptide domain which is capable of associating with each other to form a dimer, or in some examples, enables spontaneous dimerization of two peptides.

In certain embodiments, the first dimerization domain can be associated with the second dimerization domain. The association can be via any suitable interaction or linkage or bonding, for example, via a connecter, a disulphide bond, a hydrogen bond, electrostatic interaction, a salt bridge, or hydrophobic-hydrophilic interaction, or the combination thereof. Exemplary dimerization domains include, without limitation, antibody hinge region, an antibody CH2 domain, an antibody CH3 domain, and other suitable protein monomers capable of dimerizing and associating with each other. Hinge region, CH2 and/or CH3 domain can be derived from any antibody isotypes, such as IgG1, IgG2, and IgG4.

A "disulphide bond" refers to a covalent bond with the structure R—S—S—R'. The amino acid cysteine comprises a thiol group that can form a disulphide bond with a second thiol group, for example from another cysteine residue. The disulphide bond can be formed between the thiol groups of two cysteine residues residing respectively on the two polypeptide chains, thereby forming an interchain bridge or interchain bond.

A hydrogen bond is formed by electrostatic attraction between two polar groups when a hydrogen atom covalently bound to a highly electronegative atom such as nitrogen, oxygen, or fluorine. A hydrogen bond can be formed in a polypeptide between the backbone oxygens (e.g. chalcogen groups) and amide hydrogens (nitrogen group) of two residues, respectively, such as a nitrogen group in Asn and an oxygen group in His, or an oxygen group in Asn and a nitrogen group in Lys. A hydrogen bond is stronger than a Van der Waals interaction, but weaker than covalent or ionic bonds, and is critical in maintaining the secondary structure and tertiary structure. For example, an alpha helix is formed when the spacing of amino acid residues occurs regularly between positions i and i+4, and a beta sheet is a stretch of peptide chain 3-10 amino acids long formed when two peptides joined by at least two or three backbone hydrogen bonds, forming a twisted, pleated sheet.

Electrostatic interaction is non-covalent interaction and is important in protein folding, stability, flexibility and function, including ionic interactions, hydrogen bonding and halogen bonding. Electrostatic interactions can be formed in a polypeptide, for example, between Lys and Asp, between Lys and Glu, between Glu and Arg, or between Glu, Trp on the first chain and Arg, Val or Thr on the second chain.

A salt bridge is close-range electrostatic interactions that mainly arises from the anionic carboxylate of either Asp or Glu and the cationic ammonium from Lys or the guanidinium of Arg, which are spatially proximal pairs of oppositely charged residues in native protein structures. Charged and polar residues in largely hydrophobic interfaces may act as hot spots for binding. Among others, residues with ionizable side chains such as His, Tyr, and Ser can also participate the formation of a salt bridge.

A hydrophobic interaction can be formed between one or more Val, Tyr and Ala on the first chain and one or more Val, Leu, and Trp on the second chain, or His and Ala on the first chain and Thr and Phe on the second chain (see Brinkmann, et al, 2017, Supra).

In certain embodiments, the first and/or the second dimerization domain comprises at least a portion of an antibody hinge region. In certain embodiments, the first and/or the second dimerization domain may further comprise an antibody CH2 domain, and/or an antibody CH3 domain. In certain embodiments, the first and/or the second dimerization domain comprises at least a portion of Hinge-Fc region, i.e. Hinge-CH2-CH3 domain. In certain embodiments, the first dimerization domain can be operably linked to the C terminal of the first TCR constant region. In certain embodiments, the second dimerization domain can be operably linked to the C terminal of the antibody CH1 constant region of the second antigen-binding moiety.

In the polypeptide complex provided herein, C1 comprises an engineered CBeta and the first dimerization domain is operably linked to the engineered CBeta at a third conjunction domain, which comprises SEQ ID NO: 25.

In the polypeptide complex provided herein, the first dimerization domain is operably linked to the C-terminal of an engineered TCR constant region, and together forms a chimeric constant region. In other words, the chimeric constant region comprises the first dimerization domain operably linked with the engineered TCR constant region.

In certain embodiments, the chimeric constant region comprises an engineered CBeta attached to the first hinge-Fc region derived from IgG1, IgG2 or IgG4. Exemplary sequences of such a chimeric constant region are provided in Example 2.

In certain embodiments, the chimeric constant region further comprises a first antibody CH2 domain, and/or a first antibody CH3 domain. For example, the chimeric constant region further comprises a first antibody CH2-CH3 domain attached to the C-terminus of the third conjunction domain. Exemplary sequences of such chimeric constant region are provided in Example 2.

These pairs of chimeric constant regions and second TCR constant domains are useful in that they can be manipulated to fuse to a desired antibody variable region, so as to provide for the polypeptide complex as disclosed herein. For example, an antibody heavy chain variable region can be fused to the chimeric constant region (comprising C1), thereby rendering the first polypeptide chain of the polypeptide complex provided herein; and similarly, an antibody light chain variable region can be fused to the second TCR constant domain (comprising C2), thereby rendering the second polypeptide chain of the polypeptide complex provided herein.

In certain embodiments, the second dimerization domain comprises a hinge region. The hinge region may derived from an antibody, such as IgG1, IgG2, or IgG4. In certain embodiments, the second dimerization domain may optionally further comprise an antibody CH2 domain, and/or an antibody CH3 domain, for example such as a hinge-Fc region. The hinge region may be attached to the antibody heavy chain of the second antigen binding site (e.g. Fab).

In the bispecific polypeptide complex, the first and the second dimerization domain are capable of associating into a dimer. In certain embodiments, the first and the second dimerization domains are different and associate in a way that discourages homodimerization and/or favors heterodimerization. For example, the first and the second dimerization domains can be selected so that they are not identical and that they preferentially form heterodimers between each other rather than to form homodimers within themselves. In certain embodiments, the first and the second dimerization domains are capable of associating into heterodimers via formation of knob-into-hole, hydrophobic interaction, electrostatic interaction, hydrophilic interaction, or increased flexibility.

In certain embodiments, the first and the second dimerization domains comprise CH2 and/or CH3 domains which are respectively mutated to be capable of forming a knobs-into-holes. A knob can be obtained by replacement of a small amino acid residue with a larger one in the first CH2/CH3 polypeptide, and a hole can be obtained by replacement of a large residue with a smaller one. For details of the mutation sites for knobs into holes please see Ridgway et al., 1996, supra, Spiess et al., 2015, supra and Brinkmann et al., 2017, supra.

Bispecific Format

In the polypeptide complex provided herein, the first antigen-binding moiety and the second binding moiety are associated into an Ig-like structure. An Ig-like structure is like a natural antibody having a Y shaped construct, with two arms for antigen-binding and one stem for association and stabilization. The resemblance to natural antibody can provide for various advantages such as good in vivo pharmakinetics, desired immunological response and stability etc. It has been found that the Ig-like structure comprising the first antigen-binding moiety provided herein associated with the second antigen-binding moiety provided herein has thermal stability which is comparable to that of an Ig (e.g. an IgG). In certain embodiments, the Ig-like structure provided herein is at least 70%, 80%, 90%, 95% or 100% of that of a natural IgG.

The bispecific polypeptide complex provided herein comprises four polypeptide chains: i) VH1-C1-Hinge-CH2-CH3; ii) VL1-C2; iii) VH2-CH1-Hinge-CH2-CH3, and iv) VL2-CL, wherein the C1 and C2 are capable of forming a dimer comprising at least one non-native interchain bond, and the two hinge regions and/or the two CH3 domains are capable of forming one or more interchain bond that can facilitate dimerization.

The bispecific polypeptide complexes disclosed herein have longer in vivo half-life and are relatively easier to manufacture when comprared to bispecific polypeptide complexes in other formats.

Bispecific Complex Sequences

In some embodiments, the first antigen-binding moiety of the bispecific complex is capable of specifically binding to CD3, and the second antigen-binding moiety is capable of specifically binding to CD19. In other embodiments, the first antigen-binding moiety of the bispecific complex is capable of specifically binding to CD19, and the second antigen-binding moiety is capable of specifically binding to CD3.

In certain embodiments, the bispecific polypeptide complex comprises a combination of four polypeptide sequences: SEQ ID NO: 26, SEQ ID NO: 27, SEQ ID NO: 28, and SEQ ID NO: 29 (E17), as shown in Example 2. In certain embodiments, the bispecific polypeptide complex comprises a combination of four polypeptide sequences: SEQ ID NO: 26, SEQ ID NO: 27, SEQ ID NO: 28, and SEQ ID NO: 30 (F16), as shown in Example 2. In such embodiments, the first antigen binding moiety binds to CD3, and the second antigen binding moiety binds to CD19. The design of E17 is a bispecific, bivalent antibody, and the design of F16 is a bispecific and trivalent antigen-binding complex, with two repeats of anti-CD19 antibody Fab.

In certain embodiments, the bispecific polypeptide complex comprises four polypeptide chains comprising: i) VH1 operably linked to a first chimeric constant region; ii) VL1 operably linked to a second chimeric constant region; iii) VH2 operably linked to conventional antibody heavy chain constant region, and iv) VL2 operably linked to conventional antibody light chain constant region. In certain embodiments, the first chimeric constant region can comprise C1-Hinge-CH2-CH3, each as defined supra. In certain embodiments, the second chimeric constant region can comprise C2, as defined supra. In certain embodiments, the conventional antibody heavy chain constant region can comprise CH1-Hinge-CH2-CH3, each as defined supra. In certain embodiments, the conventional antibody light chain constant region can comprise CL, as defined supra.

Method of Preparation

The present disclosure provides isolated nucleic acids or polynucleotides that encode the polypeptide complex, and the bispecific anti-CD3×CD19 polypeptide complex provided herein.

The term "nucleic acid" or "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The nucleic acids or polynucleotides encoding the polypeptide complex and the bispecific polypeptide complex provided herein can be constructed using recombinant techniques. To this end, DNA encoding an antigen-binding moiety of a parent antibody (such as CDR or variable region) can be isolated and sequenced using conventional procedures (e.g., by using oligonucleotide probes that are capable of binding specifically to genes encoding the heavy and light chains of the antibody). Likewise, DNA encoding a TCR constant region can also be obtained. As an example, the polynucleotide sequence encoding the variable domain (VH) and the polynucleotide sequence encoding the first TCR constant region (C1) are obtained and operably linked to allow transcription and expression in a host cell to produce the first polypeptide. Similarly, polynucleotide sequence encoding VL are operably linked to polynucleotide sequence encoding C1, so as to allow expression of the second polypeptide in the host cell. If needed, encoding polynucleotide sequences for one or more spacers are also operably linked to the other encoding sequences to allow expression of the desired product.

The encoding polynucleotide sequences can be further operably linked to one or more regulatory sequences, optionally in an expression vector, such that the expression or production of the first and the second polypeptides is feasible and under proper control.

The encoding polynucleotide sequence(s) can be inserted into a vector for further cloning (amplification of the DNA) or for expression, using recombinant techniques known in the art. In another embodiment, the polypeptide complex and the bispecific polypeptide complex provided herein may be produced by homologous recombination known in the art. Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

The term "vector" as used herein refers to a vehicle into which a polynucleotide encoding a protein may be operably inserted so as to bring about the expression of that protein. Typically, the construct also includes appropriate regulatory sequences. For example, the polynucleotide molecule can include regulatory sequences located in the 5'-flanking region of the nucleotide sequence encoding the guide RNA and/or the nucleotide sequence encoding a site-directed modifying polypeptide, operably linked to the coding sequences in a manner capable of expressing the desired transcript/gene in a host cell. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

In some embodiments, the vector system includes mammalian, bacterial, yeast systems, etc., and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2.2 etc., and other laboratorial and commercially available vectors. Suitable vectors may include, plasmid, or viral vectors (e.g., replication defective retroviruses, adenoviruses and adeno-associated viruses).

Vectors comprising the polynucleotide sequence(s) provided herein can be introduced to a host cell for cloning or gene expression. The phrase "host cell" as used herein refers to a cell into which an exogenous polynucleotide and/or a vector has been introduced.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis, Pseudomonas* such as *P. aeruginosa*, and *Streptomyces*.

In addition to prokaryotes, eukaryotic microbes such as filamentous fungi or yeast are suitable cloning or expression hosts for the vectors encoding the polypeptide complex and the bispecific polypeptide complex. *Saccharomyces cerevi-*

*siae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger.*

Suitable host cells for the expression of glycosylated polypeptide complex and the bispecific polypeptide complex provided herein are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)), such as Expi293; baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors can be cultured in conventional nutrient media modified as appropriate for inducing promoters, selecting transformants, or amplifying the cloning vectors.

For production of the polypeptide complex and the bispecific polypeptide complex provided herein, the host cells transformed with the expression vector may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In one aspect, the present disclosure provides a method of expressing the polypeptide complex and the bispecific polypeptide complex provided herein, comprising culturing the host cell provided herein under the condition at which the polypeptide complex, or the bispecific polypeptide complex is expressed.

In certain embodiments, the present disclosure provides a method of producing the bispecific polypeptide complex provided herein, comprising a) introducing to a host cell: one or more polynucleotides encoding a first antigen-binding moiety comprising a first polynucleotide encoding a first polypeptide comprising, from N-terminus to C-terminus, a first heavy chain variable domain (VH) of a first antibody operably linked to a first TCR constant region (C1), a second polynucleotide encoding a second polypeptide comprising, from N-terminus to C-terminus, a first light chain variable domain (VL) of the first antibody operably linked to a second TCR constant region (C2), and one or more additional polynucleotides encoding a second antigen-binding moiety, wherein: C1 comprises an engineered CBeta comprising SEQ ID NO: 1 and C2 comprises an engineered CAlpha comprising SEQ ID NO: 2, amino acid C48 in SEQ ID NO: 1 and amino acid C41 in SEQ ID NO: 2 are capable of forming a non-native interchain disulphide bond, C1 and C2 are capable of forming a dimer, and the non-native interchain disulphide bond is capable of stabilizing the dimer of C1 and C2, the first antigen-binding moiety and the second antigen-binding moiety have reduced mispairing than otherwise would have been if both the first antigen-binding moiety and the second antigen-binding moieties were a natural Fab counterparts, and the first antibody has a first antigenic specificity and the second antibody has a second antigenic specificity, b) allowing the host cell to express the bispecific polypeptide complex.

In certain embodiments, the method further comprises isolating the bispecific polypeptide complex.

When using recombinant techniques, the bispecific polypeptide complex provided herein can be produced intracellularly, in the periplasmic space, or directly secreted into the medium. If the product is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the product is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The bispecific polypeptide complex provided herein prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

Where the bispecific polypeptide complex provided herein comprises immunoglobulin Fc domain, then protein A can be used as an affinity ligand, depending on the species and isotype of the Fc domain that is present in the polypeptide complex. Protein A can be used for purification of polypeptide complexes based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose.

Where the bispecific polypeptide complex provided herein comprises a CH3 domain, the Bakerbond ABX resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE' chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the polypeptide complex of interest and contaminants may be subjected to low pH hydrophobic interaction chromatography using an elution buffer at a pH between about 2.5-4.5, preferably performed at low salt concentrations (e.g., from about 0-0.25M salt).

In certain embodiments, the bispecific polypeptide complex provided herein can be readily purified with high yields using conventional methods. One of the advantages of the bispecific polypeptide complex is the significantly reduced mispairing between heavy chain and light chain variable domain sequences. This reduces production of unwanted byproducts and make it possible to obtain high purity product in high yields using relatively simple purification processes.

Derivatives

In certain embodiments, the bispecific polypeptide complex can be used as the base of conjugation with desired conjugates.

It is contemplated that a variety of conjugates may be linked to the polypeptide complex or the bispecific polypeptide complex provided herein (see, for example, "Conjugate Vaccines", Contributions to Microbiology and Immunology, J. M. Cruse and R. E. Lewis, Jr. (eds.), Carger Press, New York, (1989)). These conjugates may be linked to the polypeptide complex or the bispecific polypeptide complex by covalent binding, affinity binding, intercalation, coordinate binding, complexation, association, blending, or addition, among other methods.

In certain embodiments, the bispecific polypeptide complex provided herein may be engineered to contain specific sites outside the epitope binding portion that may be utilized for binding to one or more conjugates. For example, such a site may include one or more reactive amino acid residues, such as for example cysteine or histidine residues, to facilitate covalent linkage to a conjugate.

In certain embodiments, the bispecific polypeptide complex may be linked to a conjugate directly, or indirectly for example through another conjugate or through a linker.

For example, the bispecific polypeptide complex having a reactive residue such as cysteine may be linked to a thiol-reactive agent in which the reactive group is, for example, a maleimide, an iodoacetamide, a pyridyl disulphide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671).

For another example, the bispecific polypeptide complex may be conjugated to biotin, then indirectly conjugated to a second conjugate that is conjugated to avidin. For still another example, the polypeptide complex or the bispecific polypeptide complex may be linked to a linker which further links to the conjugate. Examples of linkers include bifunctional coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suherate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and his-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulphide linkage.

The conjugate can be a detectable label, a pharmacokinetic modifying moiety, a purification moiety, or a cytotoxic moiety. Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $_{186}Re$, $^{188}Re$, $_{153}Sm$, $^{212}Bi$, and $^{32}P$, other lanthanides, luminescent labels), chromophoric moiety, digoxigenin, biotin/avidin, a DNA molecule or gold for detection. In certain embodiments, the conjugate can be a pharmacokinetic modifying moiety such as PEG which helps increase half-life of the antibody. Other suitable polymers include, such as, carboxymethylcellulose, dextran, polyvinyl alcohol, polyvinyl pyrrolidone, copolymers of ethylene glycol/propylene glycol, and the like. In certain embodiments, the conjugate can be a purification moiety such as a magnetic bead. A "cytotoxic moiety" can be any agent that is detrimental to cells or that can damage or kill cells. Examples of cytotoxic moiety include, without limitation, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Methods for the conjugation of conjugates to proteins such as antibodies, immunoglobulins or fragments thereof are found, for example, in U.S. Pat. Nos. 5,208,020; 6,441,163; WO2005037992; WO2005081711; and WO2006/034488, which are incorporated herein by reference to the entirety.

Pharmaceutical Composition

The present disclosure also provides a pharmaceutical composition comprising the bispecific polypeptide complex provided herein and a pharmaceutically acceptable carrier.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

A "pharmaceutically acceptable carrier" refers to an ingredient in a pharmaceutical formulation, other than an active ingredient, which is bioactivity acceptable and non-toxic to a subject. Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a pharmaceutical composition provided herein decreases oxidation of the polypeptide complex or the bispecific polypeptide complex. This reduction in oxidation prevents or reduces loss of binding affinity, thereby improving protein stability and maximizing shelf-life. Therefore, in certain embodiments, compositions are provided that comprise the polypeptide complex or the bispecific polypeptide complex disclosed herein and one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving the polypeptide complex or the bispecific polypeptide complex as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the polypeptide complex, the bispecific polypeptide complex provided herein or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Method of Treatment

Therapeutic methods are also provided, comprising: administering a therapeutically effective amount of the polypeptide complex or the bispecific polypeptide complex provided herein to a subject in need thereof, thereby treating or preventing a condition or a disorder. In certain embodiments, the subject has been identified as having a disorder or condition likely to respond to the polypeptide complex or the bispecific polypeptide complex provided herein.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The therapeutically effective amount of the bispecific polypeptide complex provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

In certain embodiments, the bispecific polypeptide complex provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the polypeptide complex or the bispecific polypeptide complex provided herein is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The bispecific polypeptide complex provided herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In certain embodiments, the condition or disorder treated by the bispecific polypeptide complex provided herein is cancer or a cancerous condition, autoimmune diseases, infectious and parasitic diseases, cardiovascular diseases, neuropathies, neuropsychiatric conditions, injuries, inflammations, or coagulation disorder.

"Cancer" or "cancerous condition" as used herein refers to any medical condition mediated by neoplastic or malignant cell growth, proliferation, or metastasis, and includes both solid cancers and non-solid cancers such as leukemia. "Tumor" as used herein refers to a solid mass of neoplastic and/or malignant cells.

With regard to cancer, "treating" or "treatment" may refer to inhibiting or slowing neoplastic or malignant cell growth, proliferation, or metastasis, preventing or delaying the development of neoplastic or malignant cell growth, proliferation, or metastasis, or some combination thereof. With regard to a tumor, "treating" or "treatment" includes eradicating all or part of a tumor, inhibiting or slowing tumor growth and metastasis, preventing or delaying the development of a tumor, or some combination thereof.

For example, with regard to the use of the bispecific polypeptide complex disclosed herein to treat cancer, a therapeutically effective amount is the dosage or concentration of the polypeptide complex capable of eradicating all or part of a tumor, inhibiting or slowing tumor growth, inhibiting growth or proliferation of cells mediating a cancerous condition, inhibiting tumor cell metastasis, ameliorating any symptom or marker associated with a tumor or cancerous condition, preventing or delaying the development of a tumor or cancerous condition, or some combination thereof.

In certain embodiments, the conditions and disorders include tumors and cancers, for example, non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies, such as classical Hodgkin lymphoma (CHL), primary mediastinal large B-cell lymphoma, T-cell/histiocyte-rich B-cell lymphoma, EBV-positive and -negative PTLD, and EBV-associated diffuse large B-cell lymphoma (DLBCL), plasmablastic lymphoma, extranodal NK/T-cell lymphoma, nasopharyngeal carcinoma, and HHV8-associated primary effusion lymphoma, Hodgkin's lymphoma, neoplasm of the central nervous system (CNS), such as primary CNS lymphoma, spinal axis tumor, brain stem glioma.

In certain embodiments, the conditions and disorders include CD19-related condition, such as, B cell lymphoma, optionally Hodgkin lymphoma or non-Hodgkin lymphoma, wherein the non-Hodgkin lymphoma comprises: Diffuse large B-cell lymphoma (DLBCL), Follicular lymphoma, Marginal zone B-cell lymphoma (MZL), Mucosa-Associated Lymphatic Tissue lymphoma (MALT), Small lymphocytic lymphoma (chronic lymphocytic leukemia, CLL), or Mantle cell lymphoma (MCL), Acute Lymphoblastic Leukemia (ALL), or Waldenstrom's Macroglobulinemia (WM).

The bispecific polypeptide complex may be administered alone or in combination with one or more additional therapeutic means or agents.

In certain embodiments, when used for treating cancer or tumor or prolierative disease, the bispecific polypeptide complex provided herein may be administered in combination with chemotherapy, radiation therapy, surgery for the treatment of cancer (e.g., tumorectomy), one or more antiemetics or other treatments for complications arising from chemotherapy, or any other therapeutic agent for use in the treatment of cancer or any medical disorder that related. "Administered in combination" as used herein includes administeration simultaneously as part of the same pharmaceutical composition, simultaneously as separate compositions, or at different timings as separate compositions. A composition administered prior to or after another agent is considered to be administered "in combination" with that agent as the phrase is used herein, even if the composition and the second agent are administered via different routes. Where possible, additional therapeutic agents administered in combination with the polypeptide complex or the bispecific polypeptide complex provided herein are administered according to the schedule listed in the product information sheet of the additional therapeutic agent, or according to the Physicians' Desk Reference (Physicians' Desk Reference, 70th Ed (2016)) or protocols well known in the art.

In certain embodiments, the therapeutic agents can induce or boost immune response against cancer. For example, a tumor vaccine can be used to induce immune response to certain tumor or cancer. Cytokine therapy can also be used to enhance tumor antigen presentation to the immune system. Examples of cytokine therapy include, without limitation, interferons such as interferon-α, -β, and -γ, colony stimulating factors such as macrophage-CSF, granulocyte macrophage CSF, and granulocyte-CSF, interleukins such IL-1, IL-1a, IL-2, IL-3, IL-4, IL-5, IL-6, IL-7, IL-8, IL-9, IL-10, IL-11, and IL-12, tumor necrosis factors such as TNF-α and TNF-β. Agents that inactivate immunosuppressive targets can also be used, for example, TGF-beta inhibitors, IL-10 inhibitors, and Fas ligand inhibitors. Another group of agents include those that activate immune responsiveness to tumor or cancer cells, for example, those enhance T cell activation (e.g. agonist of T cell costimulatory molecules such as CTLA-4, ICOS and OX-40), and those enhance dendritic cell function and antigen presentation.

Kits

The present disclosure further provides kits comprising the bispecific polypeptide complex provided herein. In some embodiments, the kits are useful for detecting the presence or level of, or capturing or enriching one or more target of interest in a biological sample. The biological sample can comprise a cell or a tissue.

In some embodiments, the kit comprises the bispecific polypeptide complex provided herein which is conjugated with a detectable label. In certain other embodiments, the kit comprises an unlabeled bispecific polypeptide complex provided herein, and further comprises a secondary labeled antibody which is capable of binding to the unlabeled bispecific polypeptide complex provided herein. The kit may further comprise an instruction of use, and a package that separates each of the components in the kit.

In certain embodiments, the bispecific polypeptide complex provided herein are associated with a substrate or a device. Useful substrate or device can be, for example, magnetic beads, microtiter plate, or test strip. Such can be useful for a binding assay (such as ELISA), an immunographic assay, capturing or enriching of a target molecule in a biological sample.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1: Design and Engineering of Antibody and TCR Chimeric Proteins

TCR Sequences

TCRs are heterodimeric proteins made up of two chains. About 95% human T cells have TCRs consisting of alpha and beta chains. Considering that more crystal structures are available for beta chain TRBC1, TRBC1 sequences were chosen as the major backbone to design the polypeptide complex disclosed herein ("WuXiBody"). A typical amino acid sequence of TRBC1 can be found in Protein Data Bgank (PDB) structure 4L4T.

Interchain Disulphide-Bond of TCR

TCR crystal structures were used to guide our WuXiBody design. Unlike native TCR anchored on the membrane of T cell surface, soluble TCR molecules are less stable, although its 3D structure is very similar to antibody Fab. As a matter of fact, the instability of TCR in soluble condition used to be a big obstacle that prevents the elucidation of its crystal structure (Wang 2014, supra). We adopted a strategy of introducing a pair of Cys mutations in the TCR constant region and found it can significantly improve chain assembly and enhance expression.

Figures 2A, 2B, 2C, 2D:
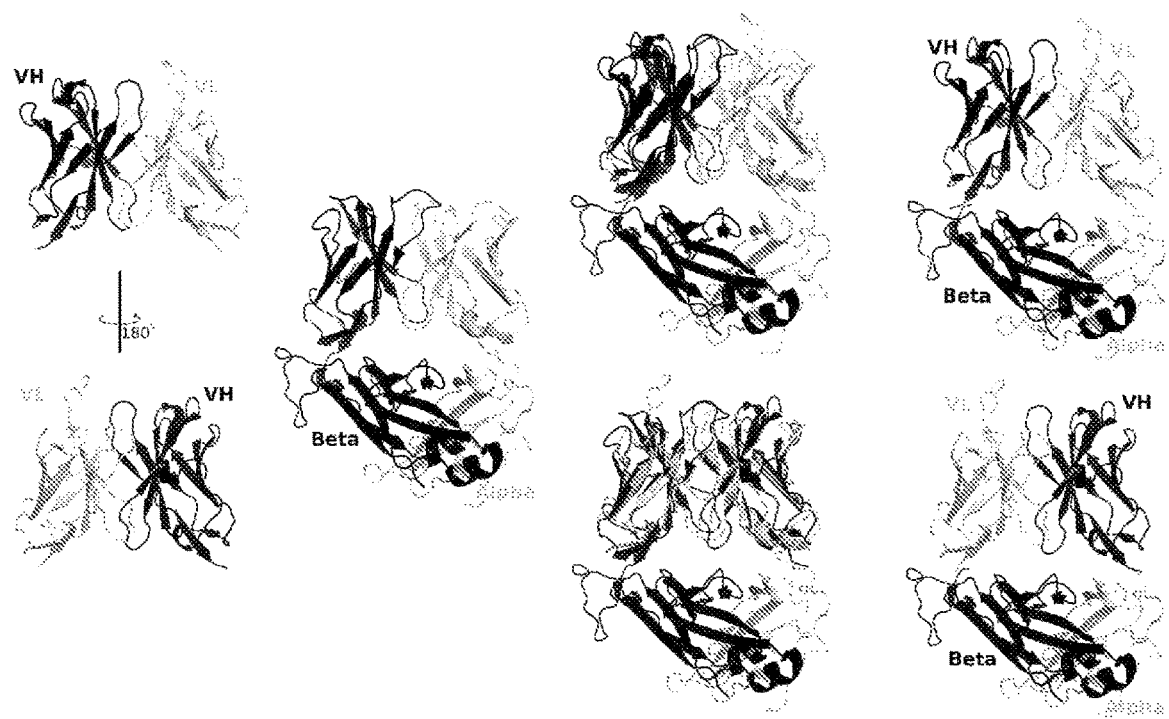
FIGS. 2A-2D present superimposed poses of antibody Fv model and TCR structure providing guidance in fusing antibody Fv and TCR constant region.

The conjunctions connecting antibody variable and TCR constant domains, their relative fusion orientations, as well as the Fc-connecting conjunctions were all carefully fine-turned to make a stable and functional WuXiBody. As TCR structure is very similar to antibody Fab, we superimposed the antibody Fv homology model on TCR variable region (PDB 4L4T, FIG. 2). The superimposed structure indicates that antibody Fv is structurally compatible with TCR constant domain. Based on this structural alignment and corresponding sequences, all the relevant engineering parameters were designed. Suitable conjunction regions are declosed in Example 2.

Example 2: Bispecific Anti-CD13×CD19 WuXiBody

Generation of Cynomolgus Monkey CD19 Expressing Cell Line

The gene of full length human or cynomolgus monkey CD19 was cloned into pcDNA3.3 vector. Each expression vector was then transfected into CHO-K1 cells respectively using Lipofectamine 2000. The cells were cultured in F12-K with 10% FBS. Blasticidin was added 24-48 hours after transfection. After two to three passages of selection, the cells were enriched by PE conjugated anti-CD19 antibody and Anti-PE Microbeads (Miltenyi-013-048-801). Stable single cell clones were isolated by limiting dilution and screened by FACS using anti-CD19 antibody.

Target-Expressing Tumor Lines

Raji and Jurkat cells were from ATCC. Ramos cell was from ECACC. All the tumor cells were cultured in RPMI1640/10% FBS.

Generation of WuXiBody W3438-T3U4.E17-1.uIgG4.SP and W3438-T3U4.F16-1.uIgG4.SP

The VL, VH, Ck, CH1 genes were amplified by PCR from existing in-house DNA templates. CAlpha and CBeta genes were synthesized by Geneweiz Inc. Anti CD19 Native or Anti CD3 chimeric light chain genes were inserted into a linearized vector containing a CMV promoter and a kappa signal peptide. The DNA fragments of Anti CD3 VH-CBeta were inserted into a linearized vector containing human IgG4S228P constant region CH2-CH3 with a knob mutation. The DNA fragments of Anti CD19 VH—CH1 were inserted into a linearized vector containing human IgG4S228P constant region CH2-CH3 with a hole mutation. The vector contains a CMV promoter and a human antibody heavy chain signal peptide.

Expression and Purification of W3438-T3U4.E17-1.uIgG4.SP and W3438-T3U4.F16-1.uIgG4.SP Heavy chain and light chain expression plasmids were co-transfected into Expi293 cells using Expi293 expression system kit (ThermoFisher-A14635) according to the manufacturer's instructions. Five days after transfection, the supernatants were collected and the protein was purified using Protein A column (GE Healthcare-17543802) and further size exclusion column (GE Healthcare-17104301). Antibody concentration was measured by Nano Drop. The purity of proteins was evaluated by SDS-PAGE and HPLC-SEC.

Target Binding by FACS

The binding of bi-specific antibodies to CD3- and CD19-expressing cells was evaluated using Jurkat and Ramos, respectively. A non-relevant antibody was used as an isotype control. Cells were spread in 96-well plates (Corning-3799) at a density of $10^5$ cells/well and washed with PBS/1% BSA. The antibodies were serial-diluted and incubated with cells at 4° C. for 1 hr. PE-conjugated goat anti-human IgG Fc Antibody (Jackson-109-115-098) was used for detection. After washing and resuspending, cells were analyzed by flow cytometry (Canto II, BD Biosciences). Data were analyzed using FlowJo software. Four-parameter non-linear regression analysis was used to calculate $EC_{50}$ values using Prism GraphPad Software.

Binding to Cynomolgus CD3

The binding of the CD3×CD19 bispecific antibody to cynomolgus CD3 were tested by protein binding ELISA. 96-well high protein binding ELISA plates (Nunc MaxiSorp, ThermoFisher, Thermo-442404) were coated overnight at 4° C. with 100 ul of 1 μg/ml Cynomolgus CD3 epsilon protein (Acro, #CDE-05226) in Carbonate-bicarbonate buffer (20 mM Na2CO3, 180 mM NaHCO$_3$, PH9.2). All wells were washed one time with 300 μL per well of PBS/0.5% Tween-20 (v/v). The wells were then blocked for one hour at room temperature with 200 μL per well of PBS/2% BSA (BOVOGEN, #BSAS) and washed three times with 300 μL per well of PBS/0.5% Tween-20 (v/v). For the primary antibody binding, CD3×CD19 bispecific antibody serially diluted in PBS/2% BSA were added to the relevant wells and incubated at room temperature for two hours. Plates were washed three times like before prior to the addition of 100 ul of 100 ng/ml secondary antibody Goat-anti-human IgG Fc-HRP (Bethyl, #A80-304P). Plates were incubated at room temperature for one hour, followed by six washes as described above. For the binding detection, 100 ul Tetramethylbenzidine (TMB) Substrate solution (Sigma-860336) was added to all wells for 10 minutes at room temperature in the dark before stopping the reaction with 100 ul 2M HCl. The extent of bispecific antibody binding to cynomolgus CD3 was determined by measuring the OD450 absorbance using the SpectraMax® M5e microplate reader. Wherever appropriate, binding $EC_{50}$ values were obtained by the four-parameter non-linear regression analysis using GraphPad Prism5 software.

Binding to Cynomoglus CD19

Binding of the CD3×CD19 bispecific antibody to cynomoglus CD19 target protein expressed on CHOK1 cells was determined by flow cytometry analysis. In brief, cynomoglus CD19 over-expressed stable cell line (WBP701.CHOK1.cPro1.C9, WuXi Biologics) were harvested with trypsin and diluted to $1\times10^6$ cells/ml in 1% BSA/1×PBS. $1\times10^5$ cells/well (100 ul) were added to each well of a 96-well U-plate (Corning, #3799) and centrifuged at 1500 rpm (Eppendorf, #5810R) for 5 minutes before removing the supernatant. Antibodies serially diluted in 1% BSA/1×PBS were added at 100 ul/well to the pelleted cells and incubated at 4° C. for 1 hour. A non-related hIgG4 antibody was used as an isotype control. Cells were washed two times with 180 ul/well of 1% BSA/1×PBS by centrifugation at 1500 rpm for 5 minutes at 4° C. Pelleted cells were resuspended in 100 ul/well Fluorescence-labeled anti-human IgG Fc antibody (Jackson, #109-115-098) 1:150 diluted in 1% BSA/1×PBS for 30 minutes at 4° C. in the dark. Cells were then washed two times as described above. After the final wash, cells were resuspended in 80 ul 1% BSA/1×PBS and fluorescence values were measured with a FACS Canto II cytometer (BD Biosciences). The amount of cell surface bound anti-CD19&CD3 bispecific antibody was assessed by measuring the mean fluorescence (MFI). The FACS raw data were analyzed by FlowJo software, wells containing no antibody or secondary antibody only were used to establish background fluorescence. Binding EC50 values were obtained by the four-parameter non-linear regression analysis using GraphPad Prism 5 software.

Affinity by FACS

Binding affinity to CD3 and CD19 was determined by flow cytometry using Jurkat and Ramos cells, respectively. The cells were transferred in to 96-well U-bottom plates (BD) at a density of $5\times10^4$ cells/well. Antibodies to be tested were 1:2-fold serially diluted in 1% 1×PBS/1% BSA and incubated with cells at 4° C. for 1 hr. Then, the plates were centrifuged at 1500 rpm for 4 mins and the supernatant discarded. The secondary antibody, Alexa647 conjugated goat anti-human IgG Fc (Jackson, Cat #109-605-098) or FITC conjugated goat anti-His (Bethyl, Cat # A190-113F) was added to re-suspended cells and incubated at 4° C. in the dark for 30 min. The cells were washed once and re-suspended in 100 μL 1×PBS/1% BSA. Fluorescence intensity was measured by flow cytometry (BD Canto II) and analyzed by FlowJo. Fluorescence intensity was converted to bound molecules/cell based on the quantitative beads (Quantum™ MESF Kits, Bangs Laboratories). $K_D$ was calculated by Graphpad Prism5.

Dual-Binding on Target Cells

The ability of bispecific antibodies to bridge CD3 T cells and CD19 B cells was tested by FACS. Jurkat cells and Raji cells were pre-labeled separately with 20 nM CellTrace Far Red (Invitrogen-C34564) and 50 nM Calcein-AM (Invitrogen-C3099) at 37° C. for 30 min, at a density of $1*10^6$ cells/ml. The pre-labeled cell pellets were washed twice with PBS/1% BSA, then mixed 1:1 to a final density of $1*10^6$ cells/ml. The cell mixture was centrifuged and resuspended with 10 nM antibody followed by 1 hr incubation. The cell mixture was analyzed by flow cytometry immediately after incubation. Bridging percentage was calculated as the percentage of events that are simultaneously labeled Far-Red and Calcein.

Cytotoxicity Assay

Peripheral Blood Mononuclear Cells (PBMCs) were freshly isolated by Ficoll-Paque PLUS (GE Healthcare-17-1440-03) density centrifugation from heparinized venous blood. Then obtained PBMCs were passed through EasySep (Stemcell-19053) columns for the enrichment of CD8+ T cells, which were used as effector cells. The efficacy of the antibodies to mediate tumor cell lysis by CD8+ T cells was determined by flow cytometry. In the cyotoxicity assay, Raji CD19 B cells as target cells were pre-labeled with 20 nM CellTrace Far Red (Invitrogen-C34564) at 37° C. for 30 min followed by washing the cell pellets twice with phenol-free RPMI 1640 (Invitrogen-11835030) supplemented with 1% FBS. Far Red-stained Raji (20000 cells per well) was incubated in 96-well round-bottom plate (Corning-3799) with isolated CD8+ T cells (effector/target cells ratio 5:1) and serial-diluted antibodies at 37° C. for 4 h. Following incubation, 3 µM Propidium Iodide (PI, Invitrogen-P3566) was mixed thoroughly for identifying dead cells. After 15 min, cells were analyzed by flow cytometry using a FACSCanto II cytometer. The Ab-mediated cytotoxicity can be defined as the PI-positive target cells percentage in Far Red-positive target cells. EC50 of the cytotoxicity was determined using Prism.

T Cell Activation Assay—Secreted Cytokine TNFα and IFN

Whether T cells were activated was reflected by the quantity of TNFα and IFN secreted to supernatant. The isolation procedure of CD4 and CD8 positive T cells was described in Section "T Cell Activation (Intracellular Cytokine TNFα & IFN Staining)". The mixture of Raji human B cells ($2*10^4$ cells/well), CD4 or CD8 T cells ($1*10^5$ cells/well), and antibodies was co-incubated at 37° C. for 24 h. The supernatant was collected followed by centrifuging the reaction mixture at 1500 rpm for 5 min. The quantity of TNFα and IFN in the supernatant was determined by Human TNF ELISA Set (R&D-DY210) and Human IFN ELISA Set (Capture Ab: Thermo Fisher-M700A, Detection Ab: Thermo Fisher-M701B, Standard substance: PEROTECH-300-02) respectively.

The procedure of sandwich ELISA was as follows. 96-well high protein binding ELISA plates (ThermoFisher-442404) were coated overnight at 4° C. or room temperature with 50 µl/well capture antibody in Carbonate-bicarbonate buffer (20 mM Na2CO3, 180 mM NaHCO$_3$, pH 9.2) according to the kit specifications. All wells were washed three times with 300 µl per well of PBS/0.5% Tween-20 (v/v) and all the following wash steps in the assay were performed the same. The wells were then blocked for one hour with PBS/2% BSA (BovoGen Biologicals-BSAS) for TNFα and 100% casein (Pierce-37528) for IFN then washed three times, followed by binding of collected supernatant above or standard substance (50 µl/well) for 1 hour at room temperature and three washes afterwards. For the detection antibody binding, corresponding antibodies diluted in PBS/2% BSA for TNFα and 50% casein for IFN were added to the relevant wells and incubated at room temperature for two hours.

Plates were washed three times prior to the addition of 50 µl of secondary antibody SA-HRP. Plates were incubated at room temperature for one hour, followed by six washes as described above. For the binding detection, 50 µl Tetramethylbenzidine (TMB) Substrate solution (Sigma-860336) was added to all wells for 10 minutes before stopping the reaction with 50 µl 2M HCl. The quantity of TNFα and IFN was determined by measuring the OD450 absorbance using the SpectraMax® M5e microplate reader.

T Cell Activation Assay—Surface Marker CD25 and CD69 Expression

Whether T cells were activated was reflected by staining signals of surface receptors CD25 and CD69. The isolation procedure of CD4 and CD8 positive T cells was described in Section "T Cell Activation (Intracellular Cytokine TNFα & IFN Staining)". The mixture of Raji human B cells ($2*10^4$ cells/well), CD4 or CD8 T cells ($1*10^5$ cells/well), and antibodies was co-incubated at 37° C. for 24 h. Following washing once with 1% BSA, the cell pellets were resuspended with staining buffer containing FITC Mouse Anti-human CD4 (BD-550628) or PerCpCy5.5 Mouse Anti-human CD8 (BD-560662), PE Mouse Anti-human CD69 (BD-560968) and APC Mouse Anti-human CD25 (BD-555434), followed by a 30 min incubation at 4° C. After washing cells twice, the percentage of PE and APC positive cells in FITC or PerCpCy5.5 positive cells was determined by flow cytometry.

Thermal Stability (DSF)

Melting temperature (Tm) of antibodies was investigated using QuantStudio™ 7 Flex Real-Time PCR system (Applied Biosystems). 19 µL of antibody solution was mixed with 1 µL of 62.5×SYPRO Orange solution (Invitrogen) and transferred to a 96 well plate (Biosystems). The plate was heated from 26° C. to 95° C. at a rate of 0.9° C./min, and the resulting fluorescence data was collected. The negative derivatives of the fluorescence changes with respect to different temperatures were calculated, and the maximal value was defined as melting temperature Tm. If a protein had multiple unfolding transitions, the first two Tm were reported, named as Tm1 and Tm2. Data collection and Tm calculation were conducted automatically by the operation software.

Serum Stability

Human blood was freshly collected from selected donors to polystyrene tubes without anticoagulant. Following 30 min's standing at room temperature, the human blood was centrifuged at 4000 rpm for 10 min to collect the serum layer. The centrifugation step was repeated until the serum was clarifying. Antibodies were mixed under detection with collected serum at the ratio of 1:9, and aliquots were drawn at 37° C. for the indicated times: 0 day, 1 day, 4 days, 7 days and 14 days. The samples were quick-frozen at different time points in liquid nitrogen and stored at −80° C. until use. The samples were analyzed by FACS to assess the binding ability on Jurkat CD3 T cells and Ramos CD19 B cells by comparison with that of corresponding antibodies without serum treatment.

Fcγ Receptor Binding Affinity by SPR

Antibody binding affinity to FcγRs was detected using Biacore T200 (or Biacore 8K). Each receptor was captured on an anti-his antibody immobilized CM5 sensor chip (GE). Antibodies at different concentrations were injected over the sensor chip at a flow rate of 30 uL/min for an association phase of 60 s, followed by 60 s dissociation. The chip was then regenerated by 10 mM glycine (pH 1.5) after each binding cycle.

The sensorgrams of blank surface and buffer channel were subtracted from the test sensorgrams. The experimental data was fitted by 1:1 model using Langmiur analysis (for FcγRI) or steady state model (for other receptors). A molecular weight of 150 KDa was used to calculate the molar concentration of antibodies.

C1q Binding by ELISA

ELISA Plates (Nunc) were coated with antibody samples at 3 μg/mL overnight at 4° C. After blocking and washing, C1q was gradient diluted starting from 600 μg/mL and incubated at room temperature for 2 hr. The plates were then washed and subsequently incubated with sheep anti-human C1q Ab-HRP for 1 hr. After washing, TMB substrate was added and the interaction was stopped by 2 M HCl. The absorbance at 450 nm was read using a microplate reader (Molecular Device).

FcRn Binding Affinity by SPR

Antibody binding affinity to FcRn was detected using Biacore T200 (or Biacore 8K). Each antibody was immobilized on CM5 sensor chip (GE). FcRn at different concentrations in running buffer (50 mM Na2HPO4/NaH2PO4, 150 mM NaCl, 0.05% Tween20, pH 6.0) were injected over the sensor chip at a flow rate of 30 uL/min for an association phase of 60 s, followed by 60 s dissociation. The chip was then regenerated by 1×PBS (pH 7.4) after each binding cycle.

The sensorgrams of blank surface and buffer channel were subtracted from the test sensorgrams. The experimental data was fitted by steady state model. Molecular weight of 45 KDa was used to calculate the molar concentration of FcRn.

Efficacy Study in Murine Raji/PBMC Model

The Raji tumor cells (ATCC® CCL-86™) were maintained in vitro as a monolayer culture in RPMI-1640 medium supplemented with 10% fetal bovine serum, 100 U/ml penicillin and 100 μg/ml streptomycin at 37° C. in an atmosphere of 5% $CO_2$ in air. The tumor cells were routinely subcultured twice weekly. The cells growing in an exponential growth phase were harvested and counted for tumor inoculation.

Human PBMCs were isolated from heparin whole blood by using Ficoll-Paque Plus per manufacturer's instructions.

Each mouse was co-inoculated subcutaneously at the right flank with Raji tumor cells mixed with Matrigel and fresh PBMC in 0.2 ml of PBS on D0. Antibodies injection was conducted from D3 (i.v. BIW×4 times).

Testing Article Preparation

Tumor Measurements and Endpoints

The major endpoint was to see if the tumor growth could be delayed or mice could be cured. Tumor size was measured twice weekly in two dimensions using a caliper, and the volume was expressed in $mm^3$ using the formula: $V=0.5 \, a \times b^2$ where a and b are the long and short diameters of the tumor, respectively. The T/C value (in percent) is an indication of antitumor effectiveness.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Cynomolgus PK, Toxicity and Immunogenicity

One male and one female cynomolgus monkeys were were administered with WBP3438 at 1 mg/kg once by intravenous bolus administration. The formulations were formulated in 20 mM NaAc—HAc, 7.0% (w/w) Sucrose, 0.02% (w/v) PS80, pH5.0. PK blood samples were collected at pre-dose (Day-1), 0.25 h, 0.5 h, 1 h, 4 h, 8 h, 24 h, Day 3, Day 7, Day 14, Day 21 and Day 28. Antidrug antibody (ADA) samples were collected at 3 d, 14 d (312 h) and 28 d (480 h).

Serum concentrations of WBP3438 and ADA in serum samples were determined by ELISA. The serum concentration of WBP3438 in monkeys was subjected to a non-compartmental pharmacokinetic analysis by using the Phoenix WinNonlin software (version 6.3, Pharsight, Mountain View, Calif.). The linear/log trapezoidal rule was applied in obtaining the PK parameters.

Cage-side observations for general health and appearance, especially skin irritation was observed. Whole blood sample analysis for hematology (CBC) and serum analysis for chemistry detection were determined by hematology analyzer (ADVIA2120) and chemistry (HITACHI 7180), respectively.

Results

Generation of Cynomolgus CD19 Expressing Cell Line

Figure 5:
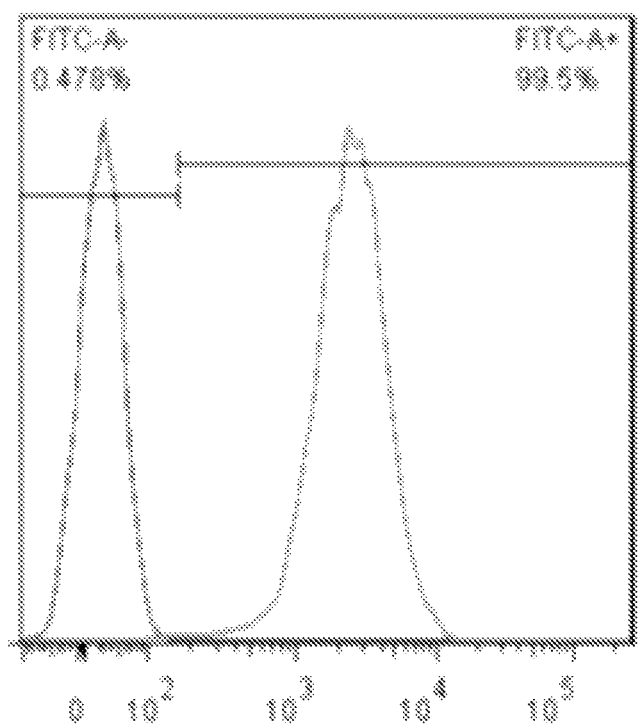
FIG. 5 shows flow cytometry histograms of cynomolgus-CD19 transfected cell line WBP701.CHO-K1.cpro1.FL.C9 and CHO-K1 parental cell line.

The expression of cynomolgus CD19 expressing cell line WBP701.CHO-K1.cpro1.FL.C9 was detected using anti-CD19 antibody by flow cytometry. WBP701.CHO-K1.cpro1.FL.C9 showed high expression of monkey CD19 (FIG. 5).

WuXiBody Generation and Optimization

FIG. 1 presents schematic representations of studied antibodies and formats. Both anti-CD3 antibody T3 and anti-CD19 antibody U4 were developed. The constant region (CL and CH1) of T3 was replaced by the constant domain of TCR to design unique light-heavy chain interface that is orthogonal to regular antibody. The TCR-modified T3 and native U4 in conjunction with "knobs-into-holes" mutations in Fc domain were used to design bispecific antibody format E17 and F16.

Variable heavy chain and light chain sequences of anti-CD3 and anti-CD19 binding moieties from W3438-T3U4.E17-1.uIgG4. SP and W3438-T3U4.F16-1.uIgG4. SP are provided below:

| Compounds | Package | Preparation | Conc. mg/ml |
|---|---|---|---|
| Isotype control | 9.38 mg/ml | 0.031 ml solution + 1.908 ml PBS | 1.5 |
| W3438-T3U4.E17-1.uIgG4.SP | 2.6 mg/ml | B: 0.138 ml solution + 2.254 ml PBS | 1.5 |
| W3438-T3U4.E17-1.uIgG4.SP | | B1: 0.450 ml B + 1.800 ml PBS | 0.3 |
| W3438-T3U4.E17-1.uIgG4.SP | | B2: 0.450 ml B1 + 1.800 ml PBS | 0.06 |

| | | | |
|---|---|---|---|
| W3438-<br>T3U4.E17-<br>1.uIgG4.SP<br>& W3438-<br>T3U4.F16-<br>1.uIgG4.SP | anti-CD3<br>antibody<br>VH | DNA sequence<br>(SEQ ID NO: 16) | CAGGTGCAGCTTGTGCAGTCTGGGGCAGAAGTG<br>AAGAAGCCTGGGTCTAGTGTCAAGGTGTCATGC<br>AAGGCTAGCGGGTTCGCCTTTACTGACTACTACA<br>TCCACTGGGTGCGGCAGGCTCCCGGACAAGGGT<br>TGGGAGTGGATGGGATGGATCTCCCCAGGCAATG<br>TCAACACAAAGTACAACGAGAACTTCAAAGGC<br>CGCGTCACCATTACCGCCGACAAGAGCACCTCC<br>ACAGCCTACATGGAGCTGTCCAGCCTCAGAAGC<br>GAGGACACTGCCGTCTACTACTGTGCCAGGGAT<br>GGGTACTCCCTGTATTACTTTGATTACTGGGGCC<br>AGGGCACACTGGTGACAGTGAGCTCC |
| | | Amino acid sequence<br>(SEQ ID NO: 15) | QVQLVQSGAEVKKPGSSVKVSCKASG<u>FAFTDYYI</u><br><u>H</u>WVRQAPGQGLEWMG<u>WISPGNVNTKYNENFKG</u><br>RVTITADKSTSTAYMELSSLRSEDTAVYYCAR<u>DG</u><br><u>YSLYYFDY</u>WGQGTLVTVSS |
| | anti-CD3<br>antibody<br>VL | DNA sequence<br>(SEQ ID NO: 18) | GATATCGTGATGACCCAGAGCCCAGACTCCCTTG<br>CTGTCTCCCTCGGCGAAAGAGCAACCATCAACT<br>GCAAGAGCTCCCAAAGCCTGCTGAACTCCAGG<br>ACCAGGAAGAATTACCTGGCCTGGTATCAGCAG<br>AAGCCCGGCCAGCCTCCTAAGCTGCTCATCTACT<br>GGGCCTCCACCCGGCAGTCTGGGGTGCCCGATC<br>GGTTTAGTGGATCTGGGAGCGGGACAGACTTCA<br>CATTGACAATTAGCTCACTGCAGGCCGAGGACG<br>TGGCCGTCTACTACTGTACTCAGAGCCACACTCT<br>CCGCACATTCGGCGGAGGGACTAAAGTGGAGAT<br>TAAG |
| | | Amino acid sequence<br>(SEQ ID NO: 17) | DIVMTQSPDSLAVSLGERATINC<u>KSSQSLLNSRTR</u><br><u>KNYLA</u>WYQQKPGQPPKLLIY<u>WASTRQS</u>GVPDRFS<br>GSGSGTDFTLTISSLQAEDVAVYYC<u>TQSHTLRT</u>FG<br>GGTKVEIK |
| | anti-CD19<br>antibody<br>VH | DNA sequence<br>(SEQ ID NO: 20) | CAAATGCAGCTCGTCCAGTCTGGACCTGAAGTG<br>AAGAAGCCCGGGACATCCGTCAAGGTCTCATGT<br>AAGGCTAGCGGGTACGCATTCACTTCCTACAAC<br>ATGTACTGGGTGCGCCAGGCCAGAGGACAGAG<br>GTTGGAGTGGATCGGCTACATCGACCCATACAA<br>CGCCGATACTACCTACAATCAGAAGTTTAAAGG<br>GCGGGTGACCATTACCCGGGATATGTCCACCTCC<br>ACCGCCTACATGGAGCTGAGCAGCCTGAGGAGC<br>GAGGACACAGCCGTGTACTACTGCCTGACAACA<br>GCCTATGCCATGGACTATTGGGGCCAGGGCACA<br>CTTGTGACTGTGAGCAGT |
| | | Amino acid sequence<br>(SEQ ID NO: 19) | QMQLVQSGPEVKKPGTSVKVSCKAS<u>GYAFTSYN</u><br><u>MY</u>WVRQARGQRLEWIG<u>YIDPYNADTTYNQKFKG</u><br>RVTITRDMSTSTAYMELSSLRSEDTAVYYCLT<u>TAYA</u><br><u>MDY</u>WGQGTLVTVSS |
| | anti-CD19<br>antibody<br>VL | DNA sequence<br>(SEQ ID NO: 22) | GACATCCAGCTCACCCAATCCCCTTCTTTCCTCT<br>CCGCAAGTGTCGGAGATAGGGTGACTATCACCT<br>GCTCAGCTTCTTCAACCGTGAACTACATGCATTG<br>GTACCAGCAGAAGCCCGGGAAAGCCCCAAAGC<br>TGCTGATCTACAGCACCTCCAATCTGGCCAGTGG<br>AGTGCCAAGCCGGTTTAGCGGGAGCGGCTCCGG<br>CACTGAATTCACTTTGACAATTAGCAGCCTTCAG<br>CCTGAGGACTTTGCCACATATTACTGTCACCAGT<br>GGTCCAGCTACCCCTACACATTCGGCAGGGCA<br>CAAAGCTGGAGATTAAG |
| | | Amino acid sequence<br>(SEQ ID NO: 21) | DIQLTQSPSFLSASVGDRVTITC<u>SASSTVNYMH</u>WY<br>QQKPGKAPKLLIY<u>STSNLAS</u>GVPSRFSGSGSGTEF<br>TLTISSLQPEDFATYYC<u>HQWSSYPYT</u>FGQGTKLEIK |

Full-length W3438-T3U4.E17-1.uIgG4.SP and W3438-
T3U4.F16-1.uIgG4.SP sequences are provided below:

| Antibody | Chain | Sequences |
|---|---|---|
| W3438-<br>T3U4.E17-<br>1.uIgG4.SP | T3-LC<br>(SEQ ID<br>NO: 26) | DIVMTQSPDSLAVSLGERATINCKSSQSLLNSRTRKNYLAWYQQKPGQP<br>PKLLIYWASTRQSGVPDRFSGSGSGTDFTLTISSLQAEDVAVYYCTQSHT<br>LRTFGGGTKVEIKPDIQNPDPAVYQLRDSKSSDKSVCLFTDFDSQTQVS<br>QSKDSDVYITDKCVLDMRSMDFKSNSAVAWSQKSDFACANAFQNSIIP<br>EDTFFPSPESS |
| | T3-HC<br>(SEQ ID<br>NO: 27) | QVQLVQSGAEVKKPGSSVKVSCKASGFAFTDYYIHWVRQAPGQGLEW<br>MGWISPGNVNTKYNENFKGRVTITADKSTSTAYMELSSLRSEDTAVYY<br>CARDGYSLYYFDYWGQGTLVTVLEDLKNVFPPEVAVFEPSEAEISHTQ<br>KATLVCLATGFYPDHVELSWWVNGKEVHSGVCTDPQPLKEQPALQDS<br>RYALSSRLRVSATFWQNPRNHFRCQVQFYGLSENDEWTQDRAKPVTQI<br>VSAEAWGRYGPPCPPCPAPEFLGGPSVFLFPPKPKDTLMISRTPEVTCVV<br>VDVSQEDPEVQFNWYVDGVEVHNAKTKPREEQFNSTYRVVSVLTVLH |

| Antibody | Chain | Sequences |
|---|---|---|
| | | QDWLNGKEYKCKVSNKGLPSSIEKTISKAKGQPREPQVYTLPPCQEEM TKNQVSLWCLVKGFYPSDIAVEWESNGQPENNYKTTPPVLDSDGSFFL YSRLTVDKSRWQEGNVFSCSVMHEALHNHYTQKSLSLSLGK |
| | U4-LC (SEQ ID NO: 28) | DIQLTQSPSFLSASVGDRVTITCSASSTVNYMHWYQQKPGKAPKLLIYS TSNLASGVPSRFSGSGSGTEFTLTISSLQPEDFATYYCHQWSSYPYTFGQ GTKLEIKRTVAAPSVFIFPPSDEQLKSGTASVVCLLNNFYPREAKVQWK VDNALQSGNSQESVTEQDSKDSTYSLSSTLTLSKADYEKHKVYACEVT HQGLSSPVTKSFNRGEC |
| | U4-HC (SEQ ID NO: 29) | QMQLVQSGPEVKKPGTSVKVSCKASGYAFTSYNMYWVRQARGQRLE WIGYIDPYNGDTTYNQKFKGRVTITRDMSTSTAYMELSSLRSEDTAVYY CLTTAYAMDYWGQGTLVTVSSASTKGPSVFPLAPCSRSTSESTAALGCL VKDYFPEPVTVSWNSGALTSGVHTFPAVLQSSGLYSLSSVVTVPSSSLG TKTYTCNVDHKPSNTKVDKRVESKYGPPCPPCPAPEFLGGPSVFLFPPK PKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKG QPREPQVCTLPPSQEEMTKNQVSLSCAVKGFYPSDIAVEWESNGQPEN NYKTTPPVLDSDGSFFLVSRLTVDKSRWQEGNVFSCSVMHEALHNHYT QKSLSLSLGK |
| W3438-T3U4.F16-1.uIgG4.SP | T3-LC (SEQ ID NO: 26) | DIVMTQSPDSLAVSLGERATINCKSSQSLLNSRTRKNYLAWYQQKPGQ PPKLLIYWASTRQSGVPDRFSGSGSGTDFTLTISSLQAEDVAVYYCTQS HTLRTFGGGTKVEIKPDIQNPDPAVYQLRDSKSSDKSVCLFTDFDSQT QVSQSKDSDVYITDKCVLDMRSMDFKSNSAVAWSQKSDFACANAFQ NSIIPEDTFFPSPESS |
| | T3-HC (SEQ ID NO: 27) | QVQLVQSGAEVKKPGSSVKVSCKASGFAFTDYYIHWVRQAPGQGLE WMGWISPGNVNTKYNENFKGRVTITADKSTSTAYMELSSLRSEDTAV YYCARDGYSLYYFDYWGQGTLVTVLEDLKNVFPPEVAVFEPSEAEISH TQKATLVCLATGFYPDHVELSWWVNGKEVHSGVCTDPQPLKEQPAL QDSRYALSSRLRVSATFWQNPRNHFRCQVQFYGLSENDEWTQDRAKP VTQIVSAEAWGRYGPPCPPCPAPEFLGGPSVFLFPPKPKDTLMISRTPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYTL PPCQEEMTKNQVSLWCLVKGFYPSDIAVEWESNGQPENNYKTTPPVL DSDGSFFLYSRLTVDKSRWQEGNVFSCSVMHEALHNHYTQKSLSLSL GK |
| | U4-LC (SEQ ID NO: 28) | DIQLTQSPSFLSASVGDRVTITCSASSTVNYMHWYQQKPGKAPKLLIY STSNLASGVPSRFSGSGSGTEFTLTISSLQPEDFATYYCHQWSSYPYTF GQGTKLEIKRTVAAPSVFIFPPSDEQLKSGTASVVCLLNNFYPREAKVQ WKVDNALQSGNSQESVTEQDSKDSTYSLSSTLTLSKADYEKHKVYAC EVTHQGLSSPVTKSFNRGEC |
| | U4-HC (SEQ ID NO: 30) | QMQLVQSGPEVKKPGTSVKVSCKASGYAFTSYNMYWVRQARGQRL EWIGYIDPYNGDTTYNQKFKGRVTITRDMSTSTAYMELSSLRSEDTAV YYCLTTAYAMDYWGQGTLVTVSSASTKGPSVFPLAPCSRSTSESTAAL GCLVKDYFPEPVTVSWNSGALTSGVHTFPAVLQSSGLYSLSSVVTVPSS SLGTKTYTCNVDHKPSNTKVDKRVGGGGSGGGGSQMQLVQSGPEVK KPGTSVKVSCKASGYAFTSYNMYWVRQARGQRLEWIGYIDPYNGDT TYNQKFKGRVTITRDMSTSTAYMELSSLRSEDTAVYYCLTTAYAMDY WGQGTLVTVSSASTKGPSVFPLAPCSRSTSESTAALGCLVKDYFPEPV TVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMIS RTPEVTCVVVDVSQEDPEVQFNWYVDGVEVHNAKTKPREEQFNSTY RVVSVLTVLHQDWLNGKEYKCKVSNKGLPSSIEKTISKAKGQPREPQ VCTLPPSQEEMTKNQVSLSCAVKGFYPSDIAVEWESNGQPENNYKTTP PVLDSDGSFFLVSRLTVDKSRWQEGNVFSCSVMHEALHNHYTQKSLS LSLGK |

Production of W3438-T3U4.F16-1.uIgG4.SP

Figure 6:
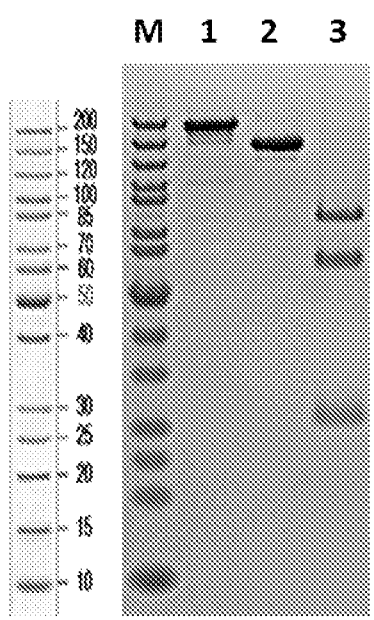
FIG. 6 shows SDS-PAGE of W3438-T3U4.F16-1.uIgG4.SP. M: Protein marker; Lane1: W3438-T3U4.F16-1.uIgG4. SP, non-reduced; Lane3: W3438-T3U4.F16-1.uIgG4. SP, reduced.
Figure 7:
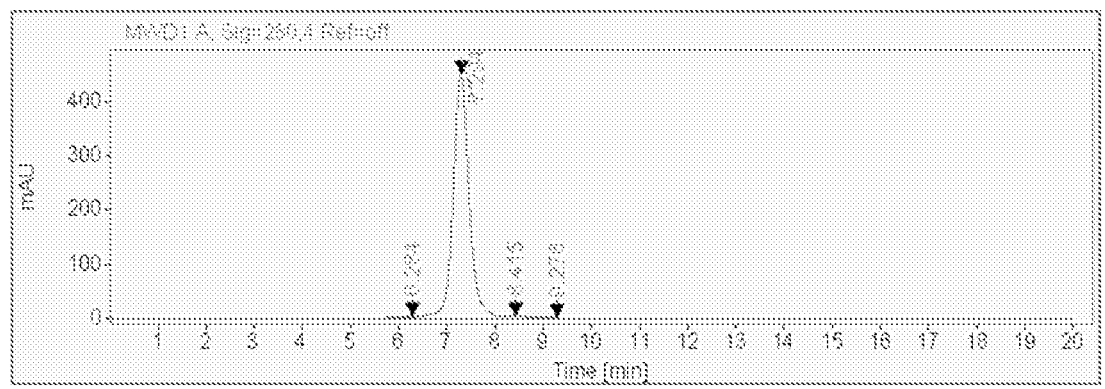
FIG. 7 shows SEC-HPLC chromatogram of W3438-T3U4.F16-1.uIgG4.

The expression titer of antibody W3438-T3U4.F16-1.uIgG4.SP is higher than 90 mg/L through transient expression. After 2-step purification, the purity of W3438-T3U4.F16-1.uIgG4.SP reaches 97.5% (SEC-HPLC, FIG. 7). W3438-T3U4.F16-1.uIgG4.SP migrates with the apparent molecular mass of 75 kDa, 55 kDa and 25 kDa on SDS-PAGE under reducing conditions, corresponding to the two heavy chains and two light chains. The two light chains may overlap due to similar molecular weights. The antibody migrates with the apparent molecular mass of 200 kDa under non-reducing condition indicating the intact bispecific molecule (FIG. 6).

Production of W3438-T3U4.E17-1.uIgG4.SP

Figure 8:
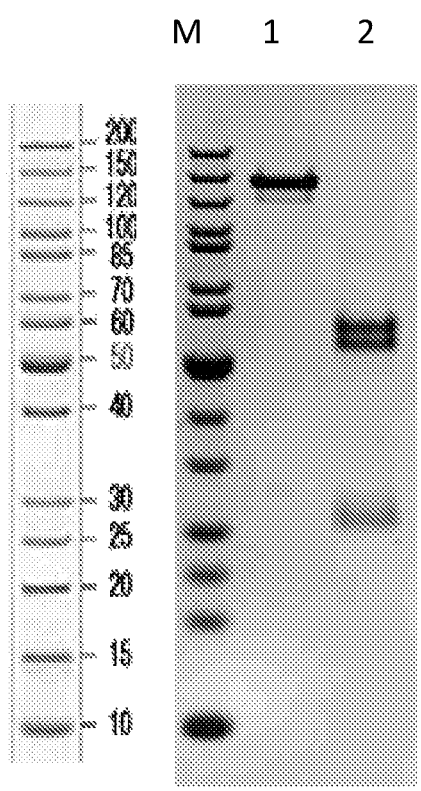
FIG. 8 shows SDS-PAGE of W3438-T3U4.E17-1.uIgG4.SP. M: Protein marker; Lane1: W3438-T3U4.E17-1.uIgG4.SP, non-reduced; Lane2: W3438-T3U4.E17-1.uIgG4.SP, reduced.
Figure 9:
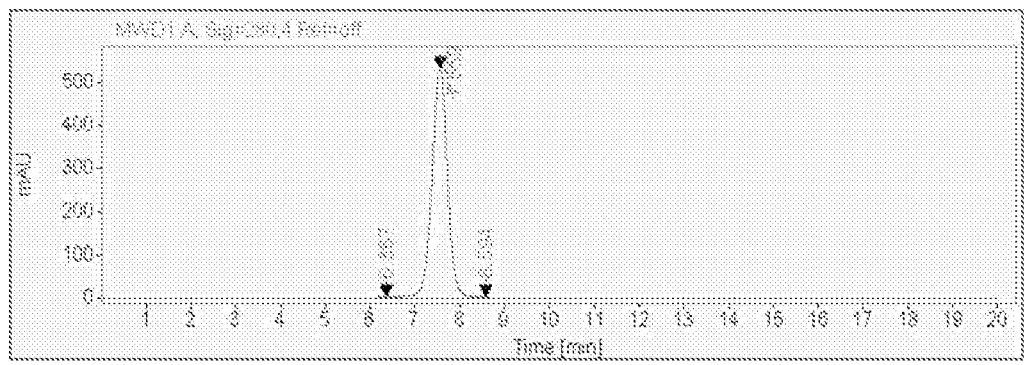
FIG. 9 shows SEC-HPLC chromatogram of W3438-T3U4.E17-1.uIgG4.SP.

The expression titer of antibody W3438-T3U4.E17-1.uIgG4.SP is higher than 100 mg/L through transient expression. After 2-step purification, the purity of W3438-T3U4.E17-1.uIgG4.SP reaches 95% (SEC-HPLC, FIG. 9). W3438-T3U4.E17-1.uIgG4.SP migrates with the apparent molecular mass of 54 kDa, 56 kDa and 25 kDa on SDS-PAGE under reducing conditions, corresponding to the two heavy chains and two light chains. The two light chains may overlap due to similar molecular weights. The antibody migrates with the apparent molecular mass of 150 kDa under non-reducing condition indicating the intact bispecific molecule (FIG. 8).

Target-Binding

Figure 10A:
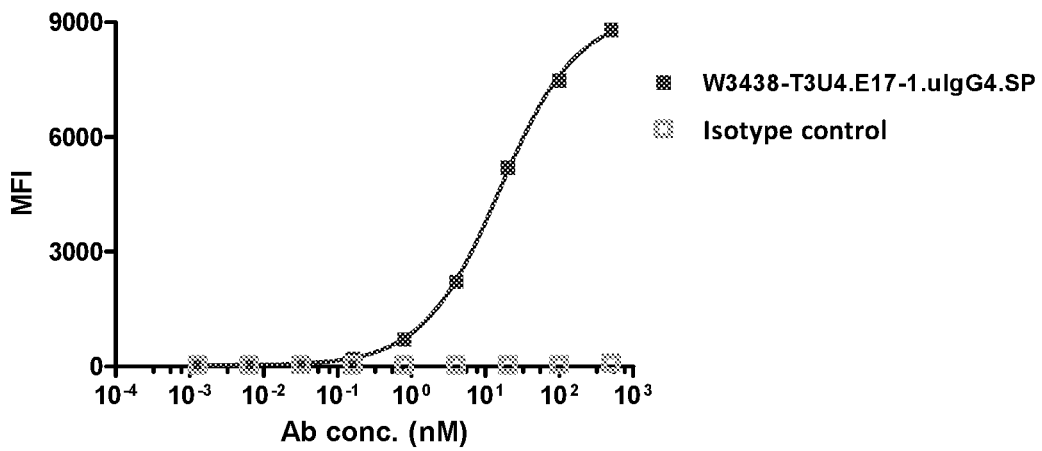
FIGS. 10A-10B show binding of W3438-T3U4.E17-1.uIgG4.SP to Ramos cells (FIG. 10A) and Jurkat cells (FIG. 10B) by FACS.
Figure 10B:
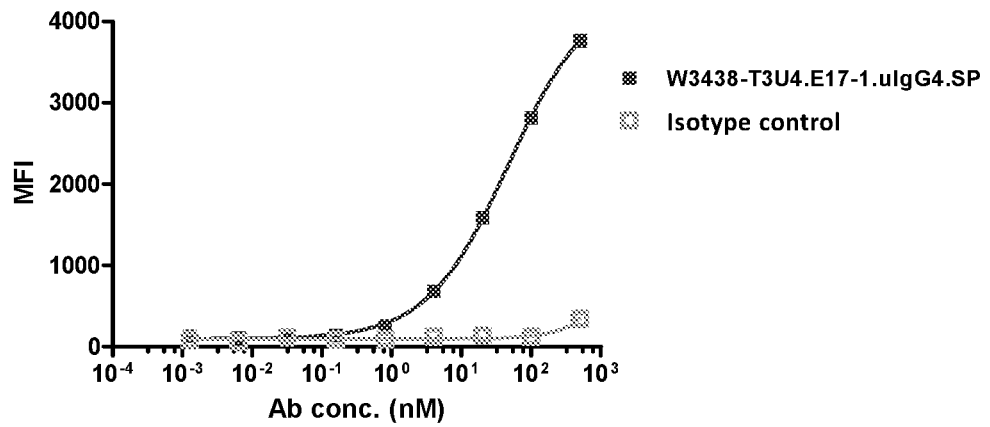

The binding of W3438-T3U4.E17-1.uIgG4.SP to CD19 and CD3 was tested on Ramos and Jurkat cells by flow cytometry (FIGS. 10A-10B). The antibody W3438-T3U4.E17-1.uIgG4. SP showed strong binding activities to Ramos and Jurkat cells, with $EC_{50}$ values of 15.6 nM and 47 nM respectively.

Figure 11A:
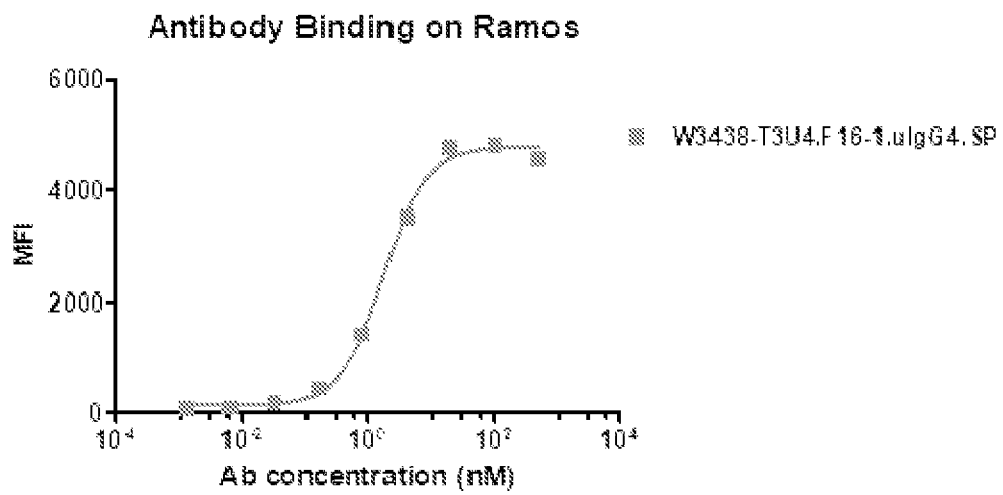
FIGS. 11A-11B show binding of W3438-T3U4.F16-1.uIgG4.SP to Ramos cells (FIG. 11A) and Jurkat cells (FIG. 11B) by FACS.
Figure 11B:
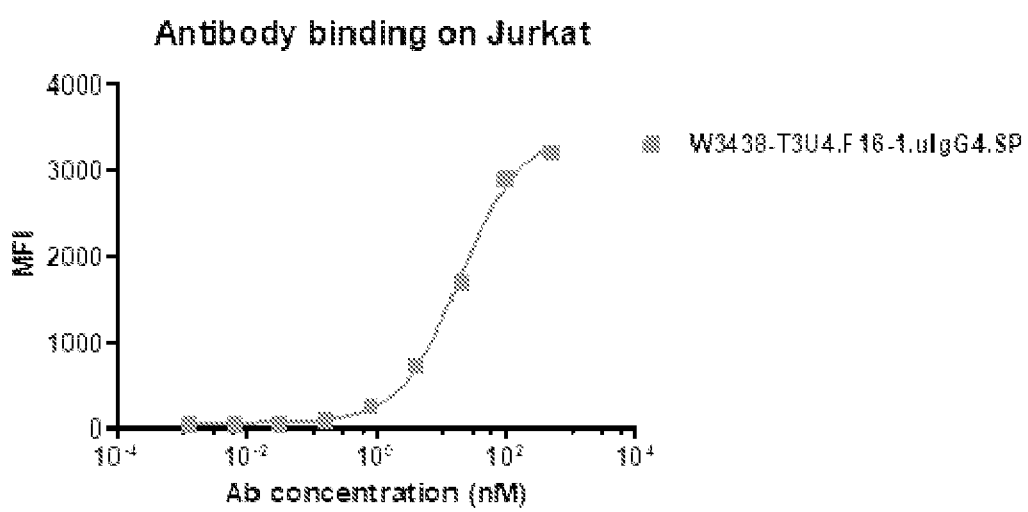

The binding of W3438-T3U4.F16-1.uIgG4.SP to CD19 and CD3 was tested on Ramos and Jurkat cells by flow cytometry (FIGS. 11A-11B). The antibody W3438-T3U4.F16-1.uIgG4.SP showed strong binding activities to Ramos and Jurkat cells, with $EC_{50}$ values of 1.8 nM and 19.3 nM respectively.

Cross Species Binding

Figure 12:
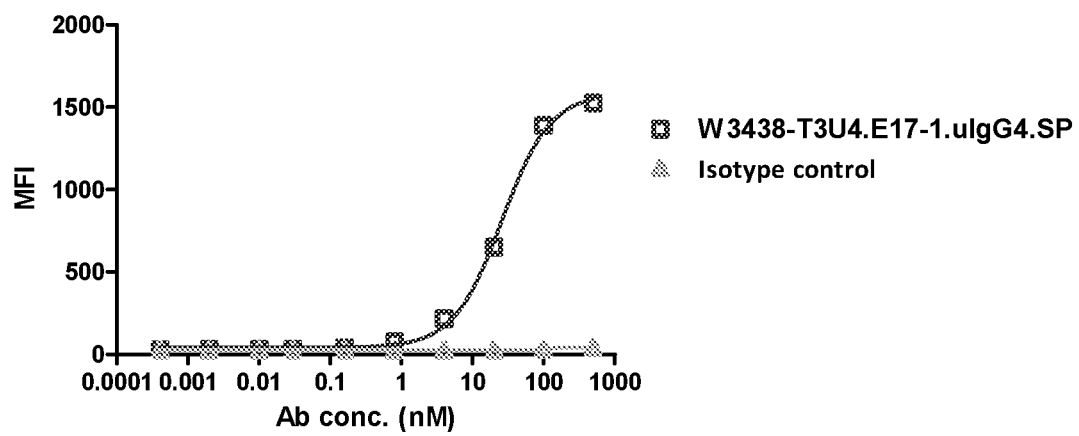
FIG. 12 shows binding of W3438-T3U4.E17-1.uIgG4.SP to cynomolgus CD19 expressing cell by FACS.
Figure 13:
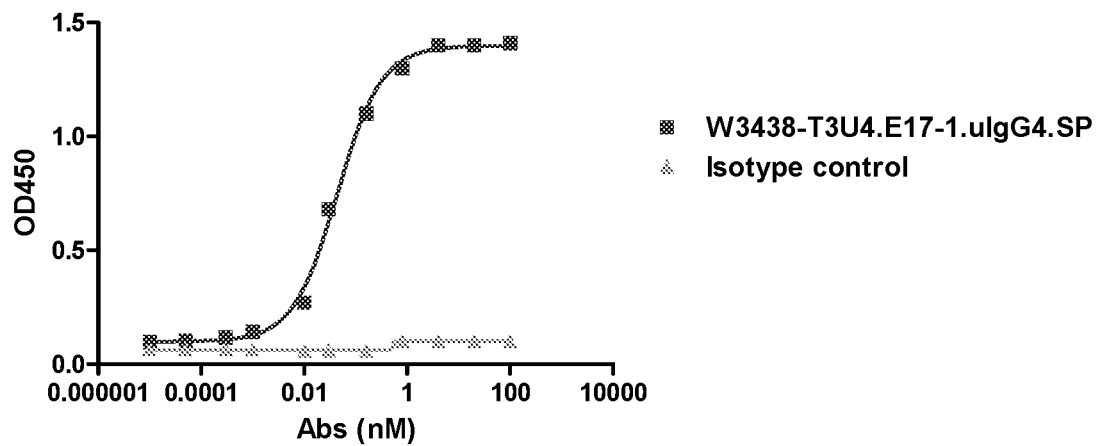
FIG. 13 shows binding of W3438-T3U4.E17-1.uIgG4.SP to cynomolgus CD3 by ELISA.

The binding of W3438-T3U4.E17-1.uIgG4.SP to cynomolgus CD19 was tested on WBP701.CHO-K1.cpro1.FL.C9 cell (CD19-expressing cell) by flow cytometry (FIG. 12). The binding $EC_{50}$ was 26 nM. The binding of W3438-T3U4.E17-1.uIgG4.SP to cynomolgus CD3 was tested using W331-cynoPro1.ECD.His (Cynomolgus CD3 epsilon protein) by ELISA (FIG. 13). The binding $EC_{50}$ was 0.04 nM.

Affinity to Target Cells

Figure 14A:
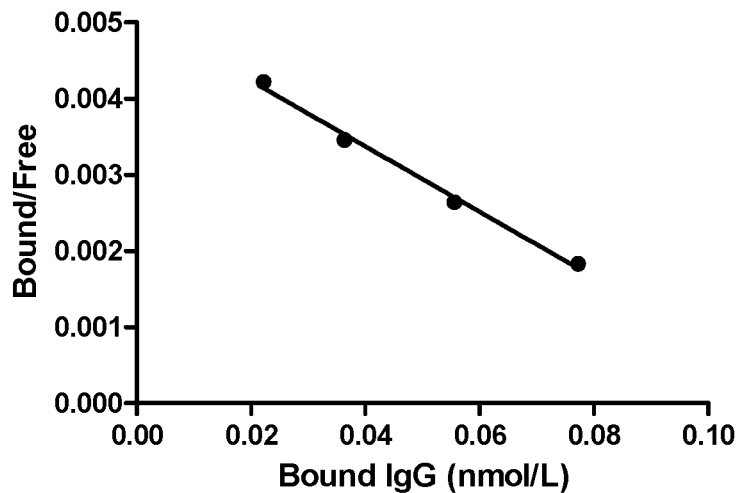
FIGS. 14A-14B show affinity of W3438-T3U4.E17-1.uIgG4.SP to human CD19 and CD3 as measured by binding to Ramos (FIG. 14A) and Jurkat (FIG. 14B) cells.
Figure 14B:
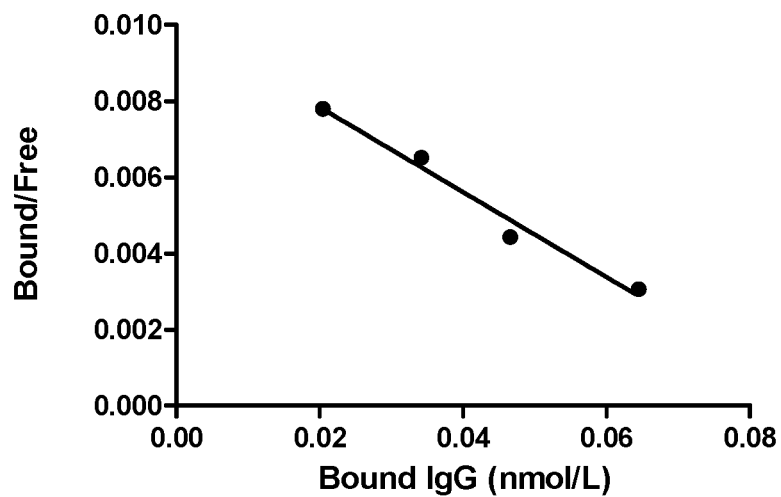
Figure 17A:
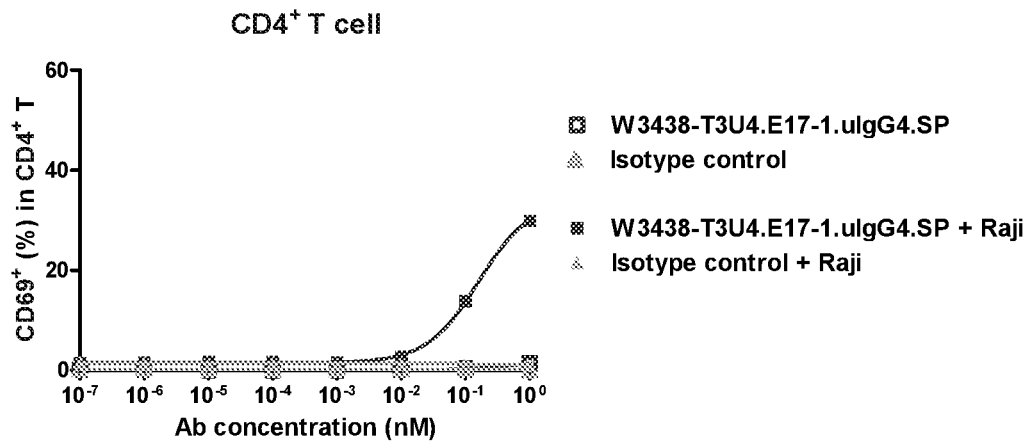
FIGS. 17A-17D show CD69 and CD25 expression on T cell in the presence or absence of CD19+ target cells. Percentage of CD69 expression T cell in CD4+ T cell subset (FIG. 17A); Percentage of CD69+ expression T cell in CD8+ T cell subset (FIG. 17B); Percentage of CD25 expression T cell in CD4+ T cell subset (FIG. 17C); Percentage of CD25 expression T cell in CD8+ T cell subset (FIG. 17D).
Figure 17B:
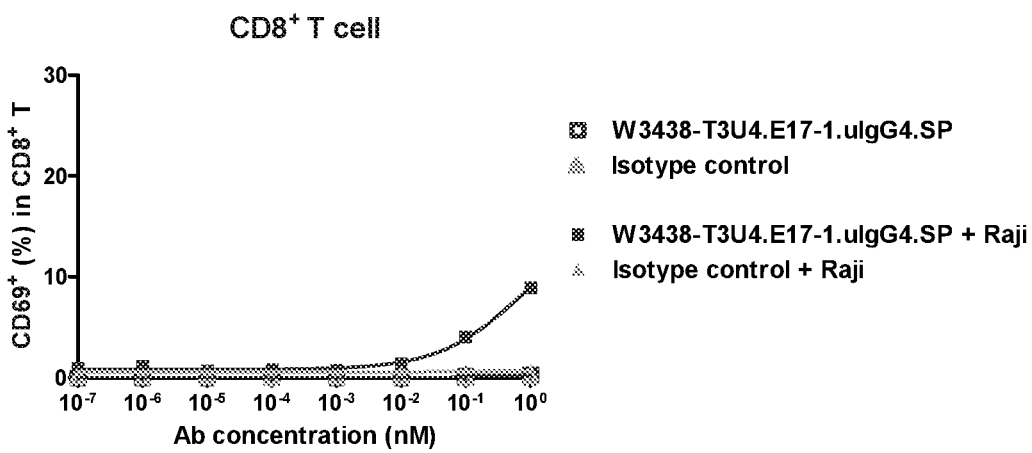
Figure 17C:
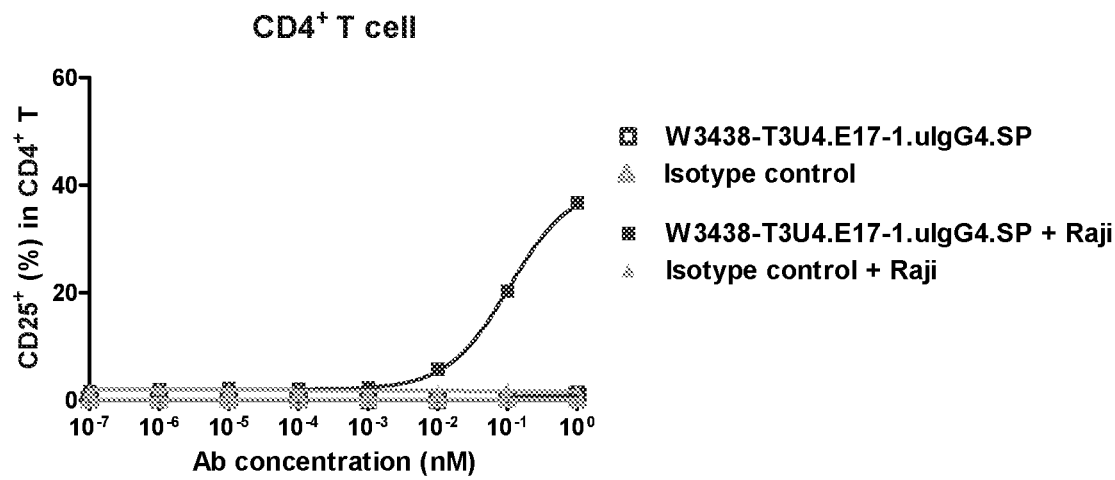
Figure 17D:
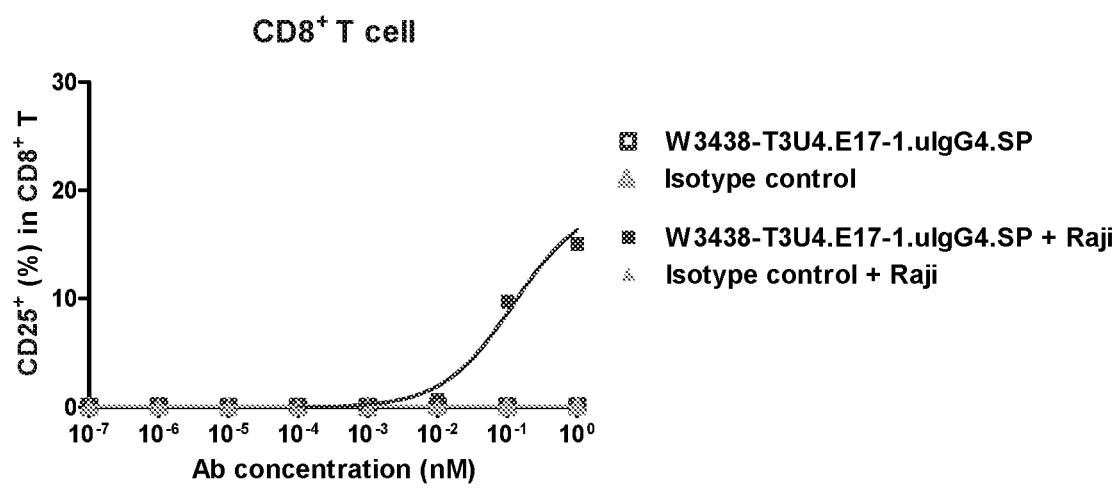
Figure 18A:
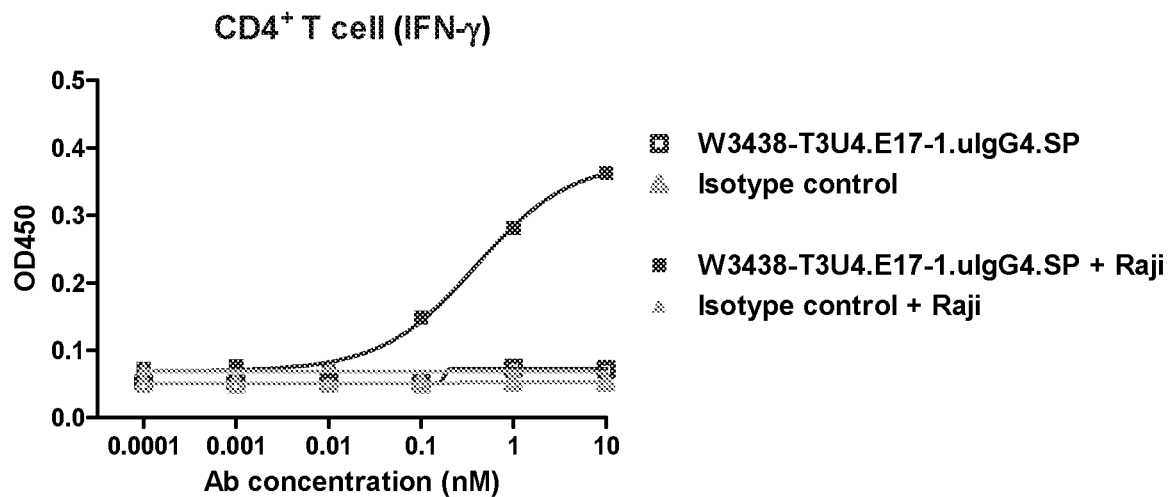
FIGS. 18A-18D show IFN-γ and TNF-α cytokine release of T cell in the presence or absence of CD19+ target cells. Release of IFN-γ in CD4+ T cell subset (FIG. 18A); Release of TNF-α in CD4+ T cell subset (FIG. 18B); Release of IFN-γ in CD8+ T cell subset (FIG. 18C); Release of TNF-α in CD8+ T cell subset (FIG. 18D).
Figure 18B:
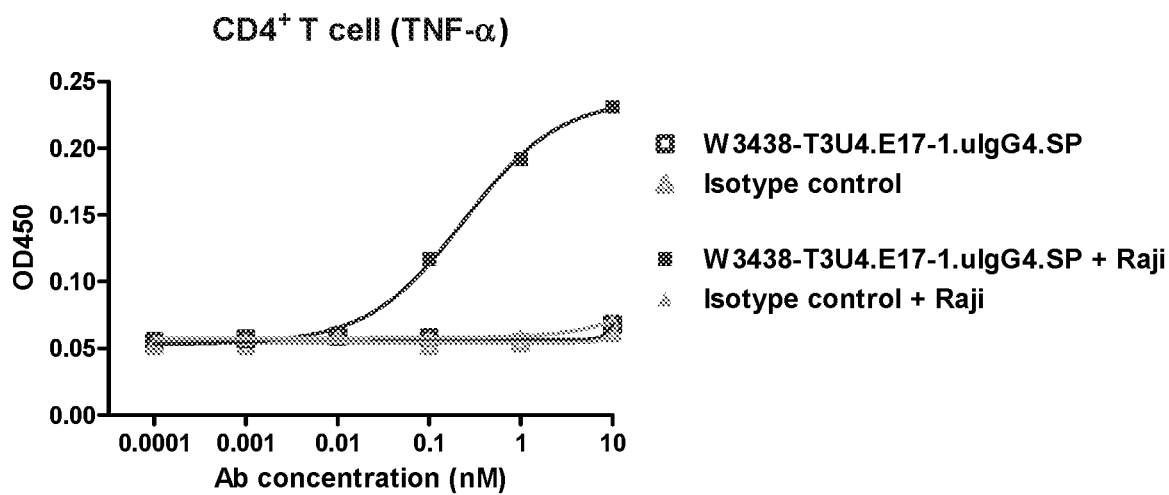
Figure 18C:
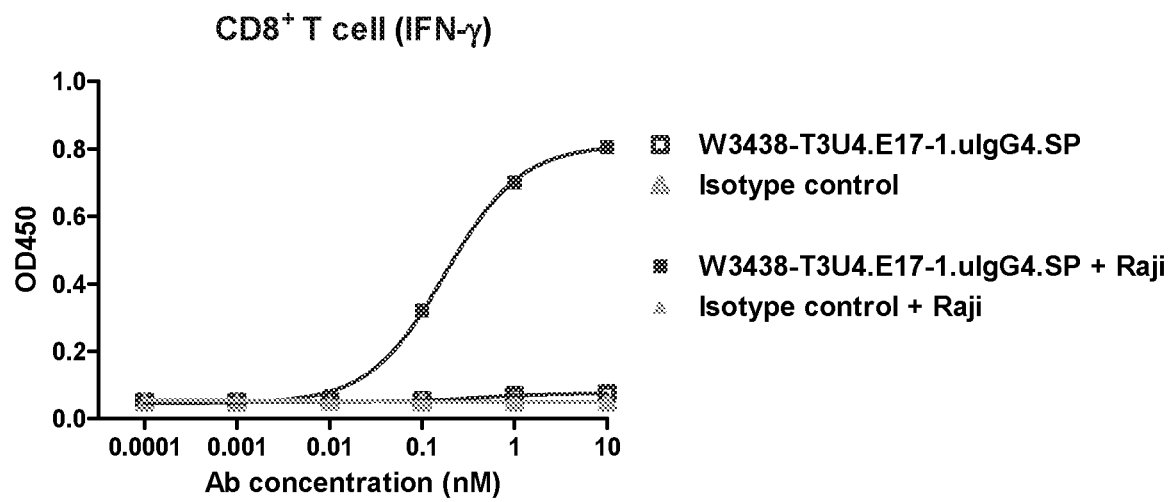
Figure 18D:
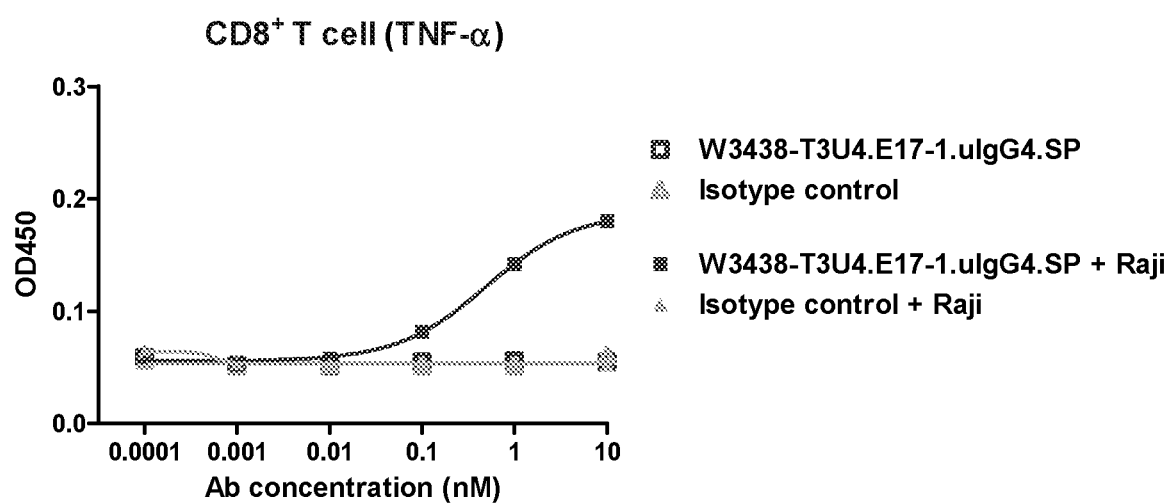

The binding affinity of W3438-T3U4.E17-1.uIgG4.SP to human CD19 and CD3 was tested on Ramos and Jurkat cells by flow cytometry. The bound IgG/free IgG versus bound IgG was plotted in FIGS. 14A-14B. The fitted $K_D$ values of binding to CD19 and CD3 were 23 nM and 9.0 nM, respectively.

Dual Binding on Target Cells

The activity of W3438-T3U4.E17-1.uIgG4.SP to bridge CD3 T cell and CD19 B cell was tested using pre-labeled Jurkat and Raji cells by flow cytometry (FIGS. 15A-15B). Q2 shows the population of bridged Jurkat and Raji cells. Compared with the negative control, roughly 18% of cells were bridged through bispecific antibody W3438-T3U4.E17-1.uIgG4.SP.

Cytotoxicity Assay

The cytotoxic activity of W3438-T3U4.E17-1.uIgG4.SP was evaluated using CD8+ T cell and raji cell. W3438-T3U4.E17-1.uIgG4.SP induced rapid and efficacious cell lysis after 4 hours incubation (FIG. 16A) with an $EC_{50}$ value of 15 nM. The maximum cell killing percentage was 90%.

The cytotoxic activity of W3438-T3U4.F16-1.uIgG4.SP was evaluated using CD8+ T cell and raji cell. W3438-T3U4.F16-1.uIgG4.SP induced rapid and efficacious cell lysis after 4 hours incubation (FIG. 16B) with an $EC_{50}$ value of 3.2 nM. The maximum cell killing percentage was 90%.

Target Specific T Cell Activation

W3438-T3U4.E17-1.uIgG4.SP was investigated in assays that indicate T cell activation through activation markers CD69 and CD25 in the presence or absence of CD19+ target cells. The results demonstrated that W3438-T3U4.E17-1.uIgG4.SP induces the expression of the T cell activation markers CD25 and CD69 in a dose-dependent manner only in the presence of CD19+ target cells (FIGS. 17A-17D). When the B cell is absent, no expression of CD25 and CD69 was observed in both CD4+ and CD8+ T cell subsets.

W3438-T3U4.E17-1.uIgG4.SP was also investigated in T cell activation assays of cytokine release in the presence or absence of CD19+ target cells. The results demonstrated that W3438-T3U4.E17-1.uIgG4.SP induces IFN-γ and TNF-α release in a dose-dependent manner only in the presence of CD19+ target cells (FIGS. 18A-18D). When the B cell is absent, no IFN-γ and TNF-α was detected in both CD4+ and CD8+ T cell subsets.

Thermal Stability

The thermal stability of W3438-T3U4.E17-1.uIgG4.SP was investigated using Real-Time PCR. $T_m1$ and $T_m2$ of W3438-T3U4.E17-1.uIgG4.SP are 60.2° C. and 72.7° C.

Serum Stability

Figure 19A:
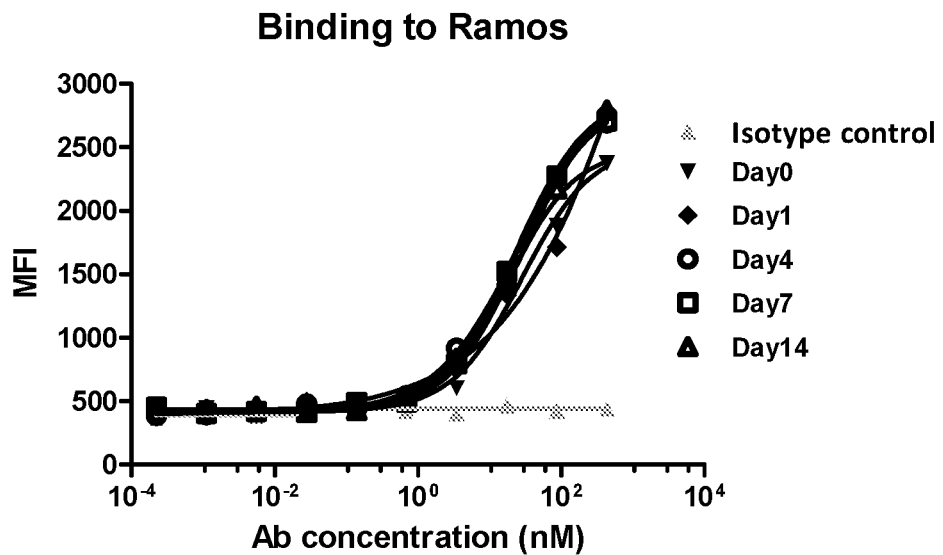
FIGS. 19A-19B show stability of W3438-T3U4.E17-1.uIgG4.SP in human serum. Binding of serum incubated W3438-T3U4.E17-1.uIgG4.SP samples to Ramos cells on indicated days (FIG. 19A); Binding of serum incubated W3438-T3U4.E17-1.uIgG4.SP samples to Jurkat on indicated days (FIG. 19B).
Figure 19B:
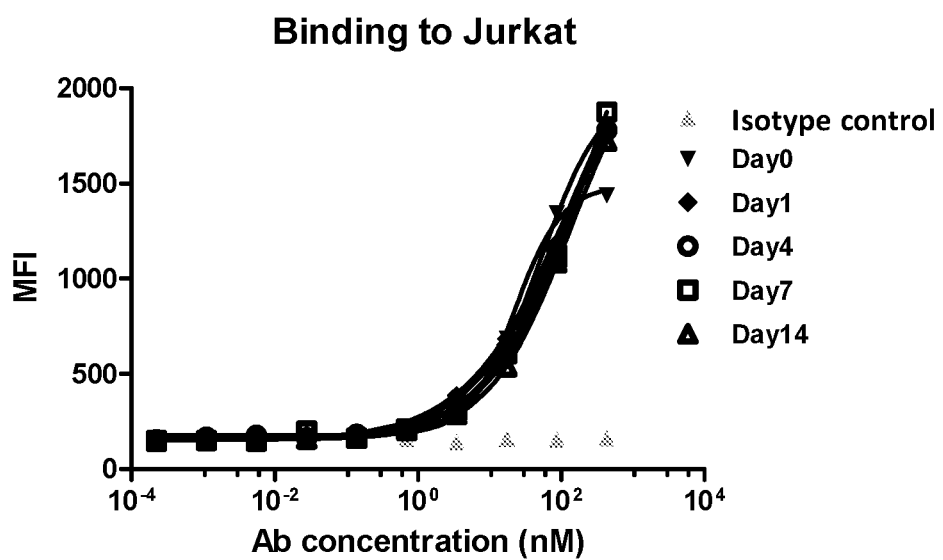

W3438-T3U4.E17-1.uIgG4.SP was incubated in serum at 37° C. for 14 days. The binding activity of the antibody incubated for 0, 1, 4, 7 and 14 days was detected by flow cytometry. The results showed that the binding activity of W3438-T3U4.E17-1.uIgG4.SP to both CD3 and CD19 cells was unchanged after incubating in human serum for 14 days (FIGS. 19A and 19B).

Fcγ Receptor Binding

The binding activity of W3438-T3U4.E17-1.uIgG4.SP to FcγRI, FcγRIIa (H167), FcγRIIa (R167), FcγRIIb, FcγRIIIa (F176), FcγRIIIa (V176) and FcγRIIIb were investigated by SPR. The affinities were summarized in Table 1. W3438-T3U4.E17-1.uIgG4.SP showed typical human IgG4 binding affinity to all the Fcγ receptors.

TABLE 1

Affinity of W3438-T3U4.E17-1.uIgG4.SP to Fc Receptor by SPR

| Fc receptor | $K_D$ (M) |
|---|---|
| FcγRI | 9.79E−09 |
| FcγRIIa (H167) | 2.05E−05 |
| FcγRIIa (R167) | 1.58E−05 |
| FcγRIIb | 2.41E−05 |
| FcγRIIIa (F176) | 2.93E−05 |
| FcγRIIIa (V176) | 1.40E−05 |
| FcγRIIIb | >4.10E−05 |

Figure 20:
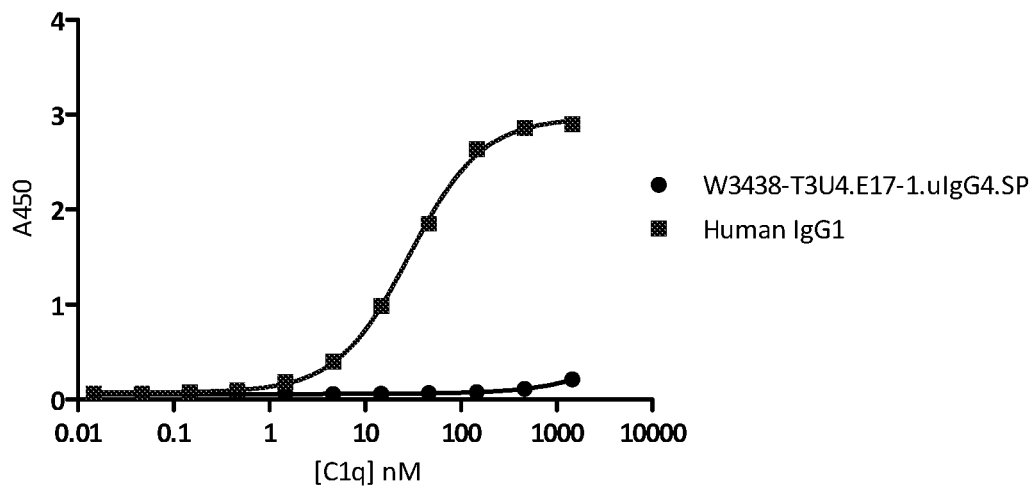
FIG. 20 shows binding of W3438-T3U4.E17-1.uIgG4.SP to C1Q by ELISA. An IgG1 antibody was used as the assay control.

The binding activity of antibodies to C1Q was tested by ELISA. W3438-T3U4.E17-1.uIgG4.SP showed no binding signal in ELISA (FIG. 20), and the control human IgG1 antibody showed normal binding signal.

FcRn Binding

The binding of W3438-T3U4.E17-1.uIgG4.SP to FcRn was tested by SPR at pH 6.0. The affinity was fitted as 2.58 μM which is a typical affinity of human IgG4 to FcRn.

In Vivo Characterization

Efficacy Study in the PBMC/Raji Xenograft Model

Figure 21:
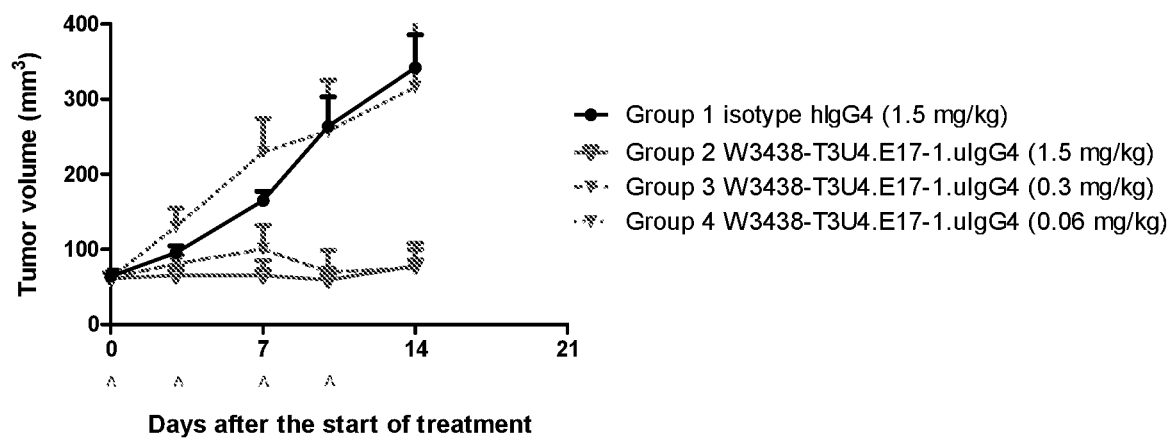
FIG. 21 shows tumor volume trace after administering W3438-T3U4.E17-1.uIgG4.SP at different doses to admixed PBMC humanized mice bearing Raji xenografts tumors. Data points represent group mean, error bars represent standard error of the mean (SEM). An irrelavant IgG4 antibody was used as a negative control.

In this study, anti-tumor efficacy of W3438-T3U4.E17-1.uIgG4.SP in the admixed PBMC humanized model bearing Raji cell in NOG mice was investigated. The tumor growth curve is shown in FIG. 21.

At D14, the mean tumor size of the isotype control treatment group reached 342 mm³. The treatment with 1.5 mg/kg and 0.5 mg/kg of W3438-T3U4.E17-1.uIgG4.SP produced a significant antitumor activity. The mean tumor size was respectively 78 mm³ (T/C=23.0%, TGI=93.9%, p=0.016) and 75 mm³ (T/C=22.0%, TGI=95.3%, p=0.014), and the tumor of one animal in high dosing level group was eradicated. W3438-T3U4.E17-1.uIgG4.SP at very low dose (0.06 mg/kg) did not show any antitumor activity.

Pharmacokinetics of WuXiBody in Cynomolgus Monkey

Figure 22:
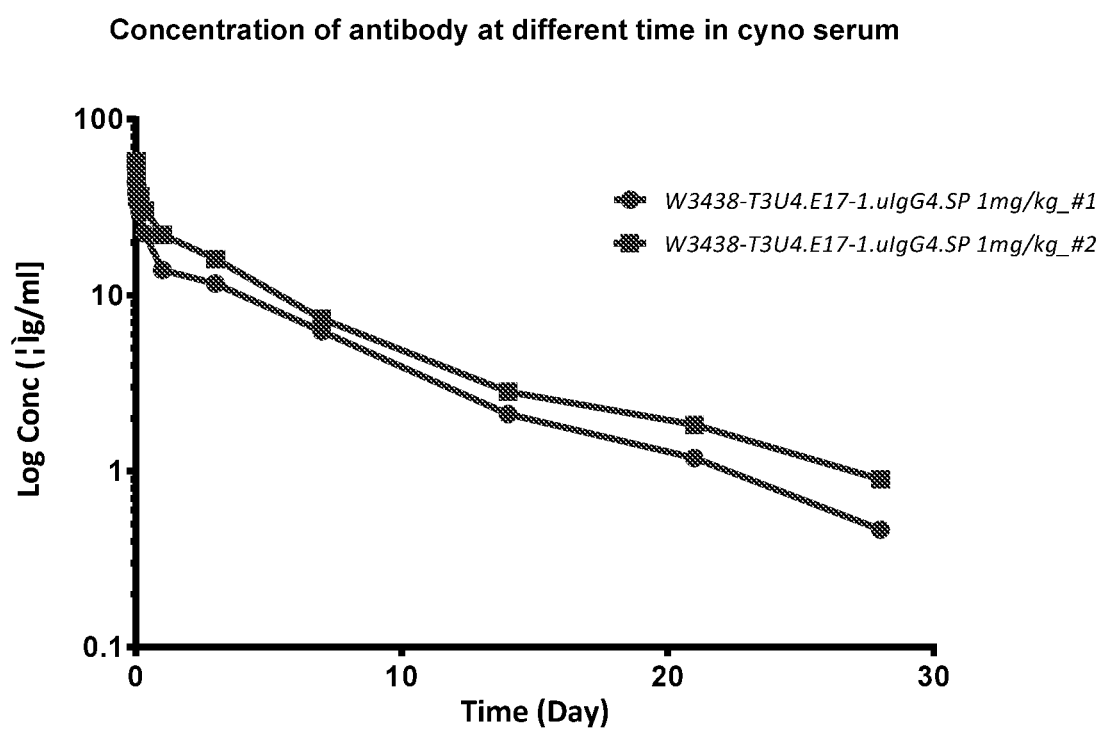
FIG. 22 shows concentrations of W3438-T3U4.E17-1.uIgG4.SP in cynomolgus monkey serum after a single dose of 1 mg/kg. The serum samples from two monkey were detected by ELISA.

The concentration of W3438-T3U4.E17-1.uIgG4.SP in cynomolgus serum was tested by ELISA (FIG. 22). The calculated PK parameters were listed in Table 2. The half life of W3438-T3U4.E17-1.uIgG4.SP for once single IV injection at 1 mg/kg was 152 hours. W3438-T3U4.E17-1.uIgG4.SP showed much longer half life in monkey than blinatumomab which has a very short half-life (1.5-2.6 hours) in chimpanzees (European Medicines Agency assessment report EMA/CHMP/469312/2015).

TABLE 2

Cynomolgus PK of W3438-T3U4.E17-1.uIgG4.SP

| PK parameter | W3438-T3U4.E17-1.uIgG4.SP |
|---|---|
| $C_0$ (μg/mL) | 60.4 |
| $T_{1/2}$ (h) | 152 |

TABLE 2-continued

Cynomolgus PK of W3438-T3U4.E17-1.uIgG4.SP

| PK parameter | W3438-T3U4.E17-1.uIgG4.SP |
| --- | --- |
| $Vd_{ss}$ (L/kg) | 0.0513 |
| Cl (mL/min/kg) | 0.00462 |
| $AUC_{0-last}$ (h*μg/mL) | 3552 |
| $AUC_{0-inf}$ (h*μg/mL) | 3708 |
| $MRT_{0-last}$ (h) | 157 |
| $MRT_{0-inf}$ (h) | 187 |

Toxicity

All monkeys tolerated the drug well during the entire course of the study. No adverse effects were observed during the in-life phase of the study. There was no obvious change in food consumption and weight. The parameters for Hematology and Clinical Chemistry, including AST, ALT, WBC, HGB and HCT were generally within the reference range.

Immunogenicity

Figure 23A:
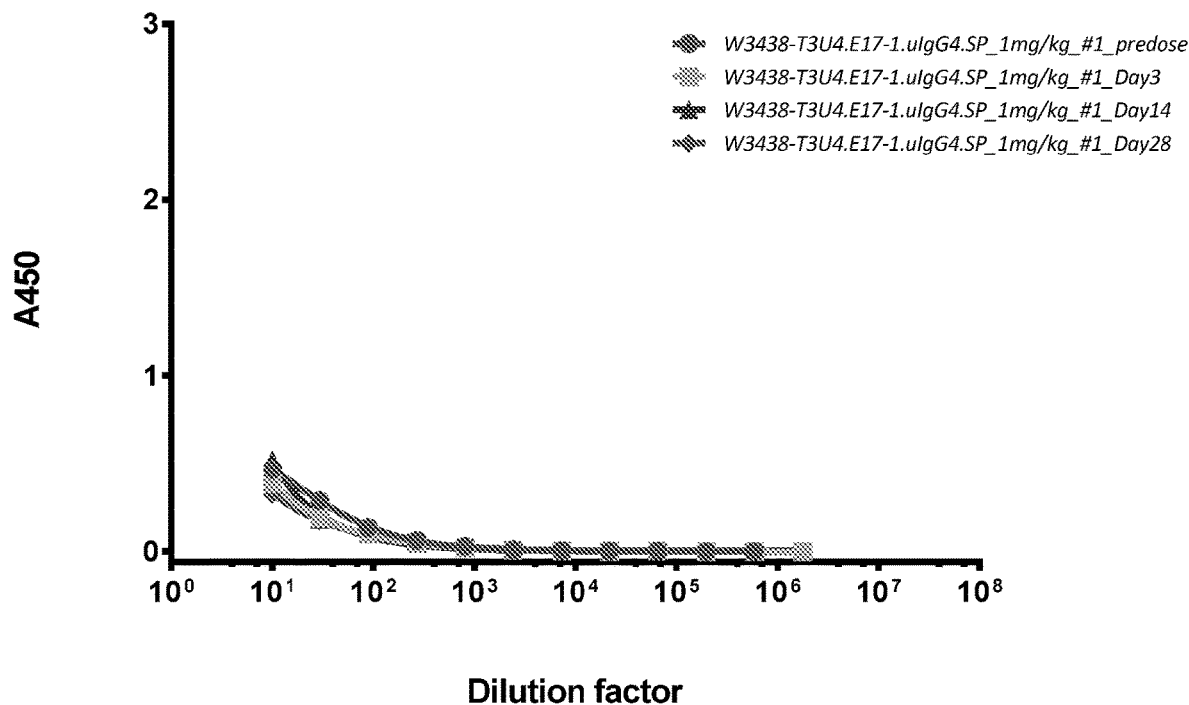
FIGS. 23A-23B show the anti-drug antibody (ADA) in serum samples from monkey #1 (FIG. 23A) and monkey #2 (FIG. 23B), including both predose and postdose of W3438-T3U4.E17-1.uIgG4.SP.
Figure 23B:
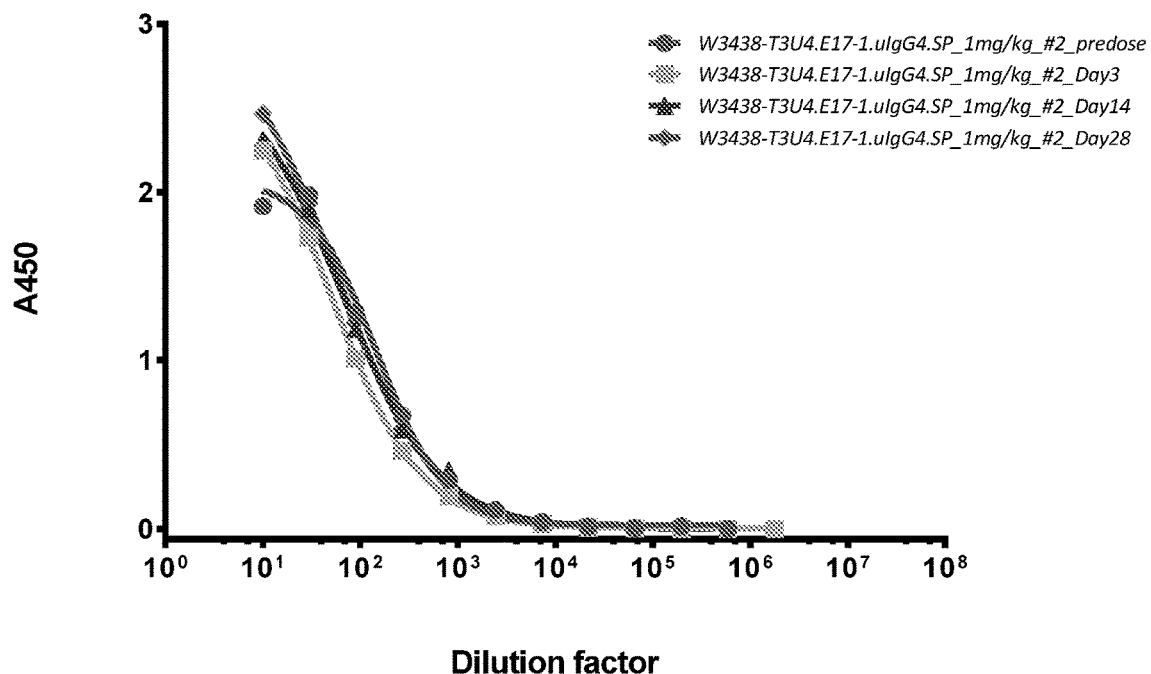

The results of anti-drug antibody (ADA) of W3438-T3U4.E17-1.uIgG4.SP are shown in FIGS. 23A-23B. The titers of ADA against W3438-T3U4.E17-1.uIgG4.SP in monkey serum of 3, 14 and 28 days post-dosing showed no significant difference from predose. Therefore, the single IV injection of W3438-T3U4.E17-1.uIgG4.SP at 1 mg/kg appeared not immunogenic in monkeys.

What is claimed:

1. A bispecific polypeptide complex, comprising a first antigen-binding moiety associated with a second antigen-binding moiety, wherein:
the first antigen-binding moiety comprises:
a first polypeptide comprising, from N-terminus to C-terminus, a first heavy chain variable domain (VH) of a first antibody operably linked to a first T cell receptor (TCR) constant region (C1), and
a second polypeptide comprising, from N-terminus to C-terminus, a first light chain variable domain (VL) of the first antibody operably linked to a second TCR constant region (C2), wherein:
C1 comprises an engineered CBeta comprising SEQ ID NO: 1 and C2 comprises an engineered CAlpha comprising SEQ ID NO: 2,
amino acid C48 in SEQ ID NO: 1 and amino acid C41 in SEQ ID NO: 2 are capable of forming a non-native interchain disulphide bond,
C1 and C2 are capable of forming a dimer, and the non-native interchain disulphide bond is capable of stabilizing the dimer, and
the second antigen-binding moiety comprises:
a second VH of a second antibody operably linked to an antibody heavy chain CH1 domain, and a second VL of the second antibody operably linked to an antibody light chain constant (CL) domain,
wherein:
one of the first and the second antigen-binding moiety is an anti-CD3 binding moiety, and the other one is an anti-CD19 binding moiety,
the anti-CD3 binding moiety is derived from an anti-CD3 antibody comprising:
a) a heavy chain CDR1 comprising SEQ ID NO: 3, b) a heavy chain CDR2 comprising SEQ ID NO: 4, c) a heavy chain CDR3 comprising SEQ ID NO: 5, d) a kappa light chain CDR1 comprising SEQ ID NO: 6, e) a kappa light chain CDR2 comprising SEQ ID NO: 7, and f) a kappa light chain CDR3 comprising SEQ ID NO: 8;
the anti-CD19 binding moiety is derived from an anti-CD19 antibody comprising:
a) a heavy chain CDR1 comprising SEQ ID NO: 9, b) a heavy chain CDR2 comprising SEQ ID NO: 10, c) a heavy chain CDR3 comprising SEQ ID NO: 11, d) a kappa light chain CDR1 comprising SEQ ID NO: 12,
e) a kappa light chain CDR2 comprising SEQ ID NO: 13, and f) a kappa light chain CDR3 comprising SEQ ID NO: 14, and
the first antigen-binding moiety and the second antigen-binding moiety are less prone to mispair than otherwise would have been if both the first and the second antigen-binding moieties are counterparts of natural Fab.

2. The bispecific polypeptide complex of claim 1, wherein the anti-CD3 binding moiety comprises a heavy chain variable domain sequence comprising SEQ ID NO: 15 and a light chain variable domain sequence comprising SEQ ID NO: 17.

3. The bispecific polypeptide complex of claim 1, wherein the anti-CD19 binding moiety comprises a heavy chain variable domain sequence comprising SEQ ID NO: 19 and a light chain variable domain sequence comprising SEQ ID NO: 21.

4. The bispecific polypeptide complex of claim 1, wherein:
the first VH is operably linked to C1 at a first conjunction domain, and
the first VL is operably linked to C2 at a second conjunction domain,
wherein the first conjunction domain comprises or is SEQ ID NO: 23, and/or the second conjunction domain comprises or is SEQ ID NO: 24.

5. The bispecific polypeptide complex of claim 1, wherein the first antigen-binding moiety is linked to a first dimerization domain, and the second antigen-binding moiety is linked to a second dimerization domain, wherein the first and the second dimerization domains are associated, and wherein the association is via a connecter, a disulphide bond, a hydrogen bond, electrostatic interaction, a salt bridge, hydrophobic interaction, hydrophilic interaction, or a combination thereof.

6. The bispecific polypeptide complex of claim 5, wherein the first and/or the second dimerization domain comprises at least a portion of an antibody hinge region, optionally derived from IgG1, IgG2 or IgG4.

7. The bispecific polypeptide complex of claim 5, wherein the first and/or the second dimerization domain comprises an antibody CH2 domain, and/or an antibody CH3 domain.

8. The bispecific polypeptide complex of claim 5, wherein the first dimerization domain is operably linked to the first TCR constant region (C1) at a third conjunction domain, wherein the third conjunction domain comprises SEQ ID NO: 25.

9. The bispecific polypeptide complex of claim 5, wherein the second dimerization domain is operably linked to the heavy chain variable domain of the second antigen-binding moiety.

10. The bispecific polypeptide complex of claim 5, wherein the association is via knobs-into-holes.

11. The bispecific polypeptide complex of claim 1, wherein the bispecific polypeptide complex comprises a combination of four polypeptide sequences: SEQ ID NO: 26, SEQ ID NO: 27, SEQ ID NO: 28, and SEQ ID NO: 29.

12. The bispecific polypeptide complex of claim 1, wherein the bispecific polypeptide complex comprises a combination of four polypeptide sequences: SEQ ID NO: 26, SEQ ID NO: 27, SEQ ID NO: 28, and SEQ ID NO: 30.

13. A conjugate comprising the bispecific polypeptide complex of claim 1, conjugated to a moiety.

14. An isolated polynucleotide encoding the bispecific polypeptide complex of claim 1.

15. An isolated vector comprising the polynucleotide of claim 14.

16. A host cell comprising the isolated polynucleotide of claim 14 or the isolated vector of claim 15.

17. A method of producing a bispecific polypeptide complex, comprising:
a) introducing to a host cell one or more polynucleotides encoding the bispecific polypeptide complex of claim 1,
b) allowing the host cell to express the bispecific polypeptide complex, and
c) isolating the bispecific polypeptide complex.

18. A pharmaceutical composition comprising the bispecific polypeptide complex of claim 1 and a pharmaceutically acceptable carrier.

19. A method of treating a CD19-related disease or condition in a subject in need thereof, comprising administrating to the subject a therapeutically effective amount of the bispecific polypeptide complex of claim 1, wherein the disease or condition is cancer.

20. A kit comprising the bispecific polypeptide complex of claim 1 and instructions for using the bispecific polypeptide complex for detection, diagnosis, prognosis, or treatment of a CD19-related disease or condition.

* * * * *

UNITED STATES PATENT AND TRADEMARK OFFICE
CERTIFICATE OF CORRECTION

| | | |
|---|---|---|
| PATENT NO. | : 11,365,254 B2 | Page 1 of 1 |
| APPLICATION NO. | : 16/648792 | |
| DATED | : June 21, 2022 | |
| INVENTOR(S) | : Liu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 162 days.

Signed and Sealed this
Ninth Day of April, 2024

Katherine Kelly Vidal
*Director of the United States Patent and Trademark Office*